United States Patent
Asrat et al.

(10) Patent No.: US 11,964,016 B2
(45) Date of Patent: Apr. 23, 2024

(54) COMBINATION OF IL-4/IL-13 PATHWAY INHIBITORS AND PLASMA CELL ABLATION FOR TREATING ALLERGY

(71) Applicant: REGENERON PHARMACEUTICALS, INC., Tarrytown, NY (US)

(72) Inventors: Seblewongel Asrat, New York, NY (US); Andre Limnander, New York, NY (US); Jamie Orengo, Cortlandt Manor, NY (US); Andrew J. Murphy, Croton-on-Hudson, NY (US); George D. Yancopoulos, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 708 days.

(21) Appl. No.: 16/825,955

(22) Filed: Mar. 20, 2020

(65) Prior Publication Data
US 2020/0345843 A1 Nov. 5, 2020

Related U.S. Application Data

(60) Provisional application No. 62/957,550, filed on Jan. 6, 2020, provisional application No. 62/822,022, filed on Mar. 21, 2019.

(51) Int. Cl.
| | | |
|---|---|---|
| A61K 39/39 | (2006.01) | |
| A61K 39/395 | (2006.01) | |
| A61P 37/08 | (2006.01) | |
| A61K 39/00 | (2006.01) | |

(52) U.S. Cl.
CPC .......... *A61K 39/3955* (2013.01); *A61P 37/08* (2018.01); *A61K 2039/507* (2013.01)

(58) Field of Classification Search
CPC .......... A61K 2039/507; A61K 39/3955; A61P 37/08
See application file for complete search history.

(56) References Cited

U.S. PATENT DOCUMENTS

| | | |
|---|---|---|
| 5,599,905 A | 2/1997 | Mosley |
| 5,714,146 A | 2/1998 | Lewis |
| 5,717,072 A | 2/1998 | Mosley |
| 5,856,296 A | 1/1999 | Mosley |
| 5,985,280 A | 11/1999 | Ritter |
| 6,156,877 A | 12/2000 | Ritter |
| 6,391,581 B1 | 5/2002 | Mosley |
| 6,548,655 B1 | 4/2003 | Mosley |
| 6,716,587 B2 | 4/2004 | Mosley |
| 7,141,653 B2 | 11/2006 | Greenfeder |
| 7,186,809 B2 | 3/2007 | Pluenneke |
| 7,317,090 B2 | 1/2008 | Mosley |
| 7,422,742 B2 | 9/2008 | Greenfeder |
| 7,531,169 B2 | 5/2009 | Singh |
| 7,605,237 B2 | 10/2009 | Stevens |
| 7,608,693 B2 | 10/2009 | Martin |
| 7,615,213 B2 | 10/2009 | Kasaian et al. |
| 7,794,717 B2 | 9/2010 | Stevens |
| 8,030,003 B2 | 10/2011 | Rothenberg |
| 8,075,887 B2 | 12/2011 | Martin |
| 8,075,897 B2 | 12/2011 | Spertini |
| 8,092,802 B2 | 1/2012 | Stevens |
| 8,092,804 B2 | 1/2012 | Eriksson |
| 8,252,284 B2 | 8/2012 | Singh |
| 8,324,192 B2 | 12/2012 | Dohil |
| 8,337,839 B2 | 12/2012 | Martin |
| 8,338,135 B2 | 12/2012 | Stevens |
| 8,497,528 B2 | 7/2013 | Lee |
| 8,604,171 B2 | 12/2013 | Singh |
| 8,637,239 B2 | 1/2014 | Furuta |
| 8,735,095 B2 | 5/2014 | Martin et al. |
| 8,945,559 B2 | 2/2015 | Dix |
| 9,238,692 B2 | 1/2016 | Dix |
| 9,290,574 B2 | 3/2016 | Kostic |
| 9,334,331 B2 * | 5/2016 | Igawa .................... C07K 16/40 |

(Continued)

FOREIGN PATENT DOCUMENTS

| | | |
|---|---|---|
| EP | 0604693 | 7/1994 |
| EP | 0367566 | 5/1997 |

(Continued)

OTHER PUBLICATIONS

Grunewald, the Journal of Immunology, 1998, Vo: 160, No. 8, pp. 4004-4009.*
Caraccio et al., (Frontiers in Immunology, Apr. 2020, vol. 11, Article 501, pp. 1-25).*
Garraud, Olivier, et al., "Regulation of immunoglobulin production in hyper-IgE (Job's) syndrome", J. Allergy Clin. Immunol., Feb. 1999. (2 Pt. 1): 333-340.
Finkelman, Fred, et al., "Regulation of murine in vivo IgG and IgE responses by a monoclonal anti-IL-4 receptor antibody", Jun. 1991;3(6); 599-607.
Chen, Ching, et al., "Enhancement and destruction of antibody function by somatic mutation: unequal occurrence is controlled by V gene combinatorial associations", The EMBO Journal vol. 15, No. 12, pp. 2784-2794, 1995.

(Continued)

*Primary Examiner* — Gyan Chandra
(74) *Attorney, Agent, or Firm* — Merchant & Gould P.C.

(57) ABSTRACT

The present disclosure provides methods for treating allergy comprising selecting a patient with an allergy and administering a therapeutically effective amount of an IL-4/IL-13 pathway inhibitor (e.g., an anti-IL-4 receptor antibody or antigen-binding fragment thereof) in combination with a therapeutically effective amount of an agent that depletes plasma cells (e.g., an anti-BCMA/anti-CD3 bispecific antibody). In certain embodiments, a plasma cell ablating agent such as an anti-BCMA/anti-CD3 bispecific antibody ablates the plasma cells, including IgE+ plasma cells, while the IL-4/IL-13 pathway inhibitor prevents the generation of new IgE+ plasma cells, thus eliminating allergen-specific IgE in the patient.

99 Claims, 14 Drawing Sheets
Specification includes a Sequence Listing.

(56) References Cited

U.S. PATENT DOCUMENTS

| | | |
|---|---|---|
| 9,415,015 B2 | 8/2016 | Jacobi et al. |
| 9,574,004 B2 | 2/2017 | Ardeleanu |
| 10,059,771 B2 | 8/2018 | Mannent |
| 10,066,017 B2 | 9/2018 | Mannent |
| 10,137,193 B2 | 11/2018 | Pirozzi |
| 10,370,449 B2 | 8/2019 | Graham |
| 10,392,439 B2 | 8/2019 | Stahl |
| 10,421,807 B2 * | 9/2019 | Gonzales ............... A61P 11/00 |
| 10,435,473 B2 | 10/2019 | Dix |
| 10,485,844 B2 | 11/2019 | Radin |
| 10,669,341 B2 | 6/2020 | Stahl |
| 10,676,530 B2 | 6/2020 | Stahl |
| 10,730,948 B2 | 8/2020 | Kostic |
| 11,034,768 B2 | 6/2021 | Amin |
| 11,053,309 B2 | 7/2021 | Radin |
| 2003/0103938 A1 | 6/2003 | Jinquan |
| 2003/0113387 A1 | 6/2003 | Tsuchida |
| 2003/0124121 A1 | 7/2003 | Pluenneke |
| 2005/0031609 A1 | 2/2005 | Hultsch |
| 2005/0074462 A1 | 4/2005 | Holmgren |
| 2005/0118176 A1 | 6/2005 | Mosley |
| 2005/0255532 A1 | 11/2005 | Ruben |
| 2005/0282181 A1 | 12/2005 | Yan |
| 2006/0013811 A1 | 1/2006 | Dina |
| 2007/0041976 A1 | 2/2007 | Pluenneke |
| 2007/0274996 A1 | 11/2007 | Carter |
| 2008/0054606 A1 | 5/2008 | Eriksson |
| 2008/0160035 A1 | 7/2008 | Stevens et al. |
| 2009/0074793 A1 | 3/2009 | Martin |
| 2009/0098142 A1 | 4/2009 | Kasaian |
| 2009/0264392 A1 | 10/2009 | Warndahl |
| 2010/0021476 A1 | 1/2010 | Stevens et al. |
| 2010/0047254 A1 | 2/2010 | Martin |
| 2010/0291107 A1 | 11/2010 | Stevens et al. |
| 2011/0195500 A1 | 8/2011 | Rothenberg |
| 2012/0004205 A1 | 1/2012 | Rothenberg |
| 2012/0052072 A1 | 3/2012 | Martin |
| 2012/0097565 A1 | 4/2012 | Dix |
| 2012/0135010 A1 | 5/2012 | Stevens et al. |
| 2012/0164080 A1 | 6/2012 | Hill |
| 2012/0207815 A1 | 8/2012 | Benhamou |
| 2013/0052190 A1 | 2/2013 | Collins |
| 2013/0078675 A1 | 3/2013 | Martin |
| 2013/0324435 A1 | 12/2013 | Rothenberg |
| 2014/0072583 A1 | 3/2014 | Ardeleanu |
| 2014/0187523 A1 | 7/2014 | Dohil |
| 2014/0271681 A1 | 9/2014 | Martin |
| 2014/0356372 A1 | 12/2014 | Stahl |
| 2015/0017176 A1 | 1/2015 | Kostic |
| 2015/0185228 A1 | 7/2015 | Reisacher |
| 2015/0246973 A1 | 9/2015 | Graham |
| 2016/0152718 A1 | 6/2016 | Kostic |
| 2016/0185866 A1 | 6/2016 | Mannent |
| 2017/0333557 A1 | 11/2017 | Ardeleanu |
| 2018/0078603 A1 | 3/2018 | Radin |
| 2018/0094069 A1 | 4/2018 | Stahl |
| 2018/0094070 A1 | 4/2018 | Stahl |
| 2018/0169220 A1 | 6/2018 | Euverink et al. |
| 2018/0179288 A1 | 6/2018 | Martin et al. |
| 2019/0040126 A1 | 2/2019 | Radin |
| 2019/0169299 A1 | 6/2019 | Amin |
| 2019/0183973 A1 | 6/2019 | Hamilton |
| 2019/0345253 A1 | 11/2019 | Bansal |
| 2019/0367622 A1 | 12/2019 | Graham |
| 2020/0246416 A1 | 8/2020 | Radin |
| 2020/0299393 A1 | 9/2020 | Stahl |
| 2020/0332014 A1 | 10/2020 | Kostic |
| 2021/0000949 A1 | 1/2021 | Goulaouic et al. |
| 2021/0038715 A1 | 2/2021 | Hamilton |
| 2021/0040222 A1 | 2/2021 | Bansal |
| 2021/0163611 A1 | 6/2021 | Martin |
| 2021/0220470 A1 | 7/2021 | Bryce et al. |
| 2021/0363237 A1 | 11/2021 | Radin |
| 2021/0363264 A1 | 11/2021 | Hamilton |
| 2022/0110999 A1 | 4/2022 | Radin |
| 2022/0220211 A1 | 7/2022 | Orengo |
| 2022/0298250 A1 | 9/2022 | Bansal |
| 2023/0159647 A1 | 5/2023 | Stahl |
| 2023/0293682 A1 | 9/2023 | Hamilton |

FOREIGN PATENT DOCUMENTS

| | | |
|---|---|---|
| EP | 1113818 B1 | 5/2006 |
| EP | 2022507 A1 | 2/2009 |
| EP | 1527100 | 7/2009 |
| JP | 05-246874 | 9/1993 |
| JP | 2006-131623 | 5/2006 |
| JP | 2016521713 | 7/2016 |
| RU | 2162711 | 2/2001 |
| RU | 2283665 C2 | 9/2006 |
| RU | 2453303 C1 | 6/2012 |
| RU | 2552929 C1 | 6/2015 |
| WO | WO 1992/19259 | 11/1992 |
| WO | WO 1994/14975 | 7/1994 |
| WO | WO 2001/092340 | 12/2001 |
| WO | WO 2003/048083 | 6/2003 |
| WO | WO 2005/047331 | 5/2005 |
| WO | WO 2005/085284 | 9/2005 |
| WO | WO 2006/003407 | 1/2006 |
| WO | WO 2006/072564 | 7/2006 |
| WO | WO 2006/083390 | 8/2006 |
| WO | WO 2008/054606 | 5/2008 |
| WO | 2008/116149 | 9/2008 |
| WO | WO 2009/124954 | 10/2009 |
| WO | WO 2010/053751 | 5/2010 |
| WO | WO 2010/065557 | 6/2010 |
| WO | WO 2010/120524 | 10/2010 |
| WO | WO 2011/026966 | 3/2011 |
| WO | WO 2012/047954 | 4/2012 |
| WO | WO 2012/094643 | 7/2012 |
| WO | WO 2012/177945 | 12/2012 |
| WO | WO 2013/051928 | 4/2013 |
| WO | WO 2013/088109 | 6/2013 |
| WO | 2013/116287 | 8/2013 |
| WO | WO 2013/155010 | 10/2013 |
| WO | WO 2014/031610 | 2/2014 |
| WO | WO 2014/039461 | 3/2014 |
| WO | WO 2014/059178 | 4/2014 |
| WO | 2014/122144 | 8/2014 |
| WO | WO 2014/197470 | 12/2014 |
| WO | WO 2014/205365 | 12/2014 |
| WO | WO 2015/006571 | 1/2015 |
| WO | 2015/127229 | 8/2015 |
| WO | WO 2016/077675 | 5/2016 |
| WO | WO 2017/143270 | 8/2017 |
| WO | 2018/035393 | 2/2018 |
| WO | WO 2018/045130 | 3/2018 |
| WO | WO 2018/057776 | 3/2018 |
| WO | 2018/151836 | 8/2018 |
| WO | 2018/201051 | 11/2018 |
| WO | 2019/089473 | 5/2019 |
| WO | 2019/240288 | 12/2019 |
| WO | 2021/195530 | 9/2021 |

OTHER PUBLICATIONS

Kussie, Paul, et al., "A Single Engineered Amino Acid Substitution Changes Antibody Fine Specificity", Journal of Immunology:152, pp. 146-152, 1994.

"Dupilumab therapy in moderate-to-severe atopic dermatitis provides positive results in the first two phase III clinical trials", J Int Pharm Res, vol. 43, No. 4, Aug. 31, 2016, p. 785 (with English translation).

Clinical Trials, Study NCT00436670, "Phase II Study to Evaluate the Efficacy of AMG 317", first posted Feb. 19, 2007, Amgen actual study completion date—Feb. 2009, 7 pages.

Vincent, M. et al., "Single-Dose, First-in-Human Study of AMG 317: Pharmacokinetics and Safety in Healthy and Asthmatic Adults", the Journal of Allergy and Clinical Immunology, vol. 121, Issue 2, Supplement 1, S10, Abstract, Feb. 1, 2008, 1 page.

Russian Office Action and Search Report in Application 2020140639, dated Aug. 17, 2022, with English translation, 26 pages.

(56) References Cited

OTHER PUBLICATIONS

Blakely, Kim et al., "Dupilumab, a monoclonal antibody for atopic dermatitis: a review of current literature", Skin Therapy Letter, Mar.-Apr. 2016,vol. 21, No. 2, Dupilumab Clinical Trials in Ad, 13 pages.
Clinical Trials, Study NCT01859988, phase 2b, "Study of Dupilumab Administered to Adult Patients With Moderate-to-Severe Atopic Dermatitis", study completion date—Sep. 2014, 10 pages.
D'Erme, Angelo et al., "Spotlight on dupilumab in the treatment of atopic dermatitis: design, development, and potential place in therapy", Drug Des Devel Ther, 2017, vol. 11, p. 1473-1480, DOI:10.2147/DDDT.S113192, Abstract, c.1475-1478, 8 pages.
Grechkina, L.I. et al., "Characteristics for the physical development indices demonstrated by adolescents born in Magadan", Siberian Medical Journal, 2013, No. 3, Results and discussion, Table 1, obtained from: https://cyberleninka.ru/article/n/harakteristika-pokazateley-fizicheskogo-razvitiya-podrostkov-urozhentsev-magadana/viewer, with English translation, 9 pages.
Yamashita, Shuya et al., "Flavones suppress type I IL-4 receptor signaling by down-regulating the expression of common gamma chain", FEBS Letters, 2010, vol. 584, issue 4, p. 775-779, Abstract, Introduction, located at: https://febs.onlinelibrary.wiley.com/doi/full/10.1016/j.febslet.2009.12.044, 13 pages.
Balabolkin, I. et al., "Modern concepts of pathogenesis and therapy of atopic dermatitis in children", PHARMATEKA, 2017, No. 1, p. 53-60, with English translation, 14 pages.
Ayars, Andrew G. et al., "Pharmacologic Therapies in Pulmonology and Allergy", 2016 Med Clin N Am 100(4): 851-868.
Mashkovsky, M.D., Moscow, 2001 Medicines, 14th edition, v1:8-9. (Cited in RU Application 2019109062).
Russian Office Action and Search Report in Application 2019109062, with English translation, 32 pages.
Bergmann, M.M. et al., "Evaluation of Food Allergy in Patients With Atopic Dermatitis", J Allergy Clin Immunol, 1, pp. 22-28, Jan. 1, 2013.
Igelman, Sean et al., "Off-label use of dupilumab for pediatric patients with atopic dermatitis: A multicenter retrospective review", Journal of the American Academy of Dermatology, Mosby, Inc., US, vol. 82, No. 2, Oct. 10, 2019, pp. 407-411.
Gong, J.Q. et al., "Skin Colonization by *Staphylococcus aureus* in patients with eczema and atopic dermatits and relevant combined topical therapy: a double-blind multicentre randomized controlled trial", British Journal of Dermatology, No. 155, pp. 680-687 (2006), Mar. 28, 2006.
Cork et al., "An open-label phase IIa trial assessing the pharmacokinetics, safety and efficacy of dupilumab in a paediatric population with moderate-to-severe atopic dermatitis", P94, British Association of Dermatologists, Jul. 2017, 177 (Suppl. 1), pp. 25-77.
ClinicalTrials.gov Identifier: NTC02407756; Last Update posted Aug. 22, 2016, A Study to Determine the Safety and Tolerability of Dupilumab (REGN668/SAR231893) in Patients Aged >6 to <18 Years With Atopic Dermatitis (Eczema), 11 pages.
Dupixent (dupilumab) Injection, for Subcutaneous Use, Patient Information, Issued Mar. 2017, 34 pages.
Carr, Warner, "Topical Calcineurin Inhibitors for Atopic Dermatitis: Review and Treatment Recommendations", Pediatric Drugs, 2013, vol. 15, pp. 303-310.
Kharkevich, D.A., Pharmacology (Farmakologiya: A Scholarly Manual), 10th Ed., Moscow: GEOTAR-Media, 2010, pp. 73-74 and pp. 846-847, with English translation of cited pages, 12 pages total.
Krasnyuk et al., "Pharmaceutical Technology: Technology of Dosage Forms: A Textbook for College and University Students", 2nd standard edition, Moscow: Akademiya Publishing Center, 2006, p. 8-9, with English translation of cited pages, 7 pages total.
Blankestijn, Mark et al., "Could Duratumumab be used to treat severe allergy?", Journal of Allergy and Clinical Immunology, vol. 139, No. 5, Jan. 19, 2017, p. 1677-1678.e3.
Nagaraju et al., "Bortezomib treatment diminishes hazelnut-induced intestinal anaphylaxis in mice: Immunomodulation", European Journal of Immunology, vol. 46, No. 7, May 11, 2016, pp. 1727-1736.
Winter, Oliver et al., "Pathogenic Long-Lived Plasma Cells and Their Survival Niches in Autoimmunity, Malignancy, and Allergy", The Journal of Immunology, vol. 189, No. 11, Nov. 19, 2012, pp. 5105-5111.
Abonia et al. (2013) Journal of Allergy Clin Immunol "High prevalence of eosinophilic esophagitis in patients with inherited connective tissue disorders".
Abstracts, "Human Clinical Research and Therapeutics", Journal of Investigative Dermatology vol. 133, Supplement 1, (2013), pp. S159-S190, Abstracts 1042, and 1048 to 1050, http://apps.webofknowledge.com/full_record.do?product=WOS&search_mode=GeneralSearch&qid=2& SID=E6MDFsiCnXC9MfROx21&page=1&doc=1, 32 pages.
Aceves et al. (2009) Immunol Allergy Clin N Am 29:197-211 "Relationships Between Eosinophilic Inflammation, Tissue Remodeling, and Fibrosis in Eosinophilic Esophagitis".
Akiyama, et al., A Study on Indoor Allergens Measured in Home Environments of Adult-Asthmatic Patients, Housing Research Foundation, Research Annual Report, 1997, No. 24, Study No. 9620, 1-10.
Almagro et al., "Humanization of antibodies", (2008) Frontiers in Bioscience 13:1619-1633.
Antoniu, Sabina, "Pitrakinra, a Dual IL-4R/IL-13 Antagonist for the Potential Treatment of Asthma and Eczema", Current Opinion in Investigational Drugs 2010 11 (11): 1286-1294.
Arron et al. (2009) Am. J. Respir. Crit. Care Med. Online Abstracts Issue. 2009, B21 Airway Inflammation: New Information about Mediators and Biomarkers/Poster Discussion/Monday, May 18, 2009 "Peripheral Biomarkers of an IL-13 Induced Bronchial Epithelial Gene Signature in Asthma".
Assa'ad et al. (2011) Gastroenterology 141:1593-1604 "An Antibody Against IL-5 Reduces Numbers of Esophageal Intraepithelial Eosinophils in Children with Eosinophilic Esophagitis".
Assa'ad, Amal, What is new in the Treatment of Eosinophilic Eosophagitis? Clinical and Translational Allergy 2011 (Suppl 1):S69, doi: 10.1186/2045-7022-1-S 1-S69.
Bachert et al. (2005) Drugs 65(11):1537-1552 "Pharmacological management of nasal polyposis".
Bagnasco, Diego et al., "A critical evaluation of Anti-IL-13 and Anti-IL-4 Strategies in Severe Asthma", Int. Arch Allergy Immunol 2016; 170: 122-131.
Balint and Larrick (1993) Gene 137:109-118 "Antibody engineering by parsimonious mutagenesis".
Bankhead, Charles, "IL-4 Antibody Tames Atopic Dermatitis", Medpage Today Article, https://www.medpagetoday.com/meetingcoverage/aad/37636, Mar. 3, 2013, 3 pages.
Barnes (2008) The Journal of Clinical Investigation 118(11):3546-3556 "The cytokine network in asthma and chronic obstructive pulmonary disease".
Bateman et al. (2004) Am. J. Respir. Crit. Care Med. 170:836-844 "Can guideline-defined asthma control be achieved?".
Beck et al. (Jul. 10, 2014) New England Journal of Medicine 371(2): 130-139 "Dupilumab treatment in adults with moderate-to-severe atopic dermatitis".
Beyer et al. (2002) Journal of Allergy Clin Immunol 109(4):707-713 "Human milk-specific mucosal lymphocytes of the gastrointestinal tract display a $T_H2$ cytokine profile".
Bhardwaj and Ghaffari (2012) Ann Allergy Asthma Immunol 109:155-159 "Biomarkers for eosinophilic esophagitis: a review".
Bieber, T., et al., "Atopic dermatitis: a candidate for disease-modifying strategy," Allergy 67 (2012) 969-975.
Blanchard and Rothenberg (2009) Immunol Allergy Clin N Am 29:141-148 "Chemotactic Factors Associated with Eosinophilic Gastrointestinal Diseases".
Blanchard et al. (2005) Clin Exp Allergy 35:1096-1103 "Inhibition of human interleukin-13-induced respiratory and oesophageal inflammation by anti-human-interleukin-13 antibody (CAT-354)".
Blanchard et al. (2006) The Journal of Clinical Investigation 116(2) "Eotaxin-3 and a uniquely conserved gene-expression profile in eosinophilic esophagitis".
Blanchard et al. (2007) Journal of Allergy Clin Immunol 120(6) "IL-13 involvement in eosinophilic esophagitis: Transcriptome analysis and reversibility with glucocorticoids".

(56) References Cited

OTHER PUBLICATIONS

Blanchard et al. (2010) The Journal of Immunology "Coordinate Interaction between IL-13 and Epithelial Differentiation Cluster Genes in Eosinophilic Esophagitis".
Blanchard et al. (2011) J Allergy Clin Immunol 127(1):208-217 "A striking local esophageal cytokine expression profile in eosinophilic esophagitis".
Blauvelt, Andrew, et al., "Long-term management of moderate-to-severe atopic dermatitis with dupilumab and concomitant topical corticosteroids (Liberty AD Chronos): a 1-year, randomised, double-blinded, placebo-controlled, phase 3 trial," www.thelancet.com, published online May 4, 2016, http://dx.doi.org/10.1016/S0140-6736 (17)31191-1.
British Society for Allergy And Clinical Immunology (BSACI) Abstracts of the 2013 Annual Meeting (dated Jul. 8-10, 2013), Clinical & Experimental Allergy, 43, 1428-1472, Nov. 22, 2013, https://onlinelibrary.wiley.com/toc/13652222/2013/43/12, 45 pages.
Brown-Whitehorn and Spergel (2010) Expert Rev Clin Immunol. 6:1:101-115 "The link between allergies and eosinophilic esophagitis: implications for management strategies".
BSACI News Report confirming BSACI conference date of Jul. 8-10, 2013, 2 pages.
Burmeister-Getz et al. (2009) J. Clin. Pharmacol. 49:1025-1036 "Human pharmacokinetics/pharmacodynamics of an interleukin-4 and interleukin-13 dual antagonist in asthma".
Burton, et al., "Direct effects of IL-4 on mast cells drive their intestinal expansion and increase susceptibility to anaphylaxis in a murine model of food allergy," Mucosal Immunology, Nov. 14, 2012, doi:10.1038/mi.2012.112.
Caldas et al. (2003) Molecular Immunology 39:941-952 "Humanization of the anti-CD18 antibody 6.7: an unexpected effect of a framework residue in binding to antigen".
Carter (2006) The Journal of Immunology 6:343-357 "Potent Antibody Therapeutics by Design".
Casset et al. (2003) Biochemical and Biophysical Research Communication 307:198-205 "A peptide mimetic of an anti-CD4 monoclonal antibody by rational design".
Chehade and Sampson (2009) Immunol Allergy Clin N Am 29:149-158 "The Role of Lymphocytes in Eosinophilic Gastrointestinal Disorders".
Cheng et al. (2012) Am J Physiol Gastrointest Liver Physiol 303:G1175-G1187 "Tissue remodeling in eosinophilic esophagitis".
Chien et al. (1989) Proc. Natl. Acad. Sci. 86:5532-5536 "Significant structural and functional change of an antigen-binding site by a distant amino acid substitution: Proposal of a structural mechanism".
Collins, Margaret H. et al., "Sa1151—Baseline Characteristics and Correlation Between Dysphagia and Disease Activity in Patients with Eosinophilic Esophagitis in a Randomized, Placebo-Controlled, Phase 2 Dupilumab Trial", abstract, Gastroenterology, vol. 154, No. 6, May 1, 2016, 1 page.
Corren et al. (2010) American Journal of Respiratory and Critical Care Medicine 181(8):788-796 "A Randomized, Controlled, Phase 2 Study of AMG 317, an IL-4R Antagonist, in Patients with Asthma".
Cortes, J.R., et al., Proton pump inhibitors inhibit IL-4 and IL-13 signaling stat6 activation, European Journal of Immunology, (Sep. 2009) vol. 39, Supp.
Davies et al. (1996) Immunotechnol. 2(3): 169-179 "Affinity improvement of single antibody VH domains: residues in all three hypervariable regions affect antigen binding".
Davis (2004) Seminars in Immunology 16:239-243 "The evolutionary and structural 'logic' of antigen receptor diversity".
De Pascalis et al. (2002) Journal of Immunology 169(6):3076-3084 "Grafting of "Abbreviated" Complementarity-Determining Regions Containing Specificity-Determining Residues Essential for Ligand Contact to Engineer a Less Immunogenic Humanized Monoclonal Antibody".
Dellon (2013) Dig Dis Sci "The Pathogenesis of Eosinophilic Esophagitis: Beyond the Eosinophil".
Dellon, Evan S. et al., "A Randomized, Double-Blind, Placebo-Controlled Trial of a Novel Recombinant, Humanized, Anti-Interleukin-13 Monoclonal Antibody (RPC4046) in Patients with Active Eosinophilic Esophagitis: Results of the HEROES Study", Oct. 14, 2016, retrieved from the Internet on Sep. 20, 2018 at: https://www.eventscribe.com/2016/ACG/QRcode.asp?Pres=178380, 3 pages.
Desreumaux et al. (1996) Gastroenterology 110:768-774 "Interleukin 3, Granulocyte-Macrophage Colony-Stimulating Factor, and Interleukin 5 in Eosinophilic Gastroenteritis".
Durham, Andrew L. et al., "Targeted anti-inflammatory therapeutics in asthma and chronic obstructive lung disease", Airway Disease Section, Nat'l. Heart and Lung Institute, Imperial College London, UK, published Aug. 12, 2015, 12 pages.
European Notice of Opposition in Application 13765844.9, mailed Feb. 22, 2019, 34 pages.
Fillon et al. (2009) Immunol Allergy Clin N Am 29:171-178 "Epithelial Function in Eosinophilic Gastrointestinal Diseases".
Foote and Winter (1992) J. Mol. Biol. 224:487-499 "Antibody Framework Residues Affecting the Conformation of the Hypervariable Loops".
Foroughi et al. (2007) J Allergy Clin Immunol 120(3):594-601 "Anti-IgE Treatment of Eosinophil Associated Gastrointestinal Disorders".
Franciosi and Liacouras (2009) Immunol Allergy Clin N Am 29:19-27 "Eosinophilic Esophagitis".
Garriga, A., "71st Annual Meeting of the American Academy of Dermatology (AAAD) . . . Miami Beach, FL, Mar. 1-5, 2013", Drugs of the Future 2013, 38(4): 275-279, Apr. 2013, https://journals.prous.com/journals/servlet/xmlxls/pk_journals.xml_toc_pr?p_JournalID=2&p_IssueID=1186, 5 pages.
Gavett et al. (1997) The American Physiological Society 272(16):L253-L261 "Interleukin-4 receptor blockade prevents airway responses induced by antigen challenge in mice".
Gevaert et al. (2006) Journal of Allergy and Clinical Immunology 118(5):1133-1141 "Nasal IL-5 levels determine the response to anti-IL-5 treatment in patients with nasal polyps".
Giusti et al. (1987) Proc. Natl. Acad. Sci. 84:2926-2930 "Somatic diversification of S107 from an antiphosphocholine to anti-DNA autoantibody is due to a single base change in its heavy chain variable region".
Groves et al. (2007) Aeroderm in AD Poster at St. John's Institute of Dermatology "Inhibition of IL-4 and IL-13 with an IL-4 mutein (Aeroderm) protects against flares in atopic eczema".
Grunewald et al. (1998) The Journal of Immunology 160(8):4004-4009 "An Antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo".
Gussow and Seemann (1991) Methods in Enzymology 203:99-121 "Humanization of Monoclonal Antibodies".
Hamilton, Jennifer D., et al., "Drug evaluation review: Dupilumab in atopic dermatitis," Immunotherapy (Oct. 1, 2015) 7(10), 1043-1058.
Hijnen et al. (2004) J. Allergy Clin. Immunology 113(2): 334-340 "Serum thymus and activation-regulated chemokine (TARC) and cutaneous T Cell-attracting chemokine (CTACK) levels in allergic diseases: TARC and CTACK are disease-specific markers for atopic dermatitis".
Hirano, Ikuo et al., "Dupilumab Efficacy and Safety in Adult Patients With Active Eosinophilic Esophagitis: a Randomized Double-Blind Placebo-Controlled Phase 2 Trial", Oct. 13, 2017, retrieved from the internet on Sep. 20, 2018 at: http://files.shareholder.com/downloads/REGN/6138593856x0x959724/16AF93AE-DAF8-480A-8301-311C91E8FA41/Presentation.pdf, 20 pages.
Hirano, Ikuo et al., "Sa1113-Correlation Between Esophageal Distensibility and Objective Measures of Disease in Patients with Active Eosinophilic Esophagitis: A Post HOC Analysis of a Randomized, Placebo-Controlled, Phase 2 Dupilumab Trial", abstract, Gastroenterology, vol. 154, No. 6, May 1, 2018, 1 page.
Holm et al. (2007) Molecular Immunology 44:1075-1084 "Functional mapping and single chain construction of the anti-cytokeratin 8 monoclonal antibody TS1".

(56) References Cited

OTHER PUBLICATIONS

Holt et al. (2003) Trends in Biotechnology 21(11):484-490 "Domain antibodies: proteins for therapy".
Hong, Judith, et al., "Management of Itch in Atopic Dermatitis," Seminars in cutaneous Medicine and Surgery, vol. 30, No. 2, May 14, 2011, pp. 71-86, XP028240445.
Hopkins (2009) Clinical Otolaryngology 34(5):447-454 "Psychometric validity of the 22-item Sinonasal Outcome Test".
Hopkins et al. (2007) Otolaryngology-Head and Neck Surgery 137(4):555-561 "The Lund-Mackay staging system for chronic rhinosinusitis: How is it used and what does it predict?".
International Investigative Dermatology, Edinburgh, Conference Posters, May 8-11, 2013, 4 pages.
Ivashkiin, V. T., et al., "Eosinophilic esophagitis," a textbook for physicians, Moscow, "AISPI RAS" JSC, Feb. 14, 2013, pp. 13-21, 57-62 No English translation. (Cited in Russian Office Action for RU Appl. No. 2016104400).
Ivashkin, V. T., et al., "Eosinophilic esophagitis: literature review and description of own survey," RJGHC, 2012, vol. 22, 1, pp. 71-81.
Jahnz-Rozyk et al. (2005) Allergy 60:685-688 "Serum thymus and activation-regulated chemokine, macrophage-derived chemokine and eotaxin as marker of severity of atopic dermatitis".
Joost, T.H. Van, "Cyclosporin in atopical dermatitis: a multicentre placebo-controlled study", Journal of the American Academy of Dermatology, (1992), vol. 27, Issue 6, Part 1, pp. 922-928.
Journal of Allergy & Clinical Immunology: Abstracts at conference; https://www.jacionline.org/issue/S0091-6749 (13)X0013-2, Feb. 2013, 1 page.
Junttila et al. (2008) J. Exp. Med. 205(11):2595-2608 "Tuning sensitivity to IL-4 and IL-13: differential expression of IL-4Rα, IL-13Rα1, and Yc regulates relative cytokine sensitivity".
Jyonouchi et al. (2013) Basic Mechanisms in Allergic Disease "Invariant Natural Killer T cells in children with Eosinophilic Esophagitis".
Kagami et al. (2003) Clin. Exp. Immunology 134:309-313 "Significant elevation of serum levels of eotaxin-3/CCL26, but not of eotaxin-2/CCL24, in patients with atopic dermatitis: serum eotaxin-3/CCL26 levels reflect the disease activity of atopic dermatitis".
Kakinuma et al. (2002) Clin. Exp. Immunol 127:270-273 "Serum macrophage-derived chemokine (MDC) levels are closely related with the disease activity of atopic dermatitis".
Kakinuma, Takashi et al. (2001) J. Allergy Clin. Immunol. 107(3):535-541 "Thymus and activation-regulated chemokine in atopic dermatitis: Serum thymus and activation-regulated chemokine level is closely related with disease activity".
Kakkar, Tarundeep et al. (2011) Pharmaceutical Research 28(10):2530-2542 "Population PK and IgE Pharmacodynamic Analysis of a Fully Human Monoclonal Antibody Against IL4 Receptor".
Katial (2009) Immunol Allergy Clin N Am 29:119-127 "Biomarkers for Nononcologic Gastrointestinal Disease".
Kelly and Liu (2014) World Allergy Organization Journal 7(S1):P8 "Poster 1013: IL-4R alpha antibody inhibits IgE production and airway remodeling in mouse model of house dust mite-induced eosinophilic asthma".
Kim et al. (2004) J Allergy Clin Immunol 114(6):1449-1455 "Rebound eosinophilia after treatment of hypereosinophilic syndrome and eosinophilic gastroenteritis with monoclonal anti-IL-5 antibody SCH55700".
Konikoff et al. (2006) Gastroenterology 131:1381-1391 "A Randomized, Double-Blind, Placebo-Controlled Trial of Fluticasone Propionate for Pediatric Eosinophilic Esophagitis".
Kopf et al. (1993) Letters to Nature 362:245-248 "Disruption of the murine IL-4 gene blocks Th2 cytokine responses".
Kostic et al. (2010) Clinical Immunology 135:S105-S106 "A Fully Human IL4Rα Antibody for Inhibition of IL-4/IL-13-driven TH2 Responses in Allergic Disease".
Kottyan et al. (2014) Nature Genetics "Genome-wide association analysis of eosinophilic esophagitis provides insight into the tissue specificity of this allergic disease".

Kulis et al. (2011) J. Allergy Clin Immunol 127:81-88 "Single-tree nut immunotherapy attenuates allergic reactions in mice with hypersensitivity to multiple tree nuts".
Leung et al. (2003) The New England Journal of Medicine 348:986-993 "Effect of Anti-IgE Therapy in Patients with Peanut Allergy".
Leung et al. (2004) The Journal of Clinical Investigation 113(5): 651-657 "New insights into atopic dermatitis".
Lezcano-Meza et al. (2003) Allergy 58(10):1011-1017 "Interleukin (IL)-4 and to a lesser extent either IL-13 or interferon-gamma regulate the production of eotaxin-2/CCL24 in nasal polyps".
Liacouras et al. (2011) J Allergy Clin Immunol 128(1) "Eosinophilic esophagitis: Updated consensus recommendations for children and adults".
Lin et al.(2007) Clinical Reviews in Allergy & Immunology 33(3):167-177 "Role of Bacterial Pathogens in Atopic Dermatitis".
Liu et al. (1999) Gene Therapy 6:1258-1266 "Hydrodynamics-based transfection in animals by systemic administration of plasmid DNA".
Lucendo and Sanchez-Cazalilla (2012) Expert Rev. Clin. Immunol. 8(8):733-745 "Adult versus pediatric eosinophilic esophagitis: important differences and similarities for the clinician to understand".
Ludmila and Xia (2014) World Allergy Organization Journal 7(1):P8 "Poster 1013: IL-4R alpha antibody inhibits IgE production and airway remodeling in mouse model of house dust mite-induced eosinophilic asthma".
Lwin et al. (2011) Modern Pathology 24:556-563 "Eosinophilic gastritis: histopathological characterization and quantification of the normal gastric eosinophil content".
MacCallum et al. (1996) J. Mol. Biol. 262:732-745 "Antibody-antigen Interactions: Contact Analysis and Binding Site Topography".
Maliszewski et al. (1994) Proc. Soc. Exp. Biol. Med. 206(3):233-237 "In vivo biological effects of recombinant soluble interleukin-4 receptor".
Mannon et al. (2012) GUT 61(12):1765-1773 "Interleukin 13 and its role in gut defense and inflammation".
Mariuzza et al. (1987) Ann. Rev. Biophys. Biophys. Che. 16:139-159 "The Structural Basis of Antigen-Antibody Recognition".
Martel, Britta C., et al., "Translational animal Models of Atopic Dermatitis for Preclinical Studies," Yale Journal of Biology and Medicine 90 (2017), pp. 389-402.
Masterson et al. (2011) Curr Opin Gastroenterol. 27(6):515-522 "Update on clinical and immunological features of eosinophilic gastrointestinal diseases".
Mathias, et al., "IgE-mediated systemic anaphylaxis and impaired tolerance to food antigens in mice with enhanced IL-4 receptor signaling," Journal of Allergy and Clinical Immunology, 2011, vol. 127, No. 3, 795-805, e1-e6.
Mishra and Rothenberg (2003) Gastroenterology 125:1419-1427 "Intratracheal IL-13 Induces Eosinophilic Esophagitis by an IL-5, Eotaxin-1, and STAT6-Dependent Mechanism".
Mishra et al. (2001) J Clin. Invest. 107:83-90 "An etiological role for aeroallergens and eosinophils in experimental esophagitis".
Mishra et al. (2002) The Journal of Immunology 168:2464-2469 "IL-5 Promotes Eosinophil Trafficking to the Esophagus".
Moldoveanu et al. (2009) Journal of Inflammation Research 2:1-11 "Inflammatory mechanisms in the lung".
Molfino et al. (2012) Clinical & Experimental Allergy 42(5):712-737 "Molecular and clinical rationale for therapeutic targeting of interleukin-5 and its receptor".
Morioka et al. (2009) British Journal of Dermatology 160(6): 1172-1179 "IL-4/IL-13 antagonist DNA vaccination successfully suppresses Th2 type chronic dermatitis".
Mueller, Thomas D. et al., "Structure, binding, and antagonists in the IL-4/IL-13 receptor system", Biochimica et Biophysica Acta (2002) 237-250.
Müller et al. (1993) Journal of Immunology 150:5576-5584 "Th2 cells mediate IL-4-dependent local tissue inflammation".
Nadeau et al. (2011) J. Allergy Clin. Immunol 127(6) Letters to the Editor "Rapid oral desensitization in combination with omalizumab therapy in patients with cow's milk allergy".

(56) References Cited

OTHER PUBLICATIONS

Nadeau, et al., "Oral Immunotherapy and Anti-IgE Antibody-Adjunctive Treatment for Food Allergy," Immunology and Allergy clinics of North America, 2012, vol. 32, No. 1, 111-133.
Nguyen et al. (2011) Immunological Reviews 242(1):258-271 "Immune modulation for treatment of allergic disease".
Nguyen, Tran Hoai et al., "Future Forms of Immunotherapy and Immunomodulators in Allergic Disease", Immunol Allergy Clin N Am 31 (2011); 343-365.
Niederberger (2009) Immunology Letters 122:131-133 "Allergen-specific immunotherapy".
Niranjan et al. (2013) Immunology and Cell Biology pp. 1-8 "Pathogenesis of allergen-induced eosinophilic esophagitis is independent of interleukin (IL)-13".
Noel et al. (2004) The New England Journal of Medicine 351:940-941 "Eosinophilic Esophagitis".
Novartis (2013) QAX576 "A double blinded, randomized, placebo-controlled trial of intravenous QAX576 in the treatment of eosinophilic esophagitis".
Oetjen, Landon K., et al., "Sensory Neurons Co-opt Classical Immune Signaling Pathways to Mediate Chronic Itch," Sep. 21, 2017, Cell 171, 217-228.
Oh et al. (2010) Eur Respir Rev 19(115):46-54 "Investigational therapeutics targeting the IL-4/IL-13/STAT-6 pathway for the treatment of asthma".
Ohno et al. (1985) Proc. Natl. Acad. Sci. USA 82:2945-2949 "Antigen-binding specificities of antibodies are primarily determined by seven residues of $V_H$".
Ong (2012) Expert Opinion on Emerging Drugs 17(2):129-133 "Editorial update on emerging treatments of atopic dermatitis".
Otani et al. (2013) Journal of Allergy and Clinical Immunology 131(6):1576-1582 "Anti-IL-5 therapy reduces mast cell and IL-9 cell numbers in pediatric patients with eosinophilic esophagitis".
Otulana et al. (2011) Am. J. Respir. Crit. Care Med. 183:A6179 "A Phase 2b Study of Inhaled Pitrakinra, An IL-4R/IL-13 Antagonist, Successfully Identified Responder Subpopulations of Patients with Uncontrolled Asthma".
Oyoshi et al. (2009) Advances in Immunology 102:135-226 "Cellular and Molecular Mechanisms in Atopic Dermatitis".
Paton, D. M., "Dupilumab: human monoclonal antibody against IL-4Ralpha for moderate to severe atopic dermatitis," Drugs Today, vol. 53, No. 9, Sep. 1, 2017, pp. 477-487, XP055465888.
Pesek, Robert D. et al., "Emerging drugs for eosinophilic esophagitis", Expert Opinion on Emerging Drugs, vol. 23, No. 2, Apr. 3, 2018, 12 pages.
Peserico et al. (2008) British Journal of Dermatology 158:801-807 "Reduction of relapses of atopic dermatitis with methylprednisolone aceponate cream twice weekly in addition to maintenance treatment with emollient: a multicentre, randomized, double-blind, controlled study".
Petry et al. (2012) Anais Brasileiro De Dermatologia 87(5):732-733 "Bacterial skin colonization and infections in patients with atopic dermatitis".
Prieto and Richter (2013) Curr Gastroenterol Rep 15:324 "Eosinophilic Esophagitis in Adults: an Update on Medical Management".
Prussin et al. (2009) J Allergy Clin Immunol. 124(6):1326-1332 "Eosinophilic gastrointestinal disease and peanut allergy are alternatively associated with IL-5+ and IL-5− TH2 responses".
Rafi et al. (2010) Allergy and Asthma Proceedings 31(1): 76-83 "Effects of omalizumab in patients with food allergy".
Rayapudi et al. (2010) Journal of Leukocyte Biology 88 "Indoor insect allergens are potent inducers of experimental eosinophilic esophagitis in mice".
Receptos, Inc. 2013 Annual Report.
Ring et al. (2012) J. Eur. Acad. Dermatol. Venereol. 26(8): 1045-1060 "Guidelines for treatment of atopic eczema (atopic dermatitis) Part 1".
Roitt et al. (2001) Mosby—Harcourt Publishers Limited, Immunology—Sixth Edition "Antigen Presentation" pp. 110-111.
Roll et al. (2006) J. Investig Allergol Clin Immunol 16(2):79-85 "Safety of specific immunotherapy using a four-hour ultra-rush induction scheme in bee and wasp allergy".
Romaniuk, L.I., "Allergen-specific immunotherapy: mechanisms, methods and efficacy", Clinical Immunology, Allergology and Infectology, 2012, special issue, pp. 44-47. (with English translation of the cited portion).
Rothenberg (2004) J Allergy Clin Immunol 113(1):11-28 "Eosinophilic gastrointestinal disorders (EGID)".
Rothenberg (2009) Gastroenterology 137:1238-1249 "Biology and Treatment of Eosinophilic Esophagitis".
Rothenberg, Marc E. et al., "Intravenous anti-IL-13 mAb QAX576 for the Treatment of eosinophilic esophagitis", Journal of Allergy and Clinical Immunology, vol. 135, No. 2, Feb. 1, 2015, pp. 500-507.
Rudikoff et al. (1982) Proc. Natl. Acad. Sci. 79:1979-1983 "Single amino acid substitution altering antigen-binding specificity".
Russian Official Action from Russian Federation for RU Application 2016104400, dated Oct. 6, 2017, with translation, 4 pages.
Saeki, Hidehisa, "Guidelines for Management of Atopic Dermatitis", (Advances in Medicine, Special Issue, 2009, vol. 228(1):75-79 in part), cited in the Japanese Patent Application No. 2015-531149.
Sampson et al. (2011) J. Allergy Clin Immunol. 127(5) Letters to the Editor, "A phase II, randomized, double-blind, parallel-group, placebo-controlled oral food challenge trial of Xolair (omalizumab) in peanut allergy", p. 1309-1310.
Sanofi and Regeneron Report Positive Proof-of-Concept Data for Dupilumab, an IL-4R alpha Antibody, in Atopic Dermatitis, 71st Annual Meeting of the American Academy of Dermatology (2013) http://files.shareholder.com/downloads/REGN/2689212012x0x640531/794a7e54-6904-416b-ba38-a4ccc1726852/REGN_News_2013_3_2_General_Releases.pdf.
Sanofi with Regeneron Pharmaceuticals "An Evaluation of Dupilumab in Patients with Nasal Polyposis and Chronic Symptoms of Sinusitis" Trial in Progress, Jun. 2014. ClinicalTrials.gov Identifier: NCT01920893. Retrieved from the Internet URL: http://clinicaltrials.govishow/NCT01920893 Accessed on Sep. 29, 2014.
Sanofi, "Positive Phase 2a Results of Dupilumab in Asthma in the New England Journal of Medicine," May 21, 2013, Regeneron Pharmaceuticals, Inc.
Sanofi/Regeneron Press Release, "Sanofi and Regeneron Report Positive Results with Sarilumab in First Phase 3 Rheumatoid Arthritis Registration Trial", Paris, France and Tarrytown, NY, Nov. 22, 2013, 3 pages.
Sato et al. (1993) J. Immunol. 150(7):2717-2723 "Recombinant soluble murine IL-4 receptor can inhibit or enhance IgE responses in vivo".
Scavuzzo et al. (2005) Biomedicine & Pharmacotherapy 59(6):323-9 "Inflammatory mediators and eosinophilia in atopic and non-atopic patients with nasal polyposis".
Schmidt-Weber (2012) Chem Immunol Allergy 96:120-125 "Anti-IL-4 as a New Strategy in Allergy".
Schmitt et al. (2007) J. of Allergy and Clinical Immunology 120(6):1389-1398 "What are the best outcome measurements for atopic eczema? A systematic review".
Schneider et al. (2013) J. Allergy Clin Immunol 132(6):1368-1374 "A pilot study of omalizumab to facilitate rapid oral desensitization in high-risk peanut-allergic patients".
Sekiya et al. (2002) Allergy 57:173-177 "Increased levels of a TH2-type CC chemokine thymus and activation-regulated chemokine (TARC) in serum and induced sputum of asthmatics".
Silverberg J.I., et al., "Dupilumab treatment induces rapid clinical improvement of itch in patients with moderate-to-severe atopic dermatitis" Paper presented at: American Academy of Dermatology—76th Annual Meeting; Feb. 16-20, 2018; San Diego, CA, USA.
Silverberg J.I., et al., P481, "Dupilumab treatment rapidly improves itch in patients with moderate-to-severe atopic dermatitis" An Allergy Asthma Immunol. 2017;119 (suppl 5):S95.
Simpson, E.L., et al., "Two Phase 3 Trials of Dupilumab versus Placebo in Atopic Dermatitis," The New England Journal of Medicine, Oct. 1, 2016, DOI: 10.1056/NEJMoa1610020.
Simpson, Eric L. et al., "Dupilumab therapy provides clinically meaningful improvement in patient-reported outcomes (PROs): A

(56) References Cited

OTHER PUBLICATIONS phase IIb, randomized, placebo-controlled, clinical trial in adult patients with moderate to severe atopic dermatitis (AD)", Journal of the American Academy of Dermatology, Mosby, Inc., US, vol. 75, No. 3, Jun. 4, 2016.
Simpson, Eric L. et al., "Patient burden of moderate to severe atopic dermatitis (AD): Insights from a phase 2b clinical trial of dupilumab in adults," Journal of the American Academy of Dermatology, Mosby, Inc., US, vol. 74, No. 3, Jan. 14, 2016.
Slager et al. (2012) Journal of Allergy, Asthma and Immunology 130(2):516-522.e4 "IL-4 Receptor Polymorphisms Predict Reduction in Asthma Exacerbations During Response to an Anti IL-4 Receptor Antagonist".
Spirin (1986) Vysshaya shkola, Moscow, pp. 17-23 "Molecular Biology Ribosome structure and protein biosynthesis", original Russian article and English language translation of same provided by foreign associate handling local prosecution of Russian application No. 2011120194.
Stein et al. (2006) J Allergy Clin Immunol 118(6):1312-1319 "Anti-IL-5 (mepolizumab) therapy for eosinophilic esophagitis".
Steinke and Borish (2001) Respiratory Research 2(2):1-5 "Th2 cytokines and asthma Interleukin-4: its role in the pathogenesis of asthma, and targeting it for asthma treatment with interleukin-4 receptor antagonists".
Stone et al. (2008) Clinical & Experimental Allergy 38(12):1858-1865 "Immunomodulatory therapy of eosinophil-associated gastrointestinal diseases".
Strauman (2009) Immunol Allergy Clin N Am 29:11-18 "Clinical Evaluation of the Adult who has Eosinophilic Esophagitis".
Straumann (2005) J Allergy Clin Immunol 115(2):418-419 "Eosinophilic esophagitis: Escalating epidemiology?".
Straumann et al. (2001) J Allergy Clin Immunol 108(6):954-961 "Idiopathic eosinophilic esophagitis is associated with a TH2-type allergic inflammatory response".
Straumann et al. (2009) Gut "Anti-interleukin-5 antibody treatment (mepolizumab) in active eosinophilic oesophagitis: a randomized, placebo-controlled, double-blind trial".
Tazawa et al. (2004) Arch Dermatol Res 295:459-464 "Relative importance of IL-4 and IL-13 in lesional skin of atopic dermatitis".
Tepper et al. (1990) Cell 52:457-467 "IL-4 Induces Allergic-like Inflammatory Disease and Alters T Cell Development in Transgenic Mice".
Terui, et al., "Learning from Fungus Allergy in Atopic Dermatitis Patients," Japan J. Med. Mycol, 2000, vol. 41, No. 3, 157-160.
Thaci, Diamant et al.: "Efficacy and Safety of Dupilumab in Adults with Moderate-to-Severe Atopic Dermatitis Inadequately Controlled by Topical Treatments: A Randomised, placebo-controlled, dose-ranging phase 2b trial," The Lancet, The Lancet Publishing Group, GB, vol. 387, No. 10013, Oct. 8, 2015.
Tomkinson et al. (2001) J. Immunol 166:5792-5800 "A Murine IL-4 Receptor Antagonist that Inhibits IL-4- and IL-13-induced Responses Prevents Antigen-Induced Airway Eosinophilia and Airway Hyperresponsiveness".
Tsianakas, Athanasios et al., "Dupilumab: A Milestone in the Treatment of Atopic Dermatitis," The Lancet, The Lancet Publishing Group, GB vol. 387, No. 10013, Oct. 8, 2015.
Ul-Haq, Zaheer et al., "Interleukin-4 receptor signaling and its binding mechanism: A therapeutic insight from inhibitors tool box", Cytokine & Growth Factor Review 32 (2016) 3-15.
Vajdos et al. (2002) Journal of Molecular Biology 320(2):415-428 "Comprehensive functional maps of the antigen-binding site of an anti-ErbB2 antibody obtained with shotgun scanning mutagenesis".
Vakharia, Paras P. et al., "Monoclonal Antibodies for Atopic Dermatitis: Progress and Potential", BioDrugs (2017) 31:409-422.
Veerappan et al. (2009) Clinical Gastroenterology and Hepatology 7:420-426 "Prevalence of Eosinophilic Esophagitis in an Adult Population Undergoing Upper Endoscopy: A Prospective Study".

Vestergaard et al. (2000) The Journal of Investigative Dermatology 115(4):640-646 "A $Th_2$ Chemokine, TARC, Produced by Keratinocytes May Recruit $CLA^+CCR4^+$ Lymphocytes into Lesional Atopic Dermatitis Skin".
Virchow et al. (1994) Lung 172:313-334 "Cellular and immunological markers of allergic and intrinsic bronchial asthma".
Walker et al. (1993) Clinical and Experimental Allergy 23:145-153 "Atopic dermatitis: correlation of peripheral blood T cell activation, eosinophilia and serum factors with clinical severity".
Wang and Liu (2008) Current Opinion in Immunology 20:697-702 "The IL-17 cytokine family and their role in allergic inflammation".
Wang, et al., "Peanut-induced intestinal allergy is mediated through a mast cell-IgE-FceRI-IL-13 Pathway," Journal of Allergy and Clinical Immunology, 2010, vol. 126, No. 2, 306-316, e1-e12.
Wark et al. (2006) Advanced Drug Delivery Reviews 58:657-670 "Latest technologies for the enhancement of antibody affinity".
Watson et al. (2011) Allergy, Asthma & Clinical Immunology 7:S4 "Atopic dermatitis".
Weihrauch et al. (2005) Cancer Research 65:5516-5519 "Elevated Serum Levels of CC Thymus and Activation-Related Chemokine (TARC) in Primary Hodgkin's Disease: Potential for a Prognostic Factor".
Weinbrand-Goichberg et al. (2013) Immunol Res "Eosinophilic esophagitis: an immune-mediated esophageal disease".
Wenzel et al. (2007) Lancet 370:1422-1431 "Effect of an interleukin-4 variant on late phase asthmatic response to allergen challenge in asthmatic patients: results of two phase 2a studies".
Wenzel et al. (2010) European Respiratory Society, Annual Congress 2010, "ERS—Programme" pp. 3980.
Wenzel et al. (2013) New England Journal of Medicine 368(26):2455-2466 "Dupilumab in Persistent Asthma with Elevated Eosinophil Levels".
Wershil (2009) Immunol Allergy Clin N Am 29:189-195 "Exploring the Role of Mast Cells in Eosinophilic Esophagitis".
Whalley et al. (2004) British Journal of Dermatology 150:274-283 "A new instrument for assessing quality of life in atopic dermatitis: international development of the Quality of Life Index for Atopic Dermatitis (QoLIAD)".
Wilhelm and Stockinger (2011) Frontiers in Immunology 2(68) "Innate lymphoid cells and type 2 (Th2) mediated immune responses-pathogenic or beneficial?".
Wills-Karp and Finkelman (2008) Science Signaling 1(51) "Untangling the Complex Web of IL-4 and IL-13 Mediated Signaling Pathways".
Winkler et al. (2000) J. Immunol. 165(8):4505-4514 "Changing the Antigen Binding Specificity by Single Point Mutations of an Anti-p24 (HIV-1) Antibody".
Winter and Harris (1993) Immunology Today 14(6):243-246 "Humanized Antibodies".
Wong, et al., "Guidelines for the management of atopic dermatitis (eczema) for pharmacists," CPJ/RPC, Sep./Oct. 2017, vol. 150, No. 5.
Wu et al. (1999) Journal of Molecular Biology 294:151-162 "Humanization of a murine monoclonal antibody by simultaneous optimization of framework and CDR residues".
Yamanaka et al. (2011) Curr Probl Dermatol 41:80-92 "The Role of Cytokines/Chemokines in the Pathogenesis of Atopic Dermatitis".
Yan and Shaffer (2006) World J Gastroenterol 12(15):2328-2334 "Eosinophilic esophagitis: A newly established cause of dysphagia".
Zuo et al. (2010) Journal of Immunology 185:660-669 "IL-13 Induces Esophageal Remodeling and Gene Expression by an Eosinophil-Independent, IL-13R{alpha}2-Inhibited Pathway".
Zurawski et al. (1995) J. Biol. Chem. Am. Society of Biochemical Biologists 270(23):13869-13878 "The primary binding subunit of the human Interleukin-4 receptor is also a component of the Interleukin-13 receptor".
Kopp, M.V et al., "Combination of omalizumab and specific immunotherapy is superior to immunotherapy in patients with seasonal allergic rhinoconjunctivitis and co-morbid seasonal allergic asthma", Clinical and Experimental Allergy, vol. 39, No. 2, pp. 271-279, published on Jan. 22, 2009.

(56) References Cited

OTHER PUBLICATIONS

Huang, Evie et al: "Severe Atopic Dermatitis in Children", Current Allergy and Asthma Reports, Current Science, US, vol. 18, No. 6, May 10, 2018, pp. 1-8.

Akinlade, B. et al: "Conjunctivitis in dupilumab clinical trials", British Journal of Dermatology, (Mar. 9, 2019), pp. 1-15.

Paller et al: "Early and sustained, clinically meaningful responses with dupilumab treatment in a phase 3 trial in adolescents with moderate-to-severe atopic dermatitis", Pediatric Dermatology, vol. 36, No. Suppl. 1, (Apr. 29, 2019), p. S4.

Database Embase [Online], Elsevier Science Publishers, Amsterdam, NL; (May 1, 2019), Cork M. J: "605 Efficacy and safety of dupilumab in adolescent patients with moderate-to-severe atopic dermatitis", XP002793331, Database accession No. EMB-002001809007 abstract.

Database Embase [Online], Elsevier Science Publjshers, Amsterdam, NL; (May 1, 2019), Paller, A.S.: "621 Dupilumab in adolescents with moderate-to-severe atopic dermatitis and a history of inadequate response, or intolerance to cyclosporine: subgroup analysis from a pivotal 16- week trial", XP002793332, Database accession No. EMB-002001808313, Abstract.

Regeneron 2011 Annual Report (Apr. 2011), 12 pages.

ClinicalTrials.gov archive, History of Changes for Study: NCT01548404, "Study of Dupilumab in Adult Patients with Extrinsic Moderate-to-Severe Atopic Dermatitis", (Apr. 19, 2012), 7 pages.

ClinicalTrials.gov archive, History of Changes for Study: NCT01259323, "Sequential Ascending Dose Study to Assess the Safety and Tolerability of REGN668 (SAR231893) in Patients With Atopic Dermatitis", (May 31, 2012), 6 pages.

Clinical Trials, Study NCT00676884—"A Phase Study to Investigate the Effects of Repeated Administration of AeroDerm in Subjects with Atopic Dermatitis", Aeroderm first publication of clinical study protocol in TCS resistant moderate-to-severe AD, May 13, 2008, 6 pages.

Clinical Trials, Study NCT01548404—"Study of Dupilumab in Adult Patients with Extrinsic Moderate-to-severe Atopic Dermatitis", final publication of clinical study protocol, Aug. 27, 2015, 8 pages.

Clinical Trials, Study NCT01548404—"Study of REGN668 in Adult Patients With Extrinsic Moderate-to-Severe Atopic Dermatitis", first publication of clinical study protocol, Mar. 7, 2012, 7 pages.

Clinical Trials, Study NCT01639040—"Study to Assess the Safety of REGN668 (SAR231893) Administered Concomitantly with Topical Corticosteroids (TCS) in Patients with Moderate-to-severe Atopic Dermatitis (AD)", Concomitant treatment with TCS, Jul. 11, 2012, 6 pages.

Clinical Trials Study No. NCT01312961—"Efficacy, Safety, and Tolerability of Dupilumab in Patients with Persistent Moderate to Severe Eosinophilic Asthma", In: ClinicalTrials.gov, A service of the U.S. National Institutes of Health, 10 pages, Available from: https://clinicaltrials.gov/ct2/show/NCT01312961.

Chan, L.S. et al., "Expression of Interleukin-4 in the epidermis of transgenic mice results in pruritic inflammatory skin disease: an experimental animal model to study atopic dermatitis", J. Invest. Dermatol., 2001, 117: 977-983.

Phan, N.Q. et al., "Assessment of pruritus intensity: prospective study on validity and reliability of the visual analogue scale, numeric rating scale, and verbal rating scale in 471 patients with chronic pruritis", Acta. Derm. Venereol., 2012, 92: 502-507.

Marone et al., "The Intriguing Role of Interleukin 13 in the Pathophysiology of Asthma", Frontiers in Pharmacology, 2019, pp. 1-3.

Wegmann et al., "Targeting Cytokines in Asthma therapy: could IL-37 be a Solution?", Expert Review of Respiratory Medicine, 2017, vol. 11, No. 9, pp. 675-677.

Nicodeme et al., "Esophageal Distensibility as a Measure of Disease Severity in Patients with Eosinophilic Esophagitis", Clinical Gastroenterology and Hepatology, 2013, vol. 11, No. 9, pp. 1101-1107.

De Genst, Erwin et al., "Antibody repertoire development in camelids", Developmental and Comparative Immunology, 30 (2006); 187-198.

Ward, E. Sally et al., "Blinding activities of a repertoire of single immunoglobulin variable domains secreted from *Escherichia coli*", Nature, 1989, 341:544-546.

Barthelemy, Pierre et al., "Comprehensive analysis of the factors contributing to the stability and solubility of autonomous human VH domains", Journal of Biological Chemistry, 2008, 283:3639-3654.

Choi, Yoonjoo et al., "Predicting antibody complementarity determining region structures without classification", Molecular Biosystems, 2011, 7:3327-334.

Griffiths, Andrew et al., "Human anti-self antibodies with high specificity from phage display libraries", The EMBO Journal, 1993, 12:725-734.

Klimka et al., "Human anti-CD30 recombinant antibodies by guided phage antibody selection using cell planning", British Journal of Cancer, 2000, 83:252-260.

Beiboer, Sigrid et al., "Guided selection of a pan carcinoma specific antibody reveals similar binding characteristics yet structural divergence between the original murine antibody and its human equivalent", Journal of Molecular Biology, 2000, 296:833-849.

Darsow, Ulf et al., "Pruritus and Atopic Dermatitis", Clinic Rev Allerg Immunol (2011) 41:237-244.

Buddenkotte, J. et al., "Pathophysiology and therapy of pruritis in allergic and atopic diseases", Allergy 65 (2010), 805-821.

Highlights of Prescribing Information, Dupixent(dupilumab) injection, for subcutaneous use Initial U.S. Approval: 2017, U.S. Food and Drug Administration (FDA), Revised Mar. 2017.

Regeneron: "Dupixent: Highlights of Prescribing Information", (Mar. 1, 2019), pp. 1-8, XP55610296, Retrieved from the Internet: URL: https://dlegnxy4jxlq3f.cloudfront.net/Regeneron/Dupixent_FPI.pdf, 8 pgs.

Regeneron: "Highlights of Prescribing Information See 17 for Patient Counseling Information and FDA-approved patient labeling. Revised: Mar. 2017 Full Prescribing Information: Contents 1 Indications and Usage 2 Dosage and Administration 2.1 Dosage 2.2 Important Administration Instructions 2.3 Preparation for Use", (Apr. 7, 2017), XP055534130, Retrieved from the Internet: URL: https://web.archive.org/web/20170407151633if_/https://www.regeneron.com/sites/default/files/Dupixent FPI.pdf, 4 pages.

Kwiatek, Monika et al., "Mechanical properties of the esophagus in eosinophilic esophagitis" Gastroenterology, 2011, vol. 140, No. 1, pp. 82-90.

Abe, Yasuhiko, et al., "The Diagnosis of Eosinophilic Esophagitis", (English abstract), Gastroenterological Endoscopy, Sep. 2014, vol. 56, Issue 9, pp. 3378-3393.

Mulder, DJ et al., "Understanding eosinophilic esophagitis: the cellular and molecular mechanisms of an emerging disease", Mucosal Immunology, Mar. 2011, vol. 4, No. 2, pp. 139-147.

Takashi Yoshike, "Treatment For Atopic Dermatitis", Juntendo Medical Journal, 1999, vol. 45, No. 3, pp. 352-360, 33 pages with English translation.

Manabu Fujimoto, "Oral cyclosporin therapy for atopic dermatitis", Igaku no Ayumi, Journal of Clinical and Experimental Medicine, 2009, vol. 228, No. 1, pp. 98-102, 18 pages with English translation.

Nomura, Ichiro et al., "*Staphylococcus aureus* and Atopic Dermatitis", (2000), IRYO vol. 54, No. 2, pp. 62-66, 18 pages with English translation.

Hamilton, Jennifer et al., "Dupilumab Normalizes the Eosinophilic Esophagitis Disease Transcriptome In Adult Patients With Eosinophilic Esophagitis", May 1, 2020, Abstract, retrieved from internet on Aug. 5, 2021 at: https://www.sciencedirect.com/science/article/pii/S00165085203276697via%3Dihub, 1 page.

Reed, Craig, et al., "Patient-reported outcomes in esophageal diseases", Clinical Gastroenterology and Hepatology, Elsevier, Amsterdam, NL, vol. 16. No. 3, pp. 305-310, Mar. 1, 2019.

Kim et al., "Engineering of anti-human interleukin-4 receptor alpha antibodies with potent antagonistic activity", Scientific Reports, 2019, vol. 9, Article No. 7772, pp. 1-12.

Radin et al., "First-in-Human Study of REGN668/SAR231893 (IL-4Rα mAb): Safety, Tolerability and Biomarker Results of a Randomized, Double-Blind, Placebo-Controlled, Single Ascending

(56) References Cited

OTHER PUBLICATIONS

Dose Study in Healthy Volunteers", J. Allergy Clin. Immunol., 2013, vol. 131(2), Suppl., p. AB158, (made available on Jan. 26, 2013), 2 pgs.
Siegfried et al., "Use of dupilimab in pediatric atopic dermatitis: Access, dosing, and implications for managing severe atopic dermatitis", Pediatric Dermatology, vol. 36, No. 1, Jan. 2019, pp. 172-176.
Wenzel et al. (Jul. 2, 2016) "Dupilumab efficacy and safety in adults with uncontrolled persistent asthma despite use of medium-to-high-dose inhaled corticosteroids plus a long-acting beta2 agonist: a randomised double-blind placebo-controlled pivotal phase 2b dose-ranging trial," Lancet. 388:31-44.
Waccholz et al., "Detection of Allergen-Specific IgE Antibody Responses", 2005, Journal of Immunotoxicology, 1:3-4, 189-199.
Janeway, Jr. et al., Immunobiology, 3rd Edition, 1997, Garland Publishing Inc., pp. 11:1-11:22.
Linden, Carey et al., "Analysis of allergen specific IgE cut points to cat and dog in the Childhood Allergy Study", Annals of Allergy, Asthma & Immunology, 2011, 106.2: 153-158. e2.
Yang, Eun-Seok et al., "Anti-IL-4 Receptor mAb Attenuates Allergic Airway Hyperresponsiveness (AHR) and Inflammation in Allergic Mice", J. Allergy Clin. Immunol., Poster 168, Abstracts S69, vol. 109, No. 1 (2002), 1 page.
Clinical Trials, Study NCT03682770—"Study in Pediatric Subjects With Peanut Allergy to Evaluate Efficacy and Safety of Dupilumab as Adjunct to AR10 Immunotherapy" Aug. 20, 2020, located at: URL:https://clinicaltrials.gov/ct2/history/NCT03682770?V_8=View#StudyPageTop, (retrieved on Mar. 10, 2022), 7 pages.
Corren, Jonathan et al., "Short-term subcutaneous allergy immunotherapy and dupilumab are well-tolerated in allergic rhinitis: A randomized trial", Journal of Asthma and Allergy, vol. 14, Aug. 16, 2021, pp. 1045-1063.
Bruton, Kelly et al., "Interrupting reactivation of immunologic memory diverts the allergic response and prevents anaphylaxis", Journal of Allergy and Clinical Immunology, vol. 147, No. 4, Dec. 15, 2020, pp. 1381-1392.
Wambre, ER, "Baseline characteristics of peanut-allergic individuals during the dupilumab as adjunct to AR101 clinical trial", Abstract, retrieved at: https://onlinelibrary.wiley.com/doi/10.1111/all.14506, Sep. 7, 2020, 1 page.
Chaker, Adam et al., "Short-term subcutaneous grass pollen immunotherapy under the umbrella of anti-IL-4: A randomized controlled trial". Journal of Allergy and Clinical Immunology, vol. 137, No. 2, Oct. 31, 2015, 19 pages.
Corren, J. et al., "Effects of combined treatment with allergen immunotherapy and dupilumab on nasal allergen challenge and tolerability in immunotherapy", Allergy, Jun. 6, 2020, p. 78.
Regeneron Pharmaceuticals et al., "Dupilumab As An Adjunct for Subcutaneous Grass Immunotherapy", May 11, 2020, retrieved from Internet at: https://clinicaltrials.gov/ct2/history/NCT03558997?V_5=View#StudyPageTop, retrieved on Oct. 20, 2020, 46 pgs.
Regeneron Pharmaceuticals et al., "Dupilumab As An Adjunct for Subcutaneous Grass Immunotherapy", Jun. 26, 2019, retrieved from Internet at: https://clinicaltrials.gov/ct2/history/NCT03558997?A=4&B=4&C=merged#StudyPageTop, retrieved on Oct. 20, 2020, 10 pgs.
Schmid, J.M. et al., "Basophil Sensitivity Decreases During the Updosing on SCIT in Subjects Allergic to Grass Pollen", Journal of Allergy and Clinical Immunology, vol. 127, No. S2, Feb. 1, 2011, p. AB203.
"AR101 Oral Immunotherapy for Peanut Allergy", N. Eng J Med 2018; 379; 1991-2001, located online on Jan. 24, 2023 at: https:///www.nejm.org/doi/full/10.1056/nejmoa1812856, 20 pages.
NCT03682770, USNLM (U.S. National Library of Medicine), History of Changes for Study, NCT03682770: Study in Pediatric Subjects With Peanut Allergy to Evaluate Efficacy and Safety of Dupilumab as Adjunct to AR101 (Peanut Oral Immunotherapy), https:clinicaltrials.gov/ct2/history/NCT03682770?V_4=View, 2019, 7 pages.
Hill, Robert et al., "Comparison of drug delivery with autoinjector versus manual prefilled syringe and between three different autoinjector devices administered in pig thigh", Med Devices (Auckl), 2016, 9; 257-266, pub. Online Aug. 2, 2016, doi: 10.2147/MDER.S83406.
Supplementary Appendix, Supplement to: AR101 Oral Immunotherapy for Peanut Allergy, N Engl J Med 2018, 379; 1991-2001, DOI: 10.1056/NEJMoa1812856, 2018, last updated Mar. 7, 2019, 23 pages.
Guidelines for the Prevention and Treatment of Allergic Diseases, Xixin Yan and Jitao Guan as editors-in-chief, Shijiazhuang: Hebei Science and Technology Press, relevant pp. 252-254, published in May 2009, with English translation of pp. 252-254, numbered pp. 1-4).
Nicholson, G. C. et al., "The effects of an anti-IL-13 mAB on cytokine levels and nasal symptoms following nasal allergen challenge", 2011, J. Allergy Clin Immunol., 128(4), pp. 800-807, 17 pgs all together.
The American Academy of Allergy, Asthma, and Immunology, "The Current State of Oral Immunotherapy", retrieved from: https://www.aaaai.org/tools-for-the-public/conditions-library/allergies/the-current-state-or-oral-immunotherapy), Year: reviewed Feb. 4, 2020, 5 pages.
Sheldon, J. et al., "Allergy Diagnosis Reference Guide", Est Kent Hospitals University, Clinical Biochemistry, retrieved from: https://www.mtw.nhs.uk/wp/content/uploads/2015/08/Allergy_diagnosis_reference_guide.pdf, Oct. 2014, 10 pages.
Wang, J. et al., "0056 Baseline peanut-specific IgE potentially predicts up-dose completion and treatment response with AR10 in CODIT", Annals of Allergy, Asthma & Immunology, vol. 17, Issue 5, Supplemental, Nov. 2016, p. S18, 2 pages.
Parrish, Chris, "Management of Peanut Allergy: A Focus on Novel Immunotherapies", ALMC, 2018; vol. 24, Issue 19, SO, retrieved from: https://ajmc.com/view/management-of-peanut-allergy-a-focus-on-novel-immunotherapies, Oct. 19, 2018, 25 pages.
Fujieda, Shigeharu et al., "Biomarkers in Allergic Rhinitis", Allergy, 2013, vol. 62, No. 5, pp. 523-531, with English translation (12 pages).
Nelson, M.R. et al., "Standardized Grass Allergen Extract Prescribing Practices in a Large Healthcare System", Journal of Allergy and Clinical Immunology, Abstract 486, Feb. 2008, vol. 121, Issue 2, Supplement 1, p. S126.

* cited by examiner

US 11,964,016 B2

SEQUENCE LISTING

```
<160> NUMBER OF SEQ ID NOS: 44

<210> SEQ ID NO 1
<211> LENGTH: 124
<212> TYPE: PRT
<213> ORGANISM: Artificial Sequence
<220> FEATURE:
<223> OTHER INFORMATION: Dupilumab HCVR

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: Dupilumab LCVR

<400> SEQUENCE: 2
```

```
Asp Ile Val Met Thr Gln Ser Pro Leu Ser Leu Pro Val Thr Pro Gly
1               5                  10                 15

Glu Pro Ala Ser Ile Ser Cys Arg Ser Ser Gln Ser Leu Leu Tyr Ser
            20                  25                 30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 3
<211> LENGTH: 8
<212> TYPE: PRT
<213> ORGANISM: Artificial Sequence
<220> FEATURE:
<223> OTHER INFORMATION: Dupilumab HCDR1

<400> SEQUENCE: 3

```
Gly Phe Thr Phe Arg Asp Tyr Ala
1               5
```

<210> SEQ ID NO 4
<211> LENGTH: 8
<212> TYPE: PRT
<213> ORGANISM: Artificial Sequence
<220> FEATURE:
<223> OTHER INFORMATION: Dupilumab HCDR2

<400> SEQUENCE: 4

```
Ile Ser Gly Ser Gly Gly Asn Thr
1               5
```

<210> SEQ ID NO 5
<211> LENGTH: 18
<212> TYPE: PRT
<213> ORGANISM: Artificial Sequence
<220> FEATURE:
<223> OTHER INFORMATION: Dupilumab HCDR3

<400> SEQUENCE: 5

```
Ala Lys Asp Arg Leu Ser Ile Thr Ile Arg Pro Arg Tyr Tyr Gly Leu
1               5                   10                  15

Asp Val
```

<210> SEQ ID NO 6
<211> LENGTH: 11
<212> TYPE: PRT
<213> ORGANISM: Artificial Sequence
<220> FEATURE:
<223> OTHER INFORMATION: Dupilumab LCDR1

<400> SEQUENCE: 6

```
Gln Ser Leu Leu Tyr Ser Ile Gly Tyr Asn Tyr
1               5                   10
```

<210> SEQ ID NO 7
<211> LENGTH: 3
<212> TYPE: PRT

-continued

```
<213> ORGANISM: Artificial Sequence
<220> FEATURE:
<223> OTHER INFORMATION: Dupilumab LCDR2

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: Dupilumab LCDR3

<400> SEQUENCE: 8

Met Gln Ala Leu Gln Thr Pro Tyr Thr
1               5

<210> SEQ ID NO 9
<211> LENGTH: 451
<212> TYPE: PRT
<213> ORGANISM: Artificial Sequence
<220> FEATURE:
<223> OTHER INFORMATION: Dupilumab HC

<400> SEQUENCE: 9

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Asp Val Ser
        260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450

<210> SEQ ID NO 10
<211> LENGTH: 219
<212> TYPE: PRT
<213> ORGANISM: Artificial Sequence
<220> FEATURE:
<223> OTHER INFORMATION: Dupilumab LC

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 11
<211> LENGTH: 375
<212> TYPE: DNA
<213> ORGANISM: Artificial Sequence
<220> FEATURE:
<223> OTHER INFORMATION: synthetic

<400> SEQUENCE: 11
gaggtgcagc tggtggagtc tggggggaggc ttggtccagc ctgggggtc cctgagactc    60 tcctgtgcag cctctggatt cacctttagt aacttttgga tgacctgggt ccgccaggct   120
ccagggaagg gcctggagtg ggtggccaac atgaaccaag atggaagtga aaatactat    180 gtggactctg tgaagggccg attcaccatc tccagagaca cgccaagag ctcactgtat    240 ctgcaaatga acagcctgag agccgaggac acggctgtgt attactgtgc gagagatcgg   300
gaatattgta ttagtaccag ctgctatgat gactttgact actggggcca gggaaccctg   360
gtcaccgtct cctca                                                    375

<210> SEQ ID NO 12
<211> LENGTH: 125
<212> TYPE: PRT
<213> ORGANISM: Artificial Sequence
<220> FEATURE:
<223> OTHER INFORMATION: synthetic

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Trp Met Thr Trp Val Arg Gln Ala Pro Gly Lys Gly Leu Glu Trp Val
            35                  40                  45

Ala Asn Met Asn Gln Asp Gly Ser Glu Lys Tyr Tyr Val Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Glu Tyr Cys Ile Ser Thr Ser Cys Tyr Asp Asp Phe
            100                 105                 110

Asp Tyr Trp Gly Gln Gly Thr Leu Val Thr Val Ser Ser
            115                 120                 125

<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
ggattcacct ttagtaactt ttgg                                            24

<210> SEQ ID NO 14
<211> LENGTH: 8
<212> TYPE: PRT
<213> ORGANISM: Artificial Sequence
<220> FEATURE:
<223> OTHER INFORMATION: synthetic

<400> SEQUENCE: 14

Gly Phe Thr Phe Ser Asn Phe Trp
1               5

<210> SEQ ID NO 15
<211> LENGTH: 24
<212> TYPE: DNA
<213> ORGANISM: Artificial Sequence
<220> FEATURE:
<223> OTHER INFORMATION: synthetic

<400> SEQUENCE: 15
atgaaccaag atggaagtga gaaa                                            24

<210> SEQ ID NO 16
<211> LENGTH: 8
<212> TYPE: PRT
<213> ORGANISM: Artificial Sequence
<220> FEATURE:
<223> OTHER INFORMATION: synthetic

<400> SEQUENCE: 16

Met Asn Gln Asp Gly Ser Glu Lys
1               5

<210> SEQ ID NO 17
<211> LENGTH: 54
<212> TYPE: DNA
<213> ORGANISM: Artificial Sequence
<220> FEATURE:
<223> OTHER INFORMATION: synthetic

<400> SEQUENCE: 17
gcgagagatc gggaatattg tattagtacc agctgctatg atgactttga ctac           54

<210> SEQ ID NO 18
<211> LENGTH: 18
<212> TYPE: PRT
<213> ORGANISM: Artificial Sequence
<220> FEATURE:
<223> OTHER INFORMATION: synthetic

<400> SEQUENCE: 18

Ala Arg Asp Arg Glu Tyr Cys Ile Ser Thr Ser Cys Tyr Asp Asp Phe
1               5                   10                  15

Asp Tyr

<210> SEQ ID NO 19
<211> LENGTH: 324
<212> TYPE: DNA
<213> ORGANISM: Artificial Sequence
<220> FEATURE:
<223> OTHER INFORMATION: synthetic

<400> SEQUENCE: 19

```
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta ccccctccgat caccttcggc    300 caagggacac gactggagat taaa                                           324
```

```
<210> SEQ ID NO 20
<211> LENGTH: 108
<212> TYPE: PRT
<213> ORGANISM: Artificial Sequence
<220> FEATURE:
<223> OTHER INFORMATION: synthetic

<400> SEQUENCE: 20
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

```
<210> SEQ ID NO 21
<211> LENGTH: 18
<212> TYPE: DNA
<213> ORGANISM: Artificial Sequence
<220> FEATURE:
<223> OTHER INFORMATION: synthetic

<400> SEQUENCE: 21
cagagcatta gcagctat                                                   18

<210> SEQ ID NO 22
<211> LENGTH: 6
<212> TYPE: PRT
<213> ORGANISM: Artificial Sequence
<220> FEATURE:
<223> OTHER INFORMATION: synthetic

<400> SEQUENCE: 22
```

Gln Ser Ile Ser Ser Tyr
1               5

```
<210> SEQ ID NO 23
<211> LENGTH: 9
<212> TYPE: DNA
<213> ORGANISM: Artificial Sequence
<220> FEATURE:
<223> OTHER INFORMATION: synthetic

<400> SEQUENCE: 23 gctgcatcc                                                              9
```

-continued

<210> SEQ ID NO 24
<211> LENGTH: 3
<212> TYPE: PRT
<213> ORGANISM: Artificial Sequence
<220> FEATURE:
<223> OTHER INFORMATION: synthetic

<400> SEQUENCE: 24

Ala Ala Ser
1

<210> SEQ ID NO 25
<211> LENGTH: 30
<212> TYPE: DNA
<213> ORGANISM: Artificial Sequence
<220> FEATURE:
<223> OTHER INFORMATION: synthetic

<400> SEQUENCE: 25
caacagagtt acagtacccc tccgatcacc                                      30

<210> SEQ ID NO 26
<211> LENGTH: 10
<212> TYPE: PRT
<213> ORGANISM: Artificial Sequence
<220> FEATURE:
<223> OTHER INFORMATION: synthetic

<400> SEQUENCE: 26

Gln Gln Ser Tyr Ser Thr Pro Pro Ile Thr
1               5                   10

<210> SEQ ID NO 27
<211> LENGTH: 372
<212> TYPE: DNA
<213> ORGANISM: Artificial Sequence
<220> FEATURE:
<223> OTHER INFORMATION: synthetic

<400> SEQUENCE: 27
gaagtacagc ttgtagaatc cggcggagga ctggtacaac tggaagaag tcttagactg       60 agttgcgcag ctagtgggtt tacattcgac gattacagca tgcattgggt gaggcaagct    120
cctggtaaag gattgaatg ggttagcggg atatcatgga actcaggaag caagggatac    180
gccgacagcg tgaaaggccg atttacaata tctagggaca cgcaaaaaa ctctctctac    240 cttcaaatga actctcttag ggcagaagac acagcattgt attattgcgc aaaatacggc    300
agtggttatg gcaagttta tcattatgga ctggacgtgt ggggacaagg gacaacagtg    360
acagtgagta gc                                                         372

<210> SEQ ID NO 28
<211> LENGTH: 124
<212> TYPE: PRT
<213> ORGANISM: Artificial Sequence
<220> FEATURE:
<223> OTHER INFORMATION: synthetic

<400> SEQUENCE: 28

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
         35                  40                  45

Ser Gly Ile Ser Trp Asn Ser Gly Ser Lys Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Tyr Gly Ser Gly Tyr Gly Lys Phe Tyr His Tyr Gly Leu Asp
             100                 105                 110

Val Trp Gly Gln Gly Thr Thr Val Thr Val Ser Ser
         115                 120

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
gggtttacat tcgacgatta cagc                                    24

<210> SEQ ID NO 30
<211> LENGTH: 8
<212> TYPE: PRT
<213> ORGANISM: Artificial Sequence
<220> FEATURE:
<223> OTHER INFORMATION: synthetic

<400> SEQUENCE: 30

Gly Phe Thr Phe Asp Asp Tyr Ser
1               5

<210> SEQ ID NO 31
<211> LENGTH: 24
<212> TYPE: DNA
<213> ORGANISM: Artificial Sequence
<220> FEATURE:
<223> OTHER INFORMATION: synthetic

<400> SEQUENCE: 31
atatcatgga actcaggaag caag                                    24

<210> SEQ ID NO 32
<211> LENGTH: 8
<212> TYPE: PRT
<213> ORGANISM: Artificial Sequence
<220> FEATURE:
<223> OTHER INFORMATION: synthetic

<400> SEQUENCE: 32

Ile Ser Trp Asn Ser Gly Ser Lys
1               5

<210> SEQ ID NO 33
<211> LENGTH: 51
<212> TYPE: DNA
<213> ORGANISM: Artificial Sequence
<220> FEATURE:
<223> OTHER INFORMATION: synthetic

<400> SEQUENCE: 33
gcaaaatacg gcagtggtta tggcaagttt tatcattatg gactggacgt g         51

<210> SEQ ID NO 34
<211> LENGTH: 17
<212> TYPE: PRT
<213> ORGANISM: Artificial Sequence
<220> FEATURE:
<223> OTHER INFORMATION: synthetic

<400> SEQUENCE: 34

```
Ala Lys Tyr Gly Ser Gly Tyr Gly Lys Phe Tyr His Tyr Gly Leu Asp
1               5                   10                  15

Val
```

<210> SEQ ID NO 35
<211> LENGTH: 372
<212> TYPE: DNA
<213> ORGANISM: Artificial Sequence
<220> FEATURE:
<223> OTHER INFORMATION: synthetic

<400> SEQUENCE: 35

```
gaagtacagc ttgtagaatc cggcggagga ctggtacaac ctggaagaag tcttagactg    60
agttgcgcag ctagtgggtt tacattcgac gattacagca tgcattgggt gaggcaagct   120
cctggtaaag gattgaatgg gttagcggg atatcatgga actcaggaag catcggatac   180
gccgacagcg tgaaaggccg atttacaata tctaggggaca acgcaaaaaa ctctctctac   240
cttcaaatga actctcttag ggcagaagac acagcattgt attattgcgc aaaatacggc   300
agtggttatg gcaagttta ttattatgga atggacgtgt ggggacaagg gacaacagtg   360
acagtgagta gc                                                       372
```

<210> SEQ ID NO 36
<211> LENGTH: 124
<212> TYPE: PRT
<213> ORGANISM: Artificial Sequence
<220> FEATURE:
<223> OTHER INFORMATION: synthetic

<400> SEQUENCE: 36

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120
```

<210> SEQ ID NO 37
<211> LENGTH: 24
<212> TYPE: DNA
<213> ORGANISM: Artificial Sequence

```
<220> FEATURE:
<223> OTHER INFORMATION: synthetic

<400> SEQUENCE: 37
gggtttacat tcgacgatta cagc                                          24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Gly Phe Thr Phe Asp Asp Tyr Ser
1               5

<210> SEQ ID NO 39
<211> LENGTH: 24
<212> TYPE: DNA
<213> ORGANISM: Artificial Sequence
<220> FEATURE:
<223> OTHER INFORMATION: synthetic

<400> SEQUENCE: 39
atatcatgga actcaggaag catc                                          24

<210> SEQ ID NO 40
<211> LENGTH: 8
<212> TYPE: PRT
<213> ORGANISM: Artificial Sequence
<220> FEATURE:
<223> OTHER INFORMATION: synthetic

<400> SEQUENCE: 40

Ile Ser Trp Asn Ser Gly Ser Ile
1               5

<210> SEQ ID NO 41
<211> LENGTH: 51
<212> TYPE: DNA
<213> ORGANISM: Artificial Sequence
<220> FEATURE:
<223> OTHER INFORMATION: synthetic

<400> SEQUENCE: 41
gcaaaatacg gcagtggtta tggcaagttt tattattatg gaatggacgt g            51

<210> SEQ ID NO 42
<211> LENGTH: 17
<212> TYPE: PRT
<213> ORGANISM: Artificial Sequence
<220> FEATURE:
<223> OTHER INFORMATION: synthetic

<400> SEQUENCE: 42

Ala Lys Tyr Gly Ser Gly Tyr Gly Lys Phe Tyr Tyr Tyr Gly Met Asp
1               5                   10                  15
Val

<210> SEQ ID NO 43
<211> LENGTH: 117
<212> TYPE: PRT
<213> ORGANISM: Artificial Sequence
<220> FEATURE:
<223> OTHER INFORMATION: R1103 HCVR
```

-continued

```
<400> SEQUENCE: 43

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asp Tyr
            20                  25                  30

Asn Ile His Trp Val Lys Gln Ser His Gly Lys Ser Leu Glu Trp Ile
        35                  40                  45

Gly Tyr Ile Tyr Pro Asn Asn Gly Asp Asn Gly Tyr Asn Gln Lys Phe
    50                  55                  60

Arg Gly Lys Ala Thr Leu Thr Val Asp Lys Ser Ser Ser Thr Ala Tyr
65                  70                  75                  80

Met Glu Leu Arg Ser Leu Thr Ser Asp Asp Ser Ala Val Tyr Tyr Cys
                85                  90                  95

Ala Arg Gly Arg Leu Arg Tyr Phe Asp Val Trp Gly Thr Gly Thr Thr
            100                 105                 110

Val Thr Val Ser Ser
            115

<210> SEQ ID NO 44
<211> LENGTH: 111
<212> TYPE: PRT
<213> ORGANISM: Artificial Sequence
<220> FEATURE:
<223> OTHER INFORMATION: R1103 LCVR

<400> SEQUENCE: 44

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly His Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Leu Asp
65                  70                  75                  80

Pro Val Glu Ala Asp Asp Ala Ala Thr Tyr Tyr Cys Gln Gln Tyr Asn
                85                  90                  95

Glu Asp Pro Pro Thr Phe Gly Ser Gly Thr Lys Leu Glu Ile Lys
            100                 105                 110
```

COMBINATION OF IL-4/IL-13 PATHWAY INHIBITORS AND PLASMA CELL ABLATION FOR TREATING ALLERGY

CROSS-REFERENCE TO RELATED APPLICATIONS

This application claims priority to U.S. Provisional Patent Application Nos. 62/822,022, filed Mar. 21, 2019, and 62/957,550, filed Jan. 6, 2020, the entire content of each of which is incorporated by reference herein.

SEQUENCE STATEMENT

The instant application contains a Sequence Listing, which has been submitted electronically in ASCII format and is hereby incorporated by reference in its entirety. Said ASCII copy, created on Mar. 20, 2020, is named SequenceList_10581USU1.TXT and is 22 kilobytes in size.

FIELD OF THE INVENTION

The present disclosure relates to methods for treating allergy comprising administering to a subject in need thereof a therapeutically effective amount of an IL-4/IL-13 pathway inhibitor in combination with a therapeutically effective amount of a plasma cell ablating agent.

BACKGROUND

Allergies and allergic diseases are serious medical conditions with consequences ranging from non-life-threatening responses that resolve over time to life-threatening effects such as anaphylaxis. Allergic reactions can result from contact or exposure to a variety of products such as certain food items, insect venom, plant-derived material (e.g., pollen), chemicals, drugs/medications, and animal dander. The pathophysiology of allergy is influenced by a complex interplay between Immunoglobulin E (IgE)-mediated sensitization, the immune system, and environmental factors. Current treatment options for allergies include avoidance, pharmacological symptom treatment and prophylaxis using allergen-specific immunotherapies (SIT). Unfortunately, these current treatment strategies are often inadequate, costly, impractical or involve significant risk. For example, avoidance of allergen is not always possible and can negatively impact on patient and caregiver quality of life. Immunotherapeutic approaches, on the other hand, involve deliberate administration of allergen to susceptible individuals and are therefore inherently risky with the potential for unwanted severe allergic reactions or anaphylaxis. Accordingly, an unmet need exists in the art for novel therapeutic approaches that prevent or treat allergies or allergic responses and reduce the risk of developing an allergic response.

SUMMARY

In one aspect, the present disclosure provides methods for treating an allergy, allergic reaction, or allergic disorder, for preventing or reducing the severity of an allergic reaction, or for reducing or eliminating allergen-specific serum IgE in a subject. In some embodiments, the method comprises administering to a subject (e.g., a subject having an allergy, an allergic disorder, a mast cell activation disorder, or mastocytosis) an IL-4/IL-13 pathway inhibitor and a plasma cell ablating agent.

In certain embodiments, the present disclosure includes methods of treating allergy or preventing or reducing the severity of an allergic reaction, comprising: (a) selecting a subject with an allergic disease or disorder, a mast cell activation disorder or mastocytosis; and (b) administering to the subject in need thereof a therapeutically effective amount of an IL-4/IL-13 pathway inhibitor and a therapeutically effective amount of a plasma cell ablating agent.

In certain embodiments, the present disclosure includes methods of treating allergy or preventing or reducing the severity of an allergic reaction, comprising: (a) selecting a subject with an allergic disease or disorder, a mast cell activation disorder, or mastocytosis; and (b) administering to the subject in need thereof a therapeutically effective amount of an IL-4/IL-13 pathway inhibitor and a plasma cell ablating agent.

In certain embodiments, the present disclosure includes methods for treating allergy or preventing or reducing the severity of an allergic reaction, comprising: (a) selecting a subject with an allergic disease or disorder, a mast cell activation disorder, or mastocytosis, wherein the subject is on a background therapy regimen comprising one or more doses on an IL-4/IL-13 pathway inhibitor; and (b) administering at least one dose of a plasma cell ablating agent.

In one embodiment, the administration of the IL-4/IL-13 pathway inhibitor prevents generation of new IgE+ plasma cells and the administration of the plasma cell ablating agent leads to elimination of bone marrow-resident IgE+ plasma cells, thus eliminating allergen-specific serum IgE.

In certain embodiments, the present disclosure includes methods for increasing the efficacy and/or tolerability of an immunotherapy regimen in a subject having an allergy. In some embodiments, the method comprises administering to the subject an IL-4/IL-13 pathway inhibitor and a plasma cell ablating agent prior to or concurrent with the immunotherapy regimen. In some embodiments, the immunotherapy regimen is an oral immunotherapy (OIT) regimen. In some embodiments, the immunotherapy regimen is a subcutaneous immunotherapy (SCIT) regimen. In some embodiments, the immunotherapy is an allergen-specific immunotherapy regimen for a food allergen (e.g., a peanut allergen). In some embodiments, the immunotherapy is an allergen-specific immunotherapy regimen for an environmental allergen.

In one embodiment of the methods disclosed herein, the allergic disease or disorder is selected from the group consisting of allergic asthma, hay fever, chronic urticaria, food allergy, pollen allergy, and allergy due to an environmental allergen. In one embodiment, the subject is at a risk of anaphylaxis due to an allergen. In one embodiment, the subject has seasonal allergy. In one embodiment, the subject has a severe allergy. In one embodiment, the subject has an allergy due to one or more allergens selected from the group consisting of milk, a dairy product, egg, celery, sesame, wheat, meat, fruit, soy, fish, shellfish, a sugar, peanuts, a legume, a tree nut, dust, dust mite, pollen, insect venom, mold, animal fur, animal dander, wool, latex, a metal, a household cleaner, a detergent, medication, cosmetics, perfumes, a drug such as penicillin, sulfonamides, or salicylate, therapeutic monoclonal antibodies (e.g., cetuximab), ragweed, grass and birch. In one embodiment, the allergen is contained in a food item selected from the group consisting of milk, a dairy product, egg, celery, sesame, wheat, meat, fruit, soy, fish, shellfish, a sugar, peanuts, a legume, and a tree nut. In one embodiment, the allergen is a non-food allergen selected from the group consisting of dust, dust mite, pollen, insect venom, mold, animal fur, animal dander, wool, latex, a metal, a household cleaner, a detergent, medication, cosmetics, perfumes, a drug such as penicillin, sulfonamides, or salicylate, therapeutic monoclonal antibodies (e.g., cetuximab), ragweed, grass and birch.

In one embodiment of the methods disclosed herein, the IL-4/IL-13 pathway inhibitor is selected from the group consisting of an anti-IL-4 antibody, an anti-IL-13 antibody, an anti-IL-4/IL-13 bispecific antibody, an IL-4 receptor (IL-4R) inhibitor, an IL-4 trap, an IL-13 trap, and an anti-IL-4R antibody. In one embodiment, the IL-4/IL-13 pathway inhibitor is an anti-IL-4 antibody (e.g., pascolizumab). In another embodiment, the IL-4/IL-13 pathway inhibitor is an anti-IL-13 antibody (e.g., tralokinumab, lebrikizumab, dectrekumab, GSK679586, or MEDI7836). In another embodiment, the IL-4/IL-13 pathway inhibitor is an anti-IL-4/IL-13 bispecific antibody (e.g., romilkimab). In another embodiment, the IL-4/IL-13 pathway inhibitor is an IL-4R inhibitor (e.g., an IL-4 mutein such as pitrakinra or an anti-IL-4R antibody). In another embodiment, the IL-4/IL-13 pathway inhibitor is an anti-IL-4R antibody. In another embodiment, the IL-4/IL-13 pathway inhibitor is an IL-4 trap or IL-13 trap.

In one embodiment, the IL-4/IL-13 pathway inhibitor is an anti-IL-4R antibody or an antigen-binding fragment thereof. In one embodiment, the anti-IL-4R antibody comprises a heavy chain variable region (HCVR) that includes three heavy chain complementarity determining regions (CDRs) (HCDR1, HCDR2 and HCDR3) and a light chain variable region (LCVR) that includes three light chain CDRs (LCDR1, LCDR2 and LCDR3), wherein: HCDR1 has an amino acid sequence of SEQ ID NO: 3; HCDR2 has an amino acid sequence of SEQ ID NO: 4; HCDR3 has an amino acid sequence of SEQ ID NO: 5; LCDR1 has an amino acid sequence of SEQ ID NO: 6; LCDR2 has an amino acid sequence of SEQ ID NO: 7; and LCDR3 has an amino acid sequence of SEQ ID NO: 8. In another embodiment, the anti-IL-4R antibody includes a heavy chain variable region (HCVR) comprising the amino acid sequence of SEQ ID NO: 1 and a light chain variable region (LCVR) comprising the amino acid sequence of SEQ ID NO: 2. In another embodiment, the anti-IL-4R antibody includes a heavy chain and a light chain, wherein the heavy chain has an amino acid sequence of SEQ ID NO: 9. In another embodiment, the anti-IL-4R antibody includes a heavy chain and a light chain, wherein the light chain has an amino acid sequence of SEQ ID NO: 10. In another embodiment, the anti-IL-4R antibody includes a heavy chain and a light chain, wherein the heavy chain has an amino acid sequence of SEQ ID NO: 9 and the light chain has an amino acid sequence of SEQ ID NO: 10. In another embodiment, the IL-4/IL-13 pathway inhibitor is dupilumab or a bioequivalent thereof. In another embodiment, the IL-4/IL-13 pathway inhibitor is selected from the group consisting of dupilumab, pascolizumab, AMG317, MEDI2045, MEDI9314, tralokinumab, lebrikzimab, anrukinzumab, dectrekumab, GSK679586, MEDI7836, romilkimab, an IL-4 trap, an IL-13 trap, AER-003, and pitrakinra.

In one embodiment of the methods disclosed herein, the plasma cell ablating agent is selected from the group consisting of a B-cell maturation antigen (BCMA) targeting agent, a proteasome inhibitor, a histone deacetylase inhibitor, a B-cell activating factor (BAFF) inhibitor, and an inhibitor of A proliferation inducing ligand (APRIL; CD256). In one embodiment, the BCMA targeting agent is selected from the group consisting of an anti-BCMA/anti-CD3 bispecific antibody, a chimeric antigen receptor against BCMA, and an anti-BCMA antibody conjugated to a cytotoxic drug.

In one embodiment, the plasma cell ablating agent is an anti-BCMA/anti-CD3 bispecific antibody or antigen-binding fragment thereof comprising (a) a first antigen-binding domain that specifically binds to BCMA; and (b) a second antigen-binding domain that specifically binds CD3. In one embodiment, the first antigen-binding domain comprises three heavy chain CDRs (HCDR1, HCDR2 and HCDR3) contained with a heavy chain variable region (HCVR) comprising the amino acid sequence of SEQ ID NO: 12; and three light chain CDRs (LCDR1, LCDR2 and LCDR3) contained with a light chain variable region (LCVR) comprising the amino acid sequence of SEQ ID NO: 20. In a further embodiment, HCDR1 has an amino acid sequence of SEQ ID NO: 14; HCDR2 has an amino acid sequence of SEQ ID NO: 16; HCDR3 has an amino acid sequence of SEQ ID NO: 18; LCDR1 has an amino acid sequence of SEQ ID NO: 22; LCDR2 has an amino acid sequence of SEQ ID NO: 24; and LCDR3 has an amino acid sequence of SEQ ID NO: 26. In another embodiment, the second antigen-binding domain comprises three heavy chain CDRs (HCDR1, HCDR2 and HCDR3) contained with a heavy chain variable region (HCVR) comprising the amino acid sequence selected from the group consisting of SEQ ID NOs: 28 and 36; and three light chain CDRs (LCDR1, LCDR2 and LCDR3) contained with a light chain variable region (LCVR) comprising the amino acid sequence of SEQ ID NO: 20. In a further embodiment, HCDR1 has an amino acid sequence of SEQ ID NO: 30 or 38; HCDR2 has an amino acid sequence of SEQ ID NO: 32 or 40; HCDR3 has an amino acid sequence of SEQ ID NO: 34 or 42; LCDR1 has an amino acid sequence of SEQ ID NO: 22; LCDR2 has an amino acid sequence of SEQ ID NO: 24; and LCDR3 has an amino acid sequence of SEQ ID NO: 26. In one embodiment, the anti-BCMA/anti-CD3 bispecific antibody comprises: (a) a first antigen-binding domain that binds specifically to BCMA and that comprises three heavy chain CDRs and three light chain CDRs wherein the six CDRs HCDR1-HCDR2-HCDR3-LCDR1-LCDR2-LCDR3 comprise the amino acid sequences of SEQ ID NOs: 14-16-18-22-24-26; and (b) a second antigen-binding domain that binds specifically to CD3 and that comprises three heavy chain CDRs and three light chain CDRs wherein the six CDRs HCDR1-HCDR2-HCDR3-LCDR1-LCDR2-LCDR3 comprise the amino acid sequences of SEQ ID NOs: 30-32-34-22-24-26. In one embodiment, the anti-BCMA/anti-CD3 bispecific antibody comprises: (a) a first antigen-binding domain that binds specifically to BCMA and that comprises three heavy chain CDRs and three light chain CDRs wherein the six CDRs HCDR1-HCDR2-HCDR3-LCDR1-LCDR2-LCDR3 comprise the amino acid sequences of SEQ ID NOs: 14-16-18-22-24-26; and (b) a second antigen-binding domain that binds specifically to CD3 and that comprises three heavy chain CDRs and three light chain CDRs wherein the six CDRs HCDR1-HCDR2-HCDR3-LCDR1-LCDR2-LCDR3 comprise the amino acid sequences of SEQ ID NOs: 38-40-42-22-24-26. In one embodiment, the anti-BCMA/anti-CD3 bispecific antibody comprises: (a) a first antigen-binding domain comprising a HCVR of SEQ ID NO: 12 and a LCVR of SEQ ID NO: 20; and (b) a second antigen-binding domain comprising a HCVR of SEQ ID NO: 28 and a LCVR of SEQ ID NO: 20. In one embodiment, the anti-BCMA/anti-CD3 bispecific antibody comprises: (a) a first antigen-binding domain comprising a HCVR of SEQ ID NO: 12 and a LCVR of SEQ ID NO: 20; and (b) a second antigen-binding domain comprising a HCVR of SEQ ID NO: 36 and a LCVR of SEQ ID NO: 20.

In one embodiment, the IL-4/IL-13 pathway inhibitor is administered prior to the plasma cell ablating agent. In one embodiment, wherein the IL-4/IL-13 pathway inhibitor is administered after the plasma cell ablating agent. In one embodiment, the administration of the IL-4/IL-13 pathway inhibitor in combination with a plasma cell ablating agent blocks IgE production and eliminates allergen-specific IgE from the serum in the patient as compared to a subject treated with either therapeutic as monotherapy.

In another embodiment, one or more doses of the IL-4/IL-13 pathway inhibitor are administered in combination with one or more doses of the plasma cell ablating agent. In another embodiment, at least one dose of the IL-4/IL-13 pathway inhibitor includes about 0.1 to about 50 mg/kg of the subject's body weight. In another embodiment, at least one dose of the IL-4/IL-13 pathway inhibitor includes about 0.05 to about 600 mg of the inhibitor. In another embodiment, at least one dose of the plasma cell ablating agent includes about 0.1 mg/kg to about 20 mg/kg of the subject's body weight. In another embodiment, at least one dose of the plasma cell ablating agent includes about 0.05 to about 500 mg of the agent.

In another embodiment, the method further includes administering at least one additional therapeutic agent or therapy. In another embodiment, the additional therapeutic agent or therapy includes an IgE antagonist, an anti-histamine, an anti-inflammatory agent, a corticosteroid, a leukotriene antagonist, a mast cell inhibitor, a bronchial dilator, a decongestant, epinephrine, an IL-1 antagonist, an IL-5 antagonist, an IL-31 antagonist, an IL-33 antagonist, an IL-25 antagonist, interferon γ, a TNF antagonist, and/or a TSLP antagonist.

In another aspect, the present disclosure provides pharmaceutical compositions and combinations for treating an allergy, allergic reaction, or allergic disorder, for preventing or reducing the severity of an allergic reaction, for reducing or eliminating allergen-specific serum IgE in a subject, or for increasing the efficacy and/or tolerability of an immunotherapy regimen in a subject having an allergy. In some embodiments, the pharmaceutical composition or combination comprises an IL-4/IL-13 pathway inhibitor (e.g., an anti-IL-4Rα antibody) and a plasma cell ablating agent (e.g., a BCMA targeting agent). In some embodiments, the pharmaceutical composition or combination comprises a therapeutically effective amount of an IL-4/IL-13 pathway inhibitor (e.g., an anti-IL-4Rα antibody) and a therapeutically effective amount of a plasma cell ablating agent (e.g., a BCMA targeting agent). In some embodiments, the pharmaceutical composition or combination comprises a subtherapeutic dose of an IL-4/IL-13 pathway inhibitor (e.g., an anti-IL-4Rα antibody) and/or a plasma cell ablating agent (e.g., a BCMA targeting agent).

In still another aspect, the present disclosure provides for the use of an IL-4/IL-13 pathway inhibitor (e.g., an anti-IL-4Rα antibody) and a plasma cell ablating agent (e.g., a BCMA targeting agent) in the manufacture of a medicament for treating an allergy, allergic reaction, or allergic disorder, for preventing or reducing the severity of an allergic reaction, for reducing or eliminating allergen-specific serum IgE in a subject, or for increasing the efficacy and/or tolerability of an immunotherapy regimen in a subject having an allergy. In some embodiments, one or both of the IL-4/IL-13 pathway inhibitor and a plasma cell ablating agent is used in a therapeutic effective amount. In some embodiments, one or both of the IL-4/IL-13 pathway inhibitor and a plasma cell ablating agent is used at a subtherapeutic dose.

DETAILED DESCRIPTION

Figure 1:
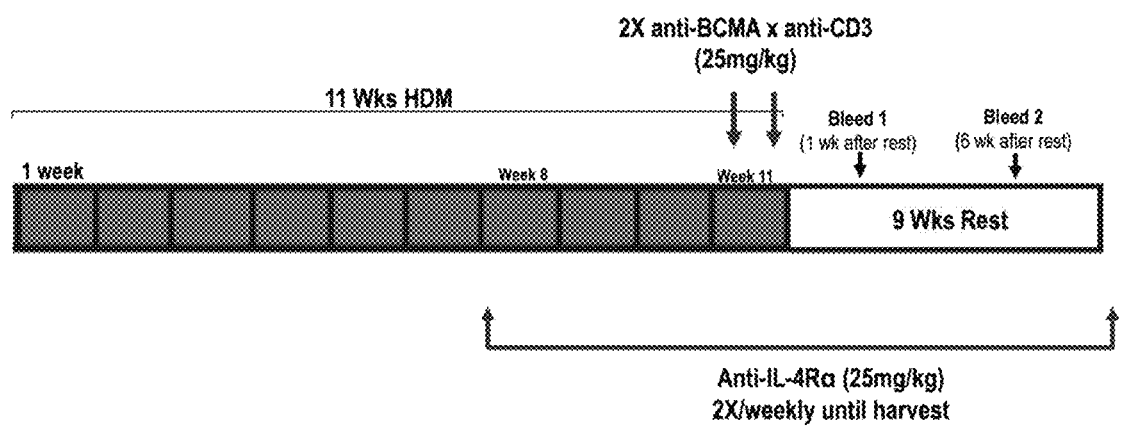
FIG. 1 is a diagrammatic representation of the house dust mite (HDM) exposure and antibody treatment protocol in accordance with the study described in Example 1.

It is to be understood that the present disclosure is not limited to the particular methods and experimental conditions described, as such methods and conditions may vary. It is also to be understood that the terminology used herein is for the purpose of describing particular embodiments only, and is not intended to be limiting, and that the scope of the present disclosure will be limited only by the appended claims.

Unless defined otherwise, all technical and scientific terms used herein have the same meaning as commonly understood by one of ordinary skill in the art to which the disclosure belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present disclosure, the preferred methods and materials are now described.

INTRODUCTION

Allergic symptoms, including anaphylaxis, are driven by allergen-induced cross-linking of allergen-specific IgE bound to FcεR on effector cells (mast cells and basophils) that can induce mast cell degranulation. In allergic individuals, circulating IgE arises from the antibody-secreting cells in the bone marrow and from B cells that class-switch to produce new IgE-producing cells. The antibody-secreting cells that accumulate in the bone marrow are long-lived and are a source of allergen-specific IgE, even in the absence of the allergen. Further, allergen-specific IgE can be long-lived in an individual, as evidenced by, at least, the following: (1) IgE is maintained in atopic patients in the absence of allergen (Luger et al., *Allergol Int* 2010, 59:1-8); (2) allergy can be transferred from an atopic patient to a non-atopic individual during a bone marrow transplant from the former to the latter (Garzorz et al., *J Eur Acad Dermatol Venereol* 2016, 30:1136-1139; Hallstrand et al., *Blood* 2004, 104: 3086-3090); and (3) serum IgE is not abolished in patients with IgE+ B-cell ablation approaches (Gauvreau et al., *Sci Transl Med* 2014, 6:243ra85).

In initial studies, the inventors of the present disclosure observed that treatment with an anti-IL-4R antibody prevented class-switching and differentiation of B cells to IgE-producing plasma cells in a mouse model of allergen-induced lung inflammation but did not impact the IgE+ plasma cells in the bone marrow during chronic allergen exposure. The inventors thus hypothesized that treatment with an IL-4/IL-13 pathway inhibitor in combination with targeted ablation of the long-lived plasma cells (including IgE+ plasma cells) might lead to blocking IgE production from the newly generated IgE+ plasma cells as well as from IgE+ plasma cells in the bone marrow. As shown herein, this therapeutic combination can significantly reduce or completely block the production of allergen-specific IgE in an animal model of allergen (HDM)-induced type 2 lung inflammation. Such a combination of therapeutic agents could therefore also be useful in treating allergic disease in atopic subjects.

Methods of Treating Allergy

In one aspect, the present disclosure relates to the surprising results obtained by the inventors, wherein administration of an IL-4/IL-13 pathway inhibitor (e.g., an anti-IL-4R antibody) in combination with a plasma cell ablating agent (e.g., an anti-BCMA/anti-CD3 bispecific antibody) resulted in complete elimination of allergen-specific IgE in the serum of subjects in the chronic allergen-induced lung inflammation model.

Accordingly, in some embodiments the present disclosure provides methods for treating, ameliorating, or reducing the severity of at least one symptom or indication of allergy in a subject. In some embodiments, the present disclosure provides methods for preventing or reducing the severity of an allergic reaction in a subject. In one aspect, the disclosed methods include selecting a subject with an allergic disease or disorder, a mast cell activation disorder, or mastocytosis; and administering to the subject in need thereof a therapeutically effective amount of an IL-4/IL-13 pathway inhibitor (e.g., an anti-IL-4 antibody, an anti-IL-13 antibody, an anti-IL-4/IL-13 bispecific antibody, an IL-4 receptor (IL-4R) inhibitor, an anti-IL-4R antibody, or any other "IL-4/IL-13 pathway inhibitor" as described herein) and a therapeutically effective amount of a plasma cell ablating agent (e.g., an anti-BCMA/anti-CD3 bispecific antibody, or any other "plasma cell ablating agent" as described herein).

In the present disclosure, references to any particular anti-IL-4R antibody and/or any particular plasma cell ablating agent are provided to illustrate a representative IL-4/IL-13 pathway inhibitor and a representative plasma cell ablating agent, respectively, and do not limit the scope of the disclosure as combinations of other IL-4/IL-13 pathway inhibitors and plasma cell ablating agents may also be used.

As used herein, the terms "treat," "treating," or the like, mean to alleviate allergic symptoms, eliminate the causation of allergic symptoms either on a temporary or permanent basis, or to prevent or slow the appearance of allergic symptoms in a subject. The terms, as used herein, also include reducing or abrogating allergen-specific serum IgE to prevent an allergic reaction. In some embodiments, the terms refer to decreasing the level of serum allergen-specific IgE by at least 50%, 60%, 70%, 80% or more as compared to baseline, upon administration of a IL-4/IL-13 pathway inhibitor in combination with a plasma cell ablating agent as provided by methods of the present disclosure. In certain embodiments, the terms refer to eliminating the level of serum allergen-specific IgE as compared to baseline, upon administration of a IL-4/IL-13 pathway inhibitor in combination with a plasma cell ablating agent as provided by methods of the present disclosure.

As used herein, the expression "a subject in need thereof" means a human or non-human animal that exhibits one or more symptoms or indicia of allergy or atopy, and/or who has been diagnosed with allergy to an allergen. The terms "subject" and "patient" are used interchangeably herein. In certain embodiments, the term "subject in need thereof" includes subjects that are at an increased risk for developing an allergy or an allergic response to an allergen. In certain embodiments, the term includes subjects that show allergen sensitization to one or more allergens. In certain embodiments, the methods of the present disclosure may be used to treat subjects that show elevated levels of one or more serum biomarkers including, but not limited to, total IgE, allergen-specific IgE, thymus and activation-regulated chemokine (TARC), pulmonary and activation-regulated chemokine (PARC), lactate dehydrogenase (LDH), and/or periostin. For example, in some embodiments the methods of the present disclosure comprise administering a IL-4/IL-13 pathway inhibitor in combination with a plasma cell ablating agent to patients with elevated levels of allergen-specific serum IgE.

The term "subject in need thereof" also includes subjects with an allergic disease or disorder selected from the group consisting of allergic asthma, hay fever, chronic urticaria, food allergy, pollen allergy, and allergy due to an environmental (non-food) allergen. The term also includes subjects that suffer from severe allergy due to one or more allergens. For example, in some embodiments, a subject has a "severe" allergy if the subject exhibits one or more severe symptoms of an allergic response, such as a symptom of anaphylaxis (e.g., difficult/noisy breathing, swelling of tongue, swelling/tightness in throat, difficulty talking and/or hoarse voice, wheeze or persistent cough, nausea/vomiting, persistent dizziness, collapse, or loss of consciousness).

In certain embodiments, the term "subject in need thereof" includes a subject that is susceptible to an allergic reaction or is at an increased risk for developing an allergic reaction to an allergen. For example, the term includes subjects that are at risk of anaphylaxis due an allergen such as peanut or penicillin. In certain embodiments, a subject may be at an increased risk of developing an allergy or an allergic response to an allergen due to sensitization to said allergen. For example, the term includes subjects that show increased levels of serum IgE specific to one or more allergens ("allergen sensitization"), e.g., to one or more food allergens and/or environmental allergens. In some embodiments, the subject has an allergen-specific IgE level of at least about 0.35 kU/L (e.g., for one or more allergens as disclosed herein, such as a food allergen or an environmental allergen, or an allergen selected from the group consisting of milk, a dairy product, egg, celery, sesame, wheat, meat, fruit, soy, fish, shellfish, a sugar, peanuts, a legume, a tree nut, dust, dust mite, pollen, insect venom, mold, animal fur, animal dander, wool, latex, a metal, a household cleaner, a detergent, medication, cosmetics, perfumes, a drug such as penicillin, sulfonamides, or salicylate, therapeutic monoclonal antibodies, ragweed, grass, and birch). In the context of the present disclosure, the term "subject in need thereof" also includes subjects having an atopic disease and subjects that have a disease or disorder selected from the group consisting of atopic dermatitis, asthma, allergic rhinitis, eosinophilic esophagitis and food allergy. The term "subject" also includes subjects with elevated levels of serum total and allergen-specific IgE, or serum chemokines (e.g., CCL17 or CCL27) that may have an increased risk of developing an allergic response. In one aspect, the present disclosure provides methods to decrease the risk of developing allergy or allergic response in susceptible subjects.

As used herein, the terms "allergic response," "allergic reaction," "allergic symptom," and the like, include one or more signs or symptoms selected from the group consisting of urticaria (e.g., hives), angioedema, rhinitis, asthma, vomiting, sneezing, runny nose, sinus inflammation, watery eyes, wheezing, bronchospasm, reduced peak expiratory flow (PEF), gastrointestinal distress, flushing, swollen lips, swollen tongue, reduced blood pressure, anaphylaxis, and organ dysfunction/failure. An "allergic response," "allergic reaction," "allergic symptom," etc., also includes immunological responses and reactions such as, e.g., increased IgE production and/or increased allergen-specific immunoglobulin production.

The term "allergen," as used herein, includes any substance, chemical, particle or composition which is capable of stimulating an allergic response in a susceptible individual. Allergens may be contained within or derived from a food item such as, e.g., dairy products (e.g., cow's milk), egg, celery, sesame, wheat, meat, soy, fish, shellfish, sugars (e.g., sugars present on meat such as alpha-galactose), peanuts, other legumes (e.g., beans, peas, soybeans, etc.), and tree nuts; an allergen that is contained within or derived from a food item is referred to herein as a "food allergen." Alternatively, an allergen may be contained within or derived from a non-food item, e.g., an indoor or outdoor environmental allergen such as, e.g., dust (e.g., containing dust mite), pollen, insect venom (e.g., venom of bees, wasps, mosquitos, fire ants, etc.), mold, animal fur, animal dander, wool, latex, metals (e.g., nickel), household cleaners, detergents, medication, cosmetics (e.g., perfumes, etc.), drugs (e.g., penicillin, sulfonamides, salicylate, etc.), therapeutic monoclonal antibodies (e.g., cetuximab), ragweed, grass and birch. Exemplary pollen allergens include, e.g., tree pollens such as birch pollen, cedar pollen, oak pollen, alder pollen, hornbeam pollen, aesculus pollen, willow pollen, poplar pollen, plantanus pollen, tilia pollen, olea pollen, Ashe juniper pollen, and *Alstonia scholaris* pollen. Other examples of allergens can be found elsewhere herein.

The present disclosure includes methods for treating allergy, including severe allergy, or preventing or reducing the severity of an allergic reaction, comprising administering to a subject in need thereof a therapeutically effective amount of an IL-4/IL-13 pathway inhibitor (e.g., an anti-IL-4R antibody as described herein) in combination with a therapeutically effective amount of a plasma cell ablating agent (e.g., an anti-BCMAxanti-CD3 bispecific antibody as described herein). In some embodiments, the disclosed methods target an allergic disease or disorder, mast cell activation disorder, or mastocytosis. In one embodiment, the allergic disease or disorder is selected from the group consisting of allergic asthma, hay fever, chronic urticaria, food allergy, pollen allergy, and allergy due to an environmental (non-food) allergen. In some embodiments, the allergic disease is a food allergy, e.g., a peanut allergy. In some embodiments, the allergic disease is a severe food allergy.

According to certain embodiments, the present disclosure includes methods of treating allergy or preventing or reducing the severity of an allergic reaction, the methods comprising: (a) selecting a patient with an allergic disease or disorder, a mast cell activation disorder or mastocytosis, wherein the patient is on a background therapy regimen comprising one or more doses of an IL-4/IL-13 pathway inhibitor; and (b) administering at least one dose of a plasma cell ablating agent. The methods, in this aspect, enhance the therapeutic efficacy of the IL-4/IL-13 pathway inhibitor in reducing the serum levels of allergen-specific IgE. In certain embodiments, the patient is on a therapeutic regimen comprising one or more doses of a IL-4/IL-13 pathway and is administered one or more doses of a plasma cell ablating agent, thereby enhancing the anti-allergic effect of the IL-4/IL-13 pathway inhibitor.

In some embodiments, the disclosed methods include administering a therapeutically effective amount of an IL-4/IL-13 pathway inhibitor and a therapeutically effective amount of a plasma cell ablating agent in combination with an additional therapeutic agent or therapy (e.g., regimen or procedure). The additional therapeutic agent or therapy may be administered for increasing anti-allergic efficacy, for reducing toxic effects of one or more therapies and/or for reducing the dosage of one or more therapies. In various embodiments, the additional therapeutic agent or therapy may include one or more of an IgE antagonist, an anti-histamine, an anti-inflammatory agent, a corticosteroid, a leukotriene antagonist, a mast cell inhibitor, a bronchial dilator, a decongestant, epinephrine, an IL-1 antagonist, an IL-5 antagonist, an IL-31 antagonist, an IL-33 antagonist, an IL-25 antagonist, interferon γ, a TNF antagonist, and a TSLP antagonist.

The additional therapeutic agent may be, e.g., another IL-4R antagonist, an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), an IL-13 antagonist, a tumor necrosis factor (TNF) antagonist, an IL-8 antagonist, an IL-9 antagonist, an IL-17 antagonist, an IL-5 antagonist, an IgE antagonist (e.g., an anti-IgE antibody such as omalizumab), a CD48 antagonist, an IL-31 antagonist (including, e.g., as set forth in U.S. Pat. No. 7,531,637), a thymic stromal lymphopoietin (TSLP) antagonist (including, e.g., as set forth in US 2011/027468), interferon-gamma (IFNγ), antibiotics, topical corticosteroids, tacrolimus, pimecrolimus, cyclosporine, azathioprine, methotrexate, cromolyn sodium, proteinase inhibitors, systemic corticosteroids, systemic immunotherapy, anti-histamines, or combinations thereof.

In certain embodiments, the disclosed methods of administering a therapeutically effective amount of an IL-4/IL-13 pathway inhibitor and a therapeutically effective amount of a plasma cell ablating agent leads to reduction or abrogation of one or more symptoms or indications of an allergy as compared to an untreated subject or a subject treated with either inhibitor as monotherapy.

In certain embodiments, the disclosed methods lead to reduction, preferably total elimination of allergen-specific IgE in the treated subject. For instance, the disclosed methods of administering a therapeutically effective amount of an IL-4/IL-13 pathway inhibitor and a therapeutically effective amount of a plasma cell ablating agent promote at least about 50%, about 60%, about 70% or about 80% more decrease in the serum level of allergen-specific IgE in the treated subject as compared to an untreated subject or a subject treated with either inhibitor as monotherapy. In certain embodiments, the disclosed methods lead to complete elimination of allergen-specific serum IgE in the treated subject as compared to a subject treated with either agent as monotherapy.

According to certain embodiments, a subject may exhibit a decrease in the level of serum IgE specific to one or more allergens following administration of one or more doses of a IL-4/IL-13 pathway inhibitor (e.g., an anti-IL-4R antibody) in combination with one or more doses of a plasma cell ablating agent (e.g., an anti-BCMA/anti-CD3 bispecific antibody). For example, at about day 8, day 15, day 22, day 25, day 29, day 36, day 43, day 50, day 57, day 64, day 71, day 85, or day 112, following administration of one or more doses of an anti-IL-4R antibody (e.g., dupilumab) in combination with a plasma cell ablating agent, the subject, according to the present disclosure, may exhibit a decrease in allergen-specific IgE of about 50%, 55%, 60%, 65%, 70%, 75%, 80%, 85%, 90% or more from baseline (wherein "baseline" is defined as the level of allergen-specific IgE in the subject just prior to the first administration).

Methods for detecting and/or quantifying allergen-specific IgE or total IgE in the serum are known in the art; kits for measuring such are available from various commercial sources; and various commercial diagnostic laboratories offer services which provide measurement of such levels as well.

For example, Phadiatop™ is a commercially available variant of serum specific or antigen-specific IgE assay test that was introduced for the screening of allergic sensitization (Merrett et al 1987, Allergy 17: 409-416). The test provides for simultaneous testing for serum specific IgE to a mixture of relevant allergens causing common inhalant allergies. The test gives a qualitative result, either positive or negative depending upon a fluorescence response obtained. When a patient sample gives a fluorescence response higher than or equal to the reference, a positive test result is indicated. A patient sample with a lower fluorescence response indicates a negative test result. The present disclosure includes methods comprising selecting a subject who exhibits a positive test result and administering to the subject a therapeutically effective amount of an IL-4/IL-13 pathway inhibitor in combination with a plasma cell ablating agent.

In certain embodiments, the combination of administered therapeutic agents is safe and well tolerated by the subject such that there is no increase in adverse side effects as compared to a subject treated with either therapeutic agent as monotherapy.

IL-4/IL-13 Pathway Inhibitors

The methods disclosed herein include administering a therapeutically effective amount of an IL-4/IL-13 pathway inhibitor to a subject in need thereof. As used herein, an "IL-4/IL-13 pathway inhibitor" (also referred to herein as an "IL-4/IL-13 pathway antagonist," an "IL-4/IL-13 pathway blocker," etc.) is any agent that inhibits or attenuates at least one of: (i) the binding of IL-4 and/or IL-13 to their respective receptors; (ii) signaling and/or activity of IL-4 and/or IL-13; and/or (iii) the downstream signaling/activity that results from binding of IL-4 and/or IL-13 to their respective receptors. Exemplary IL-4/IL-13 pathway inhibitors include, but are not limited to, anti-IL-4 antibodies (e.g., the antibodies disclosed in U.S. Pat. No. 7,740,843, and US Patent Application Publications 2010/0297110 and 2016/0207995), anti-IL-13 antibodies (e.g., the antibodies disclosed in U.S. Pat. Nos. 7,501,121, 7,674,459, 7,807,788, 7,910,708, 7,915,388, 7,935,343, 8,088,618, 8,691,233, and 9,605,065, US Patent Application Publications 2006/0073148 and 2008/0044420, and EP2627673B1), bispecific antibodies that bind to IL-4 and IL-13 (e.g., the antibodies disclosed in U.S. Pat. No. 8,388,965 and US Patent Application Publications 2011/0008345, 2013/0251718, and 2016/0207995), and IL-4 receptor (IL-4R) inhibitors (described below). The portions of the publications cited herein that identify IL-4/IL-13 pathway inhibitors are hereby incorporated by reference.

In some embodiments, the IL-4/IL-13 pathway inhibitor can be an antibody, a small molecule compound, a nucleic acid, a polypeptide, or a functional fragment or variant thereof. Non-limiting examples of suitable IL-4/IL-13 pathway inhibitor antibodies include anti-IL-4 antibodies, anti-IL-13 antibodies, and anti-IL-4/IL-13 bispecific antibodies, anti-IL-4R antibodies, and antigen-binding fragments of any of the foregoing. Other non-limiting examples of suitable IL-4/IL-13 pathway inhibitors include: RNAi molecules such as anti-IL-4 RNAi molecules and anti-IL-13 RNAi, antisense molecules such as anti-IL-4 antisense RNA and anti-IL-13 antisense RNA, and dominant negative proteins such as a dominant negative IL-4 protein, a dominant negative IL-13 protein.

As used herein, an "IL-4R inhibitor" (also referred to herein as an "IL-4/IL-13 pathway inhibitor," an "IL-4Rα antagonist," an "IL-4R blocker," an "IL-4Rα blocker," etc.) is any agent which binds to or interacts with IL-4Rα or an IL-4R ligand, and inhibits or attenuates the normal biological signaling function a type 1 and/or a type 2 IL-4 receptor. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R inhibitors that can be used in the methods of the present disclosure may function by blocking IL-4-mediated signaling, IL-13-mediated signaling, or both IL-4- and IL-13-mediated signaling. The IL-4R inhibitors of the present disclosure may thus prevent the interaction of IL-4 and/or IL-13 with a type 1 or type 2 receptor.

Non-limiting examples of categories of IL-4R inhibitors include IL-4 muteins (e.g., pitrakinra), small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R inhibitors also include antigen-binding proteins that specifically bind IL-4 and/or IL-13.

Other non-limiting examples of suitable IL-4/IL-13 pathway inhibitors that can be used in the context of the present disclosure include, e.g., pitrakinra (AER-001; BAY-16-9996), aeroderm (AER-003), and the antibodies referred to and known in the art as dupilumab, pascolizumab, AMG-317, MILR1444A, CAT-354, QAX576, anrukinzumab (IMA-638), ISIS-369645 (AIR-645), IMA-026, APG-201, CNTO-607, MK-6105, MEDI9314, MEDI2045, tralokinumab, lebrikizumab, romilkimab, and DOM-0910.

Anti-IL-4Rα Antibodies and Antigen-Binding Fragments Thereof

According to certain exemplary embodiments of the present disclosure, the IL-4/IL-13 pathway inhibitor is an anti-IL-4Rα antibody or antigen-binding fragment thereof. The term "antibody," as used throughout the present disclosure, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the antibody (or antigen-binding portion thereof) may be identical to the human germline sequences or may be naturally or artificially modified. An amino acid consensus sequence may be defined based on a side-by-side analysis of two or more CDRs.

The term "antibody," as used throughout the present disclosure, includes antigen-binding fragments thereof—i.e., antigen-binding fragments of full antibody molecules. The terms "antigen-binding portion" of an antibody," "antigen-binding fragment" of an antibody, and the like, as used throughout the present disclosure, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used throughout the present disclosure.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

The term "antibody," as used throughout the present disclosure, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present disclosure using routine techniques available in the art. For example, the present disclosure includes methods comprising the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4(6):653-663, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.,* 2013, 135(1):340-46).

The antibodies used in the methods of the present disclosure may be human antibodies. The term "human antibody," as used throughout the present disclosure, is intended to include antibodies having variable and constant regions derived from human germline immunoglobulin sequences. The human antibodies of the disclosure may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used throughout the present disclosure, is not intended to include antibodies in which CDR sequences derived from the germline of another mammalian species, such as a mouse, have been grafted onto human framework sequences.

The antibodies used in the methods of the present disclosure may be recombinant human antibodies. The term "recombinant human antibody," as used throughout the present disclosure, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see, e.g., Taylor et al. (1992) *Nucl. Acids Res.,* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present disclosure specifically bind IL-4Rα. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, in some embodiments, an antibody that "specifically binds" IL-4Rα, as used in the context of the present disclosure, includes antibodies that bind IL-4Rα or portion thereof with a $K_D$ of less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4Rα may, however, have cross-reactivity to other antigens, such as IL-4Rα molecules from other (non-human) species.

According to certain exemplary embodiments of the present disclosure, the IL-4/IL-13 pathway inhibitor is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693, incorporated by reference herein. In certain exemplary embodiments, the anti-IL-4Rα antibody or antigen-binding fragment thereof that can be used in the context of the methods of the present disclosure comprises the heavy chain complementarity determining regions (HCDRs) of a heavy chain variable region (HCVR) comprising the amino acid sequence of SEQ ID NO: 1 and the light chain complementarity determining regions (LCDRs)

of a light chain variable region (LCVR) comprising the amino acid sequence of SEQ ID NO: 2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In yet other embodiments, the anti-IL-4R antibody or antigen-binding fragment thereof comprises an HCVR comprising SEQ ID NO: 1 and an LCVR comprising SEQ ID NO: 2. In certain embodiments, the methods of the present disclosure comprise the use of an anti-IL-4R antibody, wherein the antibody comprises a heavy chain comprising the amino acid sequence of SEQ ID NO: 9. In some embodiments, the anti-IL-4R antibody comprises a light chain comprising the amino acid sequence of SEQ ID NO: 10. An exemplary antibody comprising a heavy chain comprising the amino acid sequence of SEQ ID NO: 9 and a light chain comprising the amino acid sequence of SEQ ID NO: 10 is the fully human anti-IL-4R antibody known as dupilumab (DUPIXENT™). According to certain exemplary embodiments, the methods of the present disclosure comprise the use of dupilumab, or a bioequivalent thereof. The term "bioequivalent" with respect to dupilumab refers to anti-IL-4R antibodies or IL-4R-binding proteins or fragments thereof that are pharmaceutical equivalents or pharmaceutical alternatives having a rate and/or extent of absorption that does not show a significant difference with that of dupilumab when administered at the same molar dose under similar experimental conditions, either single dose or multiple dose. In the context of the present disclosure, the term refers to antigen-binding proteins that bind to IL-4R which do not have clinically meaningful differences with dupilumab in their safety, purity and/or potency.

According to certain embodiments of the present disclosure, the anti-human IL-4R antibody or antigen-binding fragment thereof comprises a HCVR having at least 90%, 91%, 92%, 93%, 94%, 95%, 96%, 97%, 98%, or 99% sequence identity to SEQ ID NO: 1. In some embodiments, the anti-human IL-4R antibody or antigen-binding fragment thereof comprises three HCDRs (HCDR1, HCDR2 and HCDR3) comprising the amino acid sequences of SEQ ID NOs:3, 4, and 5, respectively, and comprises a HCVR having at least 90%, at least 91%, at least 92%, at least 93%, at least 94%, at least 95%, at least 96%, at least 97%, at least 98%, or at least 99% sequence identity to SEQ ID NO:1.

According to certain embodiments of the present disclosure, the anti-human IL-4R antibody or antigen-binding fragment thereof comprises a LCVR having at least 90%, 91%, 92%, 93%, 94%, 95%, 96%, 97%, 98%, or 99% sequence identity to SEQ ID NO: 2. In some embodiments, the anti-human IL-4R antibody or antigen-binding fragment thereof comprises three LCDRs (LCDR1, LCDR2 and LCDR3) comprising the amino acid sequences of SEQ ID NOs:6, 7, and 8, respectively, and comprises a LCVR having at least 90%, at least 91%, at least 92%, at least 93%, at least 94%, at least 95%, at least 96%, at least 97%, at least 98%, or at least 99% sequence identity to SEQ ID NO:2.

According to certain embodiments of the present disclosure, the anti-human IL-4R antibody or antigen-binding fragment thereof comprises a HCVR comprising an amino acid sequence of SEQ ID NO: 1 having no more than 5 amino acid substitutions. According to certain embodiments of the present disclosure, the anti-human IL-4R antibody or antigen-binding fragment thereof comprises a LCVR comprising an amino acid sequence of SEQ ID NO: 2 having no more than 2 amino acid substitutions.

In some embodiments, the anti-human IL-4R antibody or antigen-binding fragment thereof comprises a HCVR having 90%, 91%, 92%, 93%, 94%, 95%, 96%, 97%, 98%, or 99% sequence identity to SEQ ID NO: 1 and a LCVR having 90%, 91%, 92%, 93%, 94%, 95%, 96%, 97%, 98%, or 99% sequence identity to SEQ ID NO: 2. In some embodiments, the anti-human IL-4R antibody or antigen-binding fragment thereof comprises (a) an HCDR1, HCDR2 and HCDR3 comprising the amino acid sequences of SEQ ID NOs:3, 4, and 5, respectively, and a HCVR having at least 90%, at least 91%, at least 92%, at least 93%, at least 94%, at least 95%, at least 96%, at least 97%, at least 98%, or at least 99% sequence identity to SEQ ID NO:1; and (b) an LCDR1, LCDR2 and LCDR3 comprising the amino acid sequences of SEQ ID NOs:6, 7, and 8, respectively, and a LCVR having at least 90%, at least 91%, at least 92%, at least 93%, at least 94%, at least 95%, at least 96%, at least 97%, at least 98%, or at least 99% sequence identity to SEQ ID NO:2.

Sequence identity may be measured by methods known in the art (e.g., GAP, BESTFIT, and BLAST).

The present disclosure also includes use of anti-IL-4R antibodies in methods to treat allergy or to eliminate allergen-specific IgE in a subject, wherein the anti-IL-4R antibodies comprise variants of any of the HCVR, LCVR and/or CDR amino acid sequences disclosed herein having one or more conservative amino acid substitutions. For example, the present disclosure includes use of anti-IL-4R antibodies having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein. In some embodiments, the disclosure includes use of an anti-IL-4R antibody having HCVR, LCVR and/or CDR amino acid sequences with 1, 2, 3, or 4 conservative amino acid substitutions relative to any of the HCVR, LCVR and/or CDR amino acid sequences disclosed herein.

Other anti-IL-4Rα antibodies that can be used in the context of the methods of the present disclosure include, e.g., the antibody referred to and known in the art as AMG317 (Corren et al., 2010, *Am J Respir Crit Care Med.*, 181(8):788-796), or MEDI 9314, or any of the anti-IL-4Rα antibodies as set forth in U.S. Pat. Nos. 7,186,809, 7,605, 237, 7,638,606, 8,092,804, 8,679,487, or 8,877,189. The portions of the publications cited herein that identify anti-IL-4Rα antibodies are hereby incorporated by reference.

The anti-IL-4Rα antibodies used in the context of the methods of the present disclosure may have pH-dependent binding characteristics. For example, an anti-IL-4Rα antibody for use in the methods of the present disclosure may exhibit reduced binding to IL-4Rα at acidic pH as compared to neutral pH. Alternatively, an anti-IL-4Rα antibody of the present disclosure may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used throughout the present disclosure, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present disclosure if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present disclosure can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used throughout the present disclosure, the expression "acidic pH" means a pH of 6.0 or less.

Plasma Cell Ablating Agents

The methods disclosed herein include administering a therapeutically effective amount of a plasma cell ablating agent to a subject in need thereof. As used herein, a "plasma cell ablating agent" refers to any molecule capable of specifically binding to a surface antigen on plasma cells and killing or ablating said plasma cell. In some embodiments, the plasma cell ablating agent can be an antibody, a small molecule compound, a nucleic acid, a polypeptide, or a functional fragment or variant thereof. In the context of the present disclosure, a plasma cell ablating agent is used in combination with an IL-4/IL-13 pathway inhibitor in the disclosed methods.

Non-limiting examples of suitable plasma cell ablating agents include BCMA targeting agents (described elsewhere herein), proteasome inhibitors [e.g., bortezomib (Veicade), carfilzomib (Kyprolis), ixazomib (Niniaro)], histone deacetylase inhibitors [e.g., panobinostat (Farydak)], B-cell activating factor (BAFF; also referred to as BLyS, TALL-1, or CD257) inhibitors (e.g., anti-BAFF antibodies such as belimumab, tabalumab, AMG570; or anti-BAFF receptor antibodies such as ianalumab), and A proliferation-inducing ligand (APRIL; also referred to as TNFSF13 or CD256) inhibitors (e.g., anti-APRIL antibodies such as BION-1301 or VIS624).

BCMA Targeting Agents

According to certain exemplary embodiments, the plasma cell ablating agents used in the methods disclosed herein are BCMA targeting agents.

As used herein, the term "BCMA targeting agent" refers to any molecule capable of binding specifically to BCMA that is expressed on the surface of a cell in a subject, thus targeting said cell for destruction. BCMA is expressed exclusively in B-cell lineage cells, particularly in the interfollicular region of the germinal center as well as on plasmablasts and differentiated plasma cells. BCMA is selectively induced during plasma cell differentiation and is required for optimal survival of long-lived plasma cells in the bone marrow. Thus, a BCMA targeting agent binds to BCMA expressed on plasma cell surface and mediates killing or ablation of cells that express BCMA (plasma cell ablation). In the context of the present disclosure, in some embodiments a BCMA targeting agent comprises a binding moiety that binds to plasma cell-surface-expressed BCMA (an antigen-binding moiety or antigen-binding fragment thereof) and a moiety that facilitates killing of said plasma cell. In certain embodiments, the plasma cell-surface-expressed BCMA-binding moiety is an antibody or antigen-binding fragment thereof that binds specifically to BCMA. Such a BCMA-binding moiety is linked (e.g., covalently bound) to a moiety that facilitates killing or destruction of the targeted plasma cell. The moiety that facilitates targeted killing of the bound plasma cell may be a molecule that directly kills the targeted cell (e.g., a cytotoxic agent) or may be a protein or fragment thereof that mediates killing of the targeted cell by an immune cell, e.g., a T-cell. In the context of the present disclosure, the term "BCMA targeting agent" includes, but is not limited to, anti-BCMA antibodies that are conjugated to a therapeutic agent such as a cytotoxic drug ("BCMA ADC" or "anti-BCMA ADC"), chimeric antigenic receptors (CARs) that bind specifically to BCMA, ("BCMA CAR" or "anti-BCMA CAR") and anti-BCMA/anti-CD3 bispecific antibodies.

According to certain embodiments, the BCMA targeting agent used in the context of the disclosed methods is an antibody-drug conjugate (ADC) comprising an anti-BCMA antibody and a cytotoxic drug. In some embodiments, the anti-BCMA antibody or antigen-binding fragment thereof and the cytotoxic agent are covalently attached via a linker. In general terms, the ADCs comprise: A-[L-P]$_y$, in which A is an antigen-binding molecule, e.g., an anti-BCMA antibody, or a fragment thereof, L is a linker, P is the payload or therapeutic moiety (e.g., cytotoxic agent), and y is an integer from 1 to 30. Examples of suitable cytotoxic agents and chemotherapeutic agents for forming ADCs are known in the art. Non-limiting examples of suitable cytotoxic agents that can be conjugated to anti-BCMA antibodies for use in the disclosed methods are auristatin such as monomethyl auristatin E (MMAE) or monomethyl auristatin F (MMAF), a tubulysin such as TUB-OH or TUB-OMOM, a tomaymycin derivative, a dolastatin derivative, or a maytansinoid such as DM1 or DM4. According to certain exemplary embodiments, the present disclosure includes use of anti-BCMA ADCs in methods to treat allergies, wherein the anti-BCMA ADCs comprise any of the HCVR, LCVR and/or CDR amino acid sequences disclosed elsewhere herein.

The present disclosure also includes use of anti-BCMA ADCs in methods to treat allergy, wherein the antibodies comprise variants of any of the HCVR, LCVR and/or CDR amino acid sequences disclosed herein having one or more conservative amino acid substitutions. For example, the present disclosure includes use of antibodies having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein. In some embodiments, the disclosure includes use of an antibody having HCVR, LCVR and/or CDR amino acid sequences with 1, 2, 3, or 4 conservative amino acid substitutions relative to any of the HCVR, LCVR and/or CDR amino acid sequences disclosed herein.

Other anti-BCMA ADCs that can be used in the context of the methods of the present disclosure include, e.g., the ADCs referred to and known in the art as belantamab mafodotin, GSK2857916, AMG224, HDP-101, MEDI2228, and TBL-CLN1, or any of the anti-BCMA ADCs set forth, e.g., in patent publications WO2011/108008, WO2014/

089335, WO2017/093942, WO2017/143069, WO2019/025983. The portions of the publications cited herein that identify anti-BCMA ADCs are hereby incorporated by reference.

According to certain embodiments, the BCMA targeting agent used in the context of the disclosed methods is a chimeric antigen receptor (CAR) that binds specifically to BCMA ("BCMA CAR"). The term "chimeric antigen receptor" (CAR) refers to molecules that combine a binding domain against a component present on the target cell, for example an antibody-based specificity for a desired antigen (e.g., BCMA on plasma cell) with a T cell receptor-activating intracellular domain to generate a chimeric protein that exhibits a specific anti-target cellular immune activity. Generally, CARs consist of an extracellular single chain antibody-binding domain (scFv) fused to the intracellular signaling domain of the T cell antigen receptor complex zeta chain, and have the ability, when expressed in T cells, to redirect antigen recognition based on the monoclonal antibody's specificity. In certain embodiments, the BCMA CAR or antigen-binding fragment thereof comprises a heavy chain variable region (HCVR), light chain variable region (LCVR), and/or complementarity determining regions (CDRs) comprising the amino acid sequences of any of the antibodies set forth in US provisional patent application U.S. Ser. No. 62/700,615, filed on Jul. 19, 2018, or in International Patent Application No. PCT/US2019/042452, which are hereby incorporated by reference in its entirety. According to certain exemplary embodiments, the present disclosure includes use of anti-BCMA CARs in methods to treat allergies, wherein the anti-BCMA CARs comprise any of the HCVR, LCVR and/or CDR amino acid sequences disclosed elsewhere herein.

The present disclosure also includes use of anti-BCMA CARs in methods to treat allergy, wherein the CARs comprise variants of any of the HCVR, LCVR and/or CDR amino acid sequences disclosed herein having one or more conservative amino acid substitutions. For example, the present disclosure includes use of anti-BCMA CARs having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein. In some embodiments, the disclosure includes use of an anti-BCMA CAR having HCVR, LCVR and/or CDR amino acid sequences with 1, 2, 3, or 4 conservative amino acid substitutions relative to any of the HCVR, LCVR and/or CDR amino acid sequences disclosed herein.

Other anti-BCMA CARs that can be used in the context of the methods of the present disclosure include, e.g., the CARs referred to and known in the art as bb2121, LCAR-B38M, and 4C8A, or any of the anti-BCMA CARs set forth, e.g., in patent publications WO2015/052538, WO2015/052536, WO2016/094304, WO2016/166630, WO2016/151315, WO2016/130598, WO2017/183418, WO2017/173256, WO2017211900, WO2017/130223, WO2018/229492, WO2018/085690, WO2018/151836, WO2018/028647, WO2019/006072. The portions of the publications cited herein that identify anti-BCMA CARs are hereby incorporated by reference.

According to certain exemplary embodiments, the BCMA targeting agent used in the context of the disclosed methods is an anti-BCMA/anti-CD3 bispecific antibody (also referred to herein as an "anti-BCMA×anti-CD3 bispecific antibody"). The anti-BCMA/anti-CD3 bispecific antibodies are useful for specific targeting and T-cell-mediated killing of cells that express BCMA. The terms "antibody," "antigen-binding fragment," "human antibody," "recombinant antibody," and other related terminology are defined above. In the context of anti-BCMA/anti-CD3 antibodies and antigen-binding fragments thereof, the present disclosure includes the use of bispecific antibodies wherein one arm of an immunoglobulin is specific for BCMA or a fragment thereof, and the other arm of the immunoglobulin is specific for a second therapeutic target (e.g., CD3 on T-cells). Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4(6):653-663, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.*, 2013, 135(1):340-46).

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" BCMA, as used in the context of the present disclosure, includes antibodies that bind BCMA or a portion thereof with a $K_D$ of less than about 100 nM, less than about 50 nM, less than about 20 nM, less than about 10 nM, less than about 5 nM, less than about 1 nM, less than about 500 pM, less than about 200 pM, less than about 100 pM, or less than about 50 pM, as measured in a surface plasmon resonance assay. An isolated antibody that specifically binds human BCMA may, however, have cross-reactivity to other antigens, such as BCMA molecules from other (non-human) species.

According to certain exemplary embodiments, the anti-BCMA/anti-CD3 bispecific antibody, or antigen-binding fragment thereof comprises a heavy chain variable region (HCVR), light chain variable region (LCVR), and/or complementarity determining regions (CDRs) comprising the amino acid sequences of any of the antibodies set forth in US provisional patent application U.S. Ser. No. 62/793,645, filed on Jan. 17, 2019, or in International Patent Application No. PCT/US2019/042447, which are hereby incorporated by reference in its entirety. In certain exemplary embodiments, the anti-BCMA/anti-CD3 bispecific antibody or antigen-binding fragment thereof that can be used in the context of the present disclosure comprises: (a) a first antigen binding domain that binds specifically to BCMA; and (b) a second antigen-binding domain that binds specifically to CD3. In one embodiment, the first antigen-binding domain comprises the heavy chain complementarity determining regions (HCDRs) of a heavy chain variable region (HCVR) comprising the amino acid sequence of SEQ ID NO: 12 and the light chain complementarity determining regions (LCDRs) of a light chain variable region (LCVR) comprising the amino acid sequence of SEQ ID NO: 20. According to certain embodiments, the first antigen-binding domain comprises three HCDRs (HCDR1, HCDR2 and HCDR3) and three LCDRs (LCDR1, LCDR2 and LCDR3), wherein the HCDR1 comprises the amino acid sequence of SEQ ID NO: 14; the HCDR2 comprises the amino acid sequence of SEQ ID NO: 16; the HCDR3 comprises the amino acid sequence of SEQ ID NO: 18; the LCDR1 comprises the amino acid sequence of SEQ ID NO: 22; the LCDR2 comprises the amino acid sequence of SEQ ID NO: 24; and the LCDR3 comprises the amino acid sequence of SEQ ID NO: 26. In one embodiment, the second antigen-binding domain comprises the heavy chain complementarity determining regions (HCDRs) of a heavy chain variable region (HCVR) comprising the amino acid sequence of SEQ ID NO: 28 or SEQ ID NO: 36 and the light chain complementarity determining regions (LCDRs) of a light chain variable region (LCVR) comprising the amino acid sequence of SEQ ID NO: 20. In one embodiment, the second antigen-binding domain comprises three HCDRs (HCDR1, HCDR2 and HCDR3) and three LCDRs (LCDR1, LCDR2 and LCDR3), wherein the HCDR1 comprises the amino acid sequence of SEQ ID NO: 30 or 38; the HCDR2 comprises the amino acid sequence of SEQ ID NO: 32 or 40; the HCDR3 comprises the amino acid sequence of SEQ ID NO: 34 or 42; the LCDR1 comprises the amino acid sequence of SEQ ID NO: 22; the LCDR2 comprises the amino acid sequence of SEQ ID NO: 24; and the LCDR3 comprises the amino acid sequence of SEQ ID NO: 26.

In one embodiment, the anti-BCMA/anti-CD3 bispecific antibody or antigen-binding fragment thereof comprises: (a) a first antigen-binding domain that comprises HCDR1, HCDR2, and HCDR3 domains, respectively, comprising the amino acid sequences of SEQ ID NOs: 14, 16, and 18, and LCDR1, LCDR2, and LCDR3 domains, respectively, comprising the amino acid sequences of SEQ ID NOs: 22, 24, and 26; and (b) a second antigen binding domain that comprises HCDR1, HCDR2, and HCDR3 domains, respectively, comprising the amino acid sequences of SEQ ID NOs: 30, 32, and 34, and LCDR1, LCDR2, and LCDR3 domains, respectively, comprising the amino acid sequences of SEQ ID NOs: 22, 24, and 26. In one embodiments, the anti-BCMA/anti-CD3 bispecific antibody or antigen-binding fragment thereof comprises: (a) a first antigen-binding domain that comprises a HCVR comprising the amino acid sequence of SEQ ID NO:12 and a LCVR comprising the amino acid sequence of SEQ ID NO:20; and (b) a second antigen-binding domain that comprises a HCVR comprising the amino acid sequence of SEQ ID NO:28 and a LCVR comprising the amino acid sequence of SEQ ID NO:20.

In one embodiment, the anti-BCMA/anti-CD3 bispecific antibody or antigen-binding fragment thereof comprises: (a) a first antigen-binding domain that comprises HCDR1, HCDR2, and HCDR3 domains, respectively, comprising the amino acid sequences of SEQ ID NOs: 14, 16, and 18, and LCDR1, LCDR2, and LCDR3 domains, respectively, comprising the amino acid sequences of SEQ ID NOs: 22, 24, and 26; and (b) a second antigen binding domain that comprises HCDR1, HCDR2, and HCDR3 domains, respectively, comprising the amino acid sequences of SEQ ID NOs: 38, 40, and 42, and LCDR1, L CDR2, and LCDR3 domains, respectively, comprising the amino acid sequences of SEQ ID NOs: 22, 24, and 26. In one embodiments, the anti-BCMA/anti-CD3 bispecific antibody or antigen-binding fragment thereof comprises: (a) a first antigen-binding domain that comprises a HCVR comprising the amino acid sequence of SEQ ID NO:12 and a LCVR comprising the amino acid sequence of SEQ ID NO:20; and (b) a second antigen-binding domain that comprises a HCVR comprising the amino acid sequence of SEQ ID NO:36 and a LCVR comprising the amino acid sequence of SEQ ID NO:20.

Exemplary anti-BCMA/anti-CD3 bispecific antibodies include the fully human bispecific antibodies known as REGN5458 and REGN5459. According to certain exemplary embodiments, the methods of the present disclosure comprise the use of REGN5458 or REGN5459, or a bioequivalent thereof. As used herein, the term "bioequivalent" with respect to anti-BCMA/anti-CD3 antibodies refers to antibodies or BCMA/CD3-binding proteins or fragments thereof that are pharmaceutical equivalents or pharmaceutical alternatives having a rate and/or extent of absorption that does not show a significant difference with that of a reference antibody (e.g., REGN5458 or REGN5459) when administered at the same molar dose under similar experimental conditions, either single dose or multiple dose; the term "bioequivalent" also includes antigen-binding proteins that bind to BCMA/CD3 and do not have clinically meaningful differences with the reference antibody (e.g., REGN5458 or REGN5459) with respect to safety, purity and/or potency.

In some embodiments, the anti-BCMA/anti-CD3 bispecific antibody or antigen-binding fragment thereof comprises: (a) a first antigen-binding domain that comprises a HCVR having at least 90%, 91%, 92%, 93%, 94%, 95%, 96%, 97%, 98%, or 99% sequence identity to the amino acid sequence of SEQ ID NO: 12 and a LCVR having at least 90%, 91%, 92%, 93%, 94%, 95%, 96%, 97%, 98%, or 99% sequence identity to the amino acid sequence of SEQ ID NO:20; and (b) a second antigen-binding domain that comprises a HCVR having at least 90%, 91%, 92%, 93%, 94%, 95%, 96%, 97%, 98%, or 99% sequence identity to the amino acid sequence of SEQ ID NO: 28 and a LCVR having at least 90%, 91%, 92%, 93%, 94%, 95%, 96%, 97%, 98%, or 99% sequence identity to the amino acid sequence of SEQ ID NO:20. In some embodiments, the anti-BCMA/anti-CD3 bispecific antibody or antigen-binding fragment thereof comprises: (a) a first antigen-binding domain that comprises three HCDRs (HCDR1, HCDR2 and HCDR3) comprising the amino acid sequences of SEQ ID NOs:14, 16, and 18, respectively, and a HCVR having at least 90%, 91%, 92%, 93%, 94%, 95%, 96%, 97%, 98%, or 99% sequence identity to the amino acid sequence of SEQ ID NO: 12, and comprises three LCDRs (LCDR1, LCDR2 and LCDR3) comprising the amino acid sequences of SEQ ID NOs:22, 24, and 26, respectively, and a LCVR having at least 90%, 91%, 92%, 93%, 94%, 95%, 96%, 97%, 98%, or 99% sequence identity to the amino acid sequence of SEQ ID NO:20; and (b) a second antigen-binding domain that comprises three HCDRs (HCDR1, HCDR2 and HCDR3) comprising the amino acid sequences of SEQ ID NOs:30, 32, and 34, respectively, and a HCVR having at least 90%, 91%, 92%, 93%, 94%, 95%, 96%, 97%, 98%, or 99% sequence identity to the amino acid sequence of SEQ ID NO: 28, and comprises three LCDRs (LCDR1, LCDR2 and LCDR3) comprising the amino acid sequences of SEQ ID NOs:22, 24, and 26, respectively, and a LCVR having at least 90%, 91%, 92%, 93%, 94%, 95%, 96%, 97%, 98%, or 99% sequence identity to the amino acid sequence of SEQ ID NO:20.

In some embodiments, the anti-BCMA/anti-CD3 bispecific antibody or antigen-binding fragment thereof comprises: (a) a first antigen-binding domain that comprises a HCVR having at least 90%, 91%, 92%, 93%, 94%, 95%, 96%, 97%, 98%, or 99% sequence identity to the amino acid sequence of SEQ ID NO: 12 and a LCVR having at least 90%, 91%, 92%, 93%, 94%, 95%, 96%, 97%, 98%, or 99% sequence identity to the amino acid sequence of SEQ ID NO:20; and (b) a second antigen-binding domain that comprises a HCVR having at least 90%, 91%, 92%, 93%, 94%, 95%, 96%, 97%, 98%, or 99% sequence identity to the amino acid sequence of SEQ ID NO: 36 and a LCVR having at least 90%, 91%, 92%, 93%, 94%, 95%, 96%, 97%, 98%, or 99% sequence identity to the amino acid sequence of SEQ ID NO:20. In some embodiments, the anti-BCMA/anti-CD3 bispecific antibody or antigen-binding fragment thereof comprises: (a) a first antigen-binding domain that comprises three HCDRs (HCDR1, HCDR2 and HCDR3) comprising the amino acid sequences of SEQ ID NOs:14, 16, and 18, respectively, and a HCVR having at least 90%, 91%, 92%, 93%, 94%, 95%, 96%, 97%, 98%, or 99% sequence identity to the amino acid sequence of SEQ ID NO: 12, and comprises three LCDRs (LCDR1, LCDR2 and LCDR3) comprising the amino acid sequences of SEQ ID NOs:22, 24, and 26, respectively, and a LCVR having at least 90%, 91%, 92%, 93%, 94%, 95%, 96%, 97%, 98%, or 99% sequence identity to the amino acid sequence of SEQ ID NO:20; and (b) a second antigen-binding domain that comprises three HCDRs (HCDR1, HCDR2 and HCDR3) comprising the amino acid sequences of SEQ ID NOs:38, 40, and 42, respectively, and a HCVR having at least 90%, 91%, 92%, 93%, 94%, 95%, 96%, 97%, 98%, or 99% sequence identity to the amino acid sequence of SEQ ID NO: 36, and comprises three LCDRs (LCDR1, LCDR2 and LCDR3) comprising the amino acid sequences of SEQ ID NOs:22, 24, and 26, respectively, and a LCVR having at least 90%, 91%, 92%, 93%, 94%, 95%, 96%, 97%, 98%, or 99% sequence identity to the amino acid sequence of SEQ ID NO:20.

The present disclosure also includes use of anti-BCMA/anti-CD3 antibodies in methods to treat allergy, wherein the antibodies comprise variants of any of the HCVR, LCVR and/or CDR amino acid sequences disclosed herein having one or more conservative amino acid substitutions. For example, the present disclosure includes use of anti-BCMA/anti-CD3 antibodies having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein. In some embodiments, the disclosure includes use of an anti-BCMA/anti-CD3 antibody having HCVR, LCVR and/or CDR amino acid sequences with 1, 2, 3, or 4 conservative amino acid substitutions relative to any of the HCVR, LCVR and/or CDR amino acid sequences disclosed herein.

Other anti-BCMA/anti-CD3 antibodies that can be used in the context of the methods of the present disclosure include, e.g., the antibodies referred to and known in the art as AMG420, AMG701, CC-93269, EM801, JNJ-64007957, and TN B384B, or any of the anti-BCMA/anti-CD3 antibodies set forth, e.g., in patent publications WO2013/072415, WO2014/140248, WO2014/122144, WO2016/166629, WO2016/079177, WO2016/020332, WO2017031104, WO2017/223111, WO2017/134134, WO2018/083204, WO2018/201051. The portions of the publications cited herein that identify anti-BCMA/anti-CD3 antibodies are hereby incorporated by reference.

IgE Depletion in Combination with Allergen Immunotherapy

The present disclosure also provides methods for enhancing the efficacy and/or tolerability of an immunotherapy regimen (e.g., an allergen-specific immunotherapy regimen) in a subject having an allergy. In some embodiments, the method comprises administering to a subject having an allergy an IL-4/IL-13 pathway inhibitor (such as an anti-IL-4R antibody) and a plasma cell ablating agent (such as an anti-BCMA/anti-CD3 antibody) prior to or concurrent with the immunotherapy regimen.

In some embodiments, the subject to be treated has a food allergy. For example, in some embodiments, the subject has an allergy to milk, a dairy product, egg, celery, sesame, wheat, meat, fruit, soy, fish, shellfish, a sugar, peanut, a legume, a tree nut, or a combination thereof. In some embodiments, the subject has a peanut allergy. In some embodiments, the subject to be treated has a non-food allergy (e.g., an allergy to an environmental allergen). For example, in some embodiments, the subject has an allergy to a non-food allergen selected from the group consisting of dust, dust mite, pollen, insect venom, mold, animal fur, animal dander, wool, latex, a metal, a household cleaner, a detergent, medication, cosmetics, perfumes, a drug such as penicillin, sulfonamides, or salicylate, therapeutic monoclonal antibodies (e.g., cetuximab), ragweed, grass and birch. In some embodiments, the subject to be treated has a severe allergy (e.g., a severe food allergy or a severe non-food allergy).

As used herein, "allergen-specific immunotherapy" refers to the repeated administration of an allergen (e.g., an allergen as disclosed herein) to a subject over time as a means for treating or preventing allergies and allergic reactions, or to reduce to eliminate allergic responses. In some embodiments, the allergen-specific immunotherapy regimen comprises oral immunotherapy. In some embodiments, the allergen-specific immunotherapy regimen comprises subcutaneous immunotherapy. In some embodiments, the allergen-specific immunotherapy regimen comprises sublingual immunotherapy. In general, the immunotherapy regimen can be a "conventional" immunotherapy regimen or an "accelerated" immunotherapy regimen. Typically, in a conventional immunotherapy regimen, increasing doses of the allergen (also referred to as "up-titration") are administered to the patient at weekly intervals over the course of several weeks to months (e.g., over 1, 2, 3, 4, 5, 6, 7, 8, 9, 10, 11, 12 months or longer), under tightly monitored medical supervision, followed by a maintenance regimen, which typically comprises administering one or more doses of the allergen at the highest dose administered during the up-titration regimen. In an accelerated immunotherapy regimen, the up-titration schedule is accelerated as compared to conventional immunotherapy. Examples of accelerated immunotherapy include "rush" immunotherapy and "cluster" immunotherapy. In rush immunotherapy, typically increasing dosages of the allergen are administered per day over several consecutive days (e.g., over 2 days, 3 days, 4 days, 5 days, 6 days, or one week) until the maximum tolerated dose is reached. In cluster immunotherapy, typically several (e.g., 2-3) increasing dosages of the allergen are administered in a single day, over nonconsecutive days until the maximum tolerated dose is reached, usually within 4 to 8 weeks.

In some embodiments, an IL-4/IL-13 pathway inhibitor and a plasma cell ablating agent are administered prior to or concurrent with an allergen-specific immunotherapy regimen as disclosed herein (e.g., oral, sublingual, or subcutaneous immunotherapy, which can be conventional or accelerated immunotherapy). In some embodiments, the plasma cell ablating agent (e.g., 1, 2, 3, 4, 5 or more doses) is administered prior to the onset of the immunotherapy regimen. In some embodiments, the IL-4/IL-13 pathway inhibitor (e.g., 1, 2, 3, 4, 5 or more doses) is administered prior to the onset of the immunotherapy regimen. In some embodiments, at least one dose of each of the plasma cell ablating agent and the IL-4/IL-13 pathway inhibitor are administered prior to the onset of the immunotherapy regimen. In some embodiments, the IL-4/IL-13 pathway inhibitor is administered concurrent with the immunotherapy regimen. In some embodiments, the plasma cell ablating agent is administered concurrent with the immunotherapy regimen.

Pharmaceutical Compositions and Administration

The disclosed methods comprise administering an IL-4/IL-13 pathway inhibitor in combination with a plasma cell ablating agent to a subject in need thereof, wherein the inhibitors are contained within separate pharmaceutical compositions or a combined (single) pharmaceutical composition. The pharmaceutical compositions of the disclosure may be formulated with pharmaceutically acceptable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al., 1998, *J Pharm Sci Technol*, 52:238-311.

In certain embodiments, the pharmaceutical compositions of the disclosure comprise a therapeutically effective amount of an IL-4/IL-13 pathway inhibitor (such as an anti-IL-4R antibody) and/or a therapeutically effective amount of a plasma cell ablating agent (such as an anti-BCMA/anti-CD3 antibody) and a pharmaceutically acceptable carrier. In certain embodiments, the disclosed pharmaceutical compositions are formulated for administration by injection, such as intravenous injection.

Various delivery systems are known and can be used to administer the pharmaceutical compositions of the present disclosure, e.g., encapsulation in liposomes, microparticles, microcapsules, recombinant cells capable of expressing the mutant viruses, receptor mediated endocytosis (see, e.g., Wu et al., 1987, *J. Biol. Chem.* 262: 4429-4432). Methods of administration include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. In some embodiments, the IL-4/IL-13 pathway inhibitor and/or the plasma cell ablating agent is administered intravenously. In some embodiments, the IL-4/IL-13 pathway inhibitor and/or the plasma cell ablating agent is administered subcutaneously.

In some embodiments, a pharmaceutical composition of the present disclosure is contained within a container. Thus, in another aspect, containers comprising a pharmaceutical composition as disclosed herein are provided. For example, in some embodiments, a pharmaceutical composition is contained within a container selected from the group consisting of a glass vial, a syringe, a pen delivery device, and an autoinjector.

In some embodiments, a pharmaceutical composition of the present disclosure is delivered subcutaneously or intravenously with a standard needle and syringe. In some embodiments, the syringe is a pre-filled syringe. In addition, with respect to subcutaneous delivery, a pen delivery device or autoinjector readily has applications in delivering a pharmaceutical composition of the present disclosure. A pen delivery device can be reusable or disposable. Typically, a reusable pen delivery device utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Examples of suitable pen and autoinjector delivery devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™ OPTIPEN STARLET™, and OPTICLIK™ (sanofi-aventis, Frankfurt, Germany). Examples of disposable pen delivery devices having applications in subcutaneous delivery of a pharmaceutical composition of the present disclosure include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.), and the HUMIRA™ Pen (Abbott Labs, Abbott Park IL).

In certain situations, one or both pharmaceutical compositions can be delivered in a controlled release system. In one embodiment, a pump may be used. In another embodiment, polymeric materials can be used. See, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, MEDICAL APPLICATIONS OF CONTROLLED RELEASE, vol. 2, pp. 115-138). Other controlled release systems are discussed in Langer, 1990, *Science* 249:1527-1533.

Suitable injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

In some embodiments, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), cartridges, suppositories, etc.

Injectable formulations of the pharmaceutical compositions may be prepared by known methods. For example, the injectable formulation may be prepared, e.g., by dissolving, suspending or emulsifying the inhibitor (e.g., an anti-IL-4R antibody) or a salt thereof in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injectable formulation thus prepared is preferably filled in an appropriate injection ampoule. In some embodiments, an injectable formulation may include a concentration of the inhibitor (e.g., an anti-IL-4R antibody) and one or more pharmaceutically acceptable solvents (e.g., distilled water, saline, etc.).

Exemplary pharmaceutical compositions comprising an anti-IL-4R antibody that can be used in the context of the present disclosure are disclosed, e.g., in U.S. Pat. No. 8,945,559, the portions of which that identify pharmaceutical compositions comprising an anti-IL-4R antibody are hereby incorporated by reference.

Kits

In certain embodiments, the present disclosure provides for pharmaceutical combinations and kits comprising an IL-4/IL-13 pathway inhibitor as disclosed herein and a plasma cell ablating agent as disclosed herein. In some embodiments, the combination or kit comprises an anti-IL-4R antibody as disclosed herein (e.g., an anti-IL-4R antibody or antigen-binding fragment thereof comprising a HCDR1, HCDR2, and HCDR3 comprising the amino acid sequences of SEQ ID NOs:3, 4, and 5, respectively, and a LCDR1, LCDR2, and LCDR3 comprising the amino acid sequences of SEQ ID NOs:6, 7, and 8, respectively) and a plasma cell ablating agent as disclosed herein (e.g., an anti-BCMA/anti-CD3 bispecific antibody, comprising a first antigen binding domain that binds specifically to BCMA; and a second antigen-binding domain that binds specifically to CD3, wherein the first antigen-binding domain comprises a HCDR1, HCDR2, and HCDR3 comprising the amino acid sequences of SEQ ID NOs:14, 16, and 18, respectively, and a LCDR1, LCDR2, and LCDR3 comprising the amino acid sequences of SEQ ID NOs:22, 24, and 26, respectively; and wherein the second antigen-binding domain comprises a HCDR1 comprising the amino acid sequence of SEQ ID NO: 30 or 38, a HCDR2 comprising the amino acid sequence of SEQ ID NO: 32 or 40, a HCDR3 comprising the amino acid sequence of SEQ ID NO: 34 or 42, and a LCDR1, LCDR2, and LCDR3 comprising the amino acid sequences of SEQ ID NOs:22, 24, and 26, respectively.

In some embodiments, the combination or kit comprising an IL-4/IL-13 pathway inhibitor and a plasma cell ablating agent is for use in a method as disclosed herein. In some embodiments, the combination or kit is for use in treating an allergy or allergic disorder or for reducing or eliminating allergen-specific serum IgE in a subject. In some embodiments, the combination or kit further comprises one or more additional therapeutic agents as disclosed herein.

In some embodiments, the combination or kit comprising an IL-4/IL-13 pathway inhibitor and a plasma cell ablating agent is for use in increasing the efficacy and/or tolerability of an immunotherapy regimen in a subject having an allergy. Thus, in some embodiments, the combination or kit further comprises one or more reagents for an immunotherapy regimen.

In some embodiments, a kit for use as disclosed herein further comprises instructions for use. In some embodiments, a kit for use as disclosed herein comprises one or more containers comprising the IL-4/IL-13 pathway inhibitor and the plasma cell ablating agent. In some embodiments, the kit comprises a first container comprising the IL-4/IL-13 pathway inhibitor and a second container comprising the plasma cell ablating agent.

Administration Regimens

In some embodiments, the disclosed methods include sequentially administering a therapeutically effective amount of an IL-4/IL-13 pathway inhibitor in combination with a therapeutically effective amount of a plasma cell ablating agent to a subject in need thereof, wherein each therapeutic agent is administered to the subject in one or more doses, e.g., as part of a specific therapeutic dosing regimen. In certain embodiments, the methods of the present disclosure comprise administering the inhibitors for additive or synergistic activity to treat an allergic disease or disorder, a mast cell activation disorder or mastocytosis.

As used herein, "sequentially administering" means that each dose of inhibitor is administered to the subject at a different point in time, e.g., on different days separated by a predetermined interval (e.g., hours, days, weeks or months). In some embodiments, the disclosed methods include sequentially administering to the subject a single initial dose of an IL-4/IL-13 pathway inhibitor, followed by one or more subsequent doses of the IL-4/IL-13 pathway inhibitor. In certain embodiments, the methods further comprise sequentially administering to the subject a single initial dose of a plasma cell ablating agent, followed by one or more subsequent doses of the plasma cell ablating agent.

In some embodiments, the therapeutic dosing regimen comprises administering one or more doses of an IL-4/IL-13 pathway inhibitor in combination with one or more doses of a plasma cell ablating agent. In certain embodiments, the one or more doses of an IL-4/IL-13 pathway inhibitor and/or the one or more doses of a plasma cell ablating agent are administered to the subject at a frequency of about once a day, once every two days, once every three days, once every four days, once every five days, once every six days, once a week, once every two weeks, once every three weeks, once every four weeks, once a month, once every two months, once every three months, once every four months, or less frequently.

As used herein, the expression "in combination with" means that the IL-4/IL-13 pathway inhibitor is administered before, after, or concurrent with the plasma cell ablating agent. The term "in combination with" also includes sequential or concomitant administration of an IL-4/IL-13 pathway inhibitor and a plasma cell ablating agent.

For example, when the IL-4/IL-13 pathway inhibitor is administered "before" the plasma cell ablating agent, the IL-4/IL-13 pathway inhibitor may be administered more than 150 hours, about 150 hours, about 100 hours, about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, or about 15 minutes prior to the administration of the plasma cell ablating agent. When the IL-4/IL-13 pathway inhibitor is administered "after" the plasma cell ablating agent, the IL-4/IL-13 pathway inhibitor may be administered about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, about 72 hours, or more than 72 hours after the administration of the plasma cell ablating agent. Administration of the IL-4/IL-13 pathway inhibitor "concurrent" with the plasma cell ablating agent means that the IL-4/IL-13 pathway inhibitor is administered to the subject in a separate dosage form within 10 minutes (before, after, or at the same time) of administration of the plasma cell ablating agent, or administered to the subject as a single combined dosage formulation comprising both the IL-4/IL-13 pathway inhibitor and the plasma cell ablating agent.

As used herein, an "initial dose" is a dose that is administered at the beginning of the treatment regimen (also referred to as a "baseline dose"). The one or more subsequent doses administered after the initial dose may all contain the same amount of the IL-4/IL-13 pathway inhibitor or the plasma cell ablating agent. In certain embodiments, however, the amount contained in the initial, and subsequent doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an IL-4/IL-13 pathway inhibitor or plasma cell ablating agent may be administered to a patient with an allergic disease at a loading dose of about 1 mg/kg to about 20 mg/kg followed by one or more maintenance doses of about 0.1 mg/kg to about 10 mg/kg of the patient's body weight.

In one exemplary embodiment of the present disclosure, each subsequent dose is administered ½ to 14 weeks or more (e.g., ½, 1, 1½, 2, 2½, 3, 3½, 4, 5, 5½, 6, 6½, 7, 7½, 8, 8½, 9, 9½, 10, 10½ or more weeks) after the immediately preceding dose. The phrase "the immediately preceding dose," as used herein, means, in a sequence of multiple administrations, the dose of each inhibitor administered to a subject prior to administration of the next dose in the sequence with no intervening doses.

Dosage

In certain embodiments, at least one dose of the IL-4/IL-13 pathway inhibitor comprises about 0.1-50 mg/kg, such as about 0.1-10 mg/kg, of the subject's body weight. For example, at least one dose may comprise about 0.1, 1, 0.3, 3, 4, 5, 6, 7, 8, 9 or 10 mg/kg of the subject's body weight. In certain embodiments, at least one dose of the IL-4/IL-13 pathway inhibitor comprises about 0.05-600 mg of the IL-4/IL-13 pathway inhibitor, e.g., about 5-600 mg, about 10-300 mg, about 50-600 mg, or about 50-300 mg, such as about 5, 10, 15, 20, 25, 40, 45, 50, 60, 70, 80, 90, 100, 200, 300, 400 mg, 500 mg, 600 mg or more of the IL-4/IL-13 pathway inhibitor. In one embodiment, the IL-4/IL-13 pathway inhibitor is REGN668 (dupilumab).

In certain embodiments, at least one dose of the plasma cell ablating agent comprises about 0.1-20 mg/kg of the subject's body weight, such as about 0.1, 1, 0.3, 3, 4, 5, 6, 7, 8, 9 or 10 mg/kg of the subject's body weight. In certain embodiments, at least one dose of the plasma cell ablating agent comprises about 0.05-500 mg of the plasma cell ablating agent, such as about 5, 10, 15, 20, 25, 40, 45, 50, 60, 70, 80, 90, 100 mg or more of the plasma cell ablating agent. In one embodiment, the plasma cell ablating agent is an anti-BCMA/anti-CD3 bispecific antibody (such as REGN5459). In one embodiment, the plasma cell ablating agent is a proteasome inhibitor such as bortezomib.

The amounts of IL-4/IL-13 pathway inhibitor and plasma cell ablating agent administered to a subject according to the methods disclosed herein is a therapeutically effective amount. As used herein, the term "therapeutically effective amount" means an amount of each therapeutic agent that results in one or more of: (a) a reduction in the severity or duration of a symptom or an indication of an allergy—e.g., anaphylaxis; (b) reduction in the level of serum allergen-specific IgE; (c) elimination of serum IgE in the subject; (d) reduction of allergen sensitization; (e) reduction in susceptibility to an allergic reaction and/or (f) a reduction in the use or need for conventional anti-allergy therapy (e.g., reduced or eliminated use of corticosteroids) as compared to an untreated subject or a subject treated with either therapeutic agent as monotherapy.

In the case of an IL-4/IL-13 pathway inhibitor (e.g., anti-IL-4R antibody), a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the IL-4/IL-13 pathway inhibitor. In certain embodiments, 10 mg, 25 mg, 50 mg, 75 mg, 150 mg, or 300 mg of an IL-4/IL-13 pathway inhibitor is administered to a subject.

In the case of a plasma cell ablating agent (e.g., an anti-BCMA/anti-CD3 bispecific antibody), a therapeutically effective amount can be from about 0.05 mg to about 500 mg, from about 1 mg to about 500 mg, from about 10 mg to about 450 mg, from about 50 mg to about 400 mg, from about 75 mg to about 350 mg, or from about 100 mg to about 300 mg of the antibody. For example, in various embodiments, the amount of the plasma cell ablating agent is about 0.05 mg, about 0.1 mg, about 1.0 mg, about 1.5 mg, about 2.0 mg, about 5 mg, about 10 mg, about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg, of the plasma cell ablating agent.

In certain embodiments, an individual dose amount of an IL-4/IL-13 pathway inhibitor (e.g., an anti-IL-4R antibody) and/or a plasma cell ablating agent (e.g., an anti-BCMA/anti-CD3 antibody) administered to a subject may be less than a therapeutically effective amount, i.e., a subtherapeutic dose. For example, if the therapeutically effective amount of an inhibitor comprises 3 mg/kg, a subtherapeutic dose comprises an amount less than 3 mg/kg, e.g., 2 mg/kg, 1.5 mg/kg, 1 mg/kg, 0.5 mg/kg or 0.3 mg/kg. As defined herein, a "subtherapeutic dose" refers to an amount of the inhibitor that does not lead to a therapeutic effect by itself. However, in certain embodiments, multiple subtherapeutic doses of the inhibitor may be administered to collectively achieve a therapeutic effect in the subject.

EXAMPLES

The disclosed technology is next described by means of the following examples. The use of these and other examples anywhere in the specification is illustrative only, and in no way limits the scope and meaning of the disclosure or of any exemplified form. Likewise, the disclosure is not limited to any particular preferred embodiments described herein. Indeed, modifications and variations of the disclosure may be apparent to those skilled in the art upon reading this specification and can be made without departing from its spirit and scope. The disclosure is therefore to be limited only by the terms of the claims, along with the full scope of equivalents to which the claims are entitled. Also, while efforts have been made to ensure accuracy with respect to numbers used (e.g., amounts, temperature, etc.), some experimental errors and deviations should be accounted for. Unless indicated otherwise, parts are parts by weight, molecular weight is average molecular weight, temperature is in degrees Centigrade, and pressure is at or near atmospheric.

Example 1: Effect of an Anti-IL-4R Antibody in Combination with an Anti-BCMA/Anti-CD3 Bispecific Antibody This example relates to a study that demonstrates the enhanced efficacy of an IL-4/IL-13 pathway inhibitor in combination with a plasma cell ablating agent in blocking IgE production in a mouse model of chronic allergen-driven lung inflammation.

The IL-4/IL-13 pathway inhibitor used in this example was a mouse anti-IL-4R antibody identified as REGN1103, which is a mouse surrogate antibody of a human monoclonal antibody identified as REGN668 (also known as dupilumab) directed to human IL-4R. REGN1103 comprises a HCVR/LCVR amino acid sequence pair of SEQ ID NOs: 43/44 and has an affinity for mouse IL-4R that is in a similar range as the affinity of dupilumab for human IL-4R. In addition, REGN1103 inhibits IL-4- and IL-13-dependent proliferation of cell lines at IC50s of 1.9 nM and 11 pM, respectively.

The plasma cell ablating agent used in this example was an anti-BCMA/anti-CD3 bispecific antibody REGN5459, that comprises an anti-BCMA binding domain comprising a HCVR of SEQ ID NO: 12 and a LCVR of SEQ ID NO: 20; and an anti-CD3 binding domain comprising a HCVR of SEQ ID NO: 36 and a LCVR of SEQ ID NO: 20.

Materials and Methods

To determine the effect of combining anti-IL-4Rα and anti-BCMA×anti-CD3 on IgE production in a relevant in vivo model, a chronic house dust mite (HDM) driven lung inflammation study was conducted in mice that were homozygous for human BCMA and human CD3 in place of mouse BCMA and CD3. Chronic lung inflammation and persistent IgE production was induced by exposing mice to 25 pg of HDM (Greer, Catalog #XPB70D3A25) diluted in 20 μL of saline (Sigma, Catalog #S8776) or 20 μL of saline (control group) intranasally (i.n.) three times a week for 11 weeks. This model induces class switching of B cells into IgE producing plasma cells in secondary lymphoid organs and drives accumulation of IgE plasma cells in the bone marrow. At week 8 after the first HDM administration, a subset of mice started receiving subcutaneous injections of 25 mg/kg REGN1103 (anti-IL-4Rα) or 25 mg/kg isotype control until the end of the experiment. At week 11, two doses of REGN5459 (anti-BCMA×anti-CD3) or two doses of an isotype control antibody were administered subcutaneously and mice were rested in the absence of i.n. HDM for 9 weeks. Details of HDM exposure and antibody treatment protocol is outlined in Table 1 and FIG. 1.

TABLE 1

| | HDM exposure and antibody treatment protocol for mice | | | |
|---|---|---|---|---|
| Group | BCMA × CD3 humanized mice | Intranasal (i.n.) (11 weeks) | Rest | Antibody (2× weekly after week 8) | Antibody (2 doses at week 11) |
| A | 8 | Saline | 9 wks | None | None |
| B | 9 | HDM | 9 wks | None | None |
| C | 10 | HDM | 9 wks | Isotype control | Isotype control |
| D | 8 | HDM | 9 wks | Isotype control | REGN5459 (anti-BCMA × anti-CD3) |
| E | 9 | HDM | 9 wks | REGN1103 (anti-IL-4Rα) | Isotype control |
| F | 9 | HDM | 9 wks | REGN1103 (anti-IL-4Rα) | REGN5459 (anti-BCMA × anti-CD3) |

1 week and 6 weeks after the last dose of HDM, ~100 μL of blood was collected from all groups of mice by retro-orbital bleeding and transferred into microtainer tubes (BD, Catalog #365967) for serum isolation. The total IgE concentration in serum was determined using an OptEIA™ ELISA kit (BD Biosciences, #555248) following manufacturer's instructions. Briefly, ELISA plates were coated with IgE capture antibody diluted in coating buffer (carbonate-bicarbonate buffer, Sigma; catalog #C3041, diluted in 100 mL distilled water, Gibco; catalog #15230-270) overnight at 4°. Coated plates were washed 4× in wash buffer (0.05% Tween 20, Sigma; catalog #P1379 diluted in DPBS, GE; catalog #SH3001304). Plates were blocked with Assay Diluent (BD; catalog #555213) for 1 hour at room temperature (RT). 100 μL of serum samples diluted at a starting concentration of 1:50 or 1:100 with further 3-fold serial dilutions and IgE standard diluted at a starting concentration of 100 ng/mL with further 2-fold serial dilution was added to plates and incubated for 2 hrs at RT. Plates were then washed 4× in wash buffer and incubated in 100 μL working detector (detection antibody with sAv-HRP) for 1 hr at RT. Plates were washed 7×, soaked in wash buffer for 5 min and washed again 4× to remove unbound detection antibody. 100 μL of TMB Substrate Solution (BD; catalog #555214) was added to each sample and plates were incubated in the dark for 30 min followed by addition of 50 μL Stop Solution (2N Sulfuric Acid, BDH VWR analytical; catalog #BDH7500). Absorbance was measured at 450 nm and IgE concentrations were calculated from a standard curve. Serum IgE values are shown as ng/mL Statistical significance was determined by Kruskal-Wallis test with Dunn's post-hoc multi-comparison test in GraphPad Prism.

Results

Figure 2A:
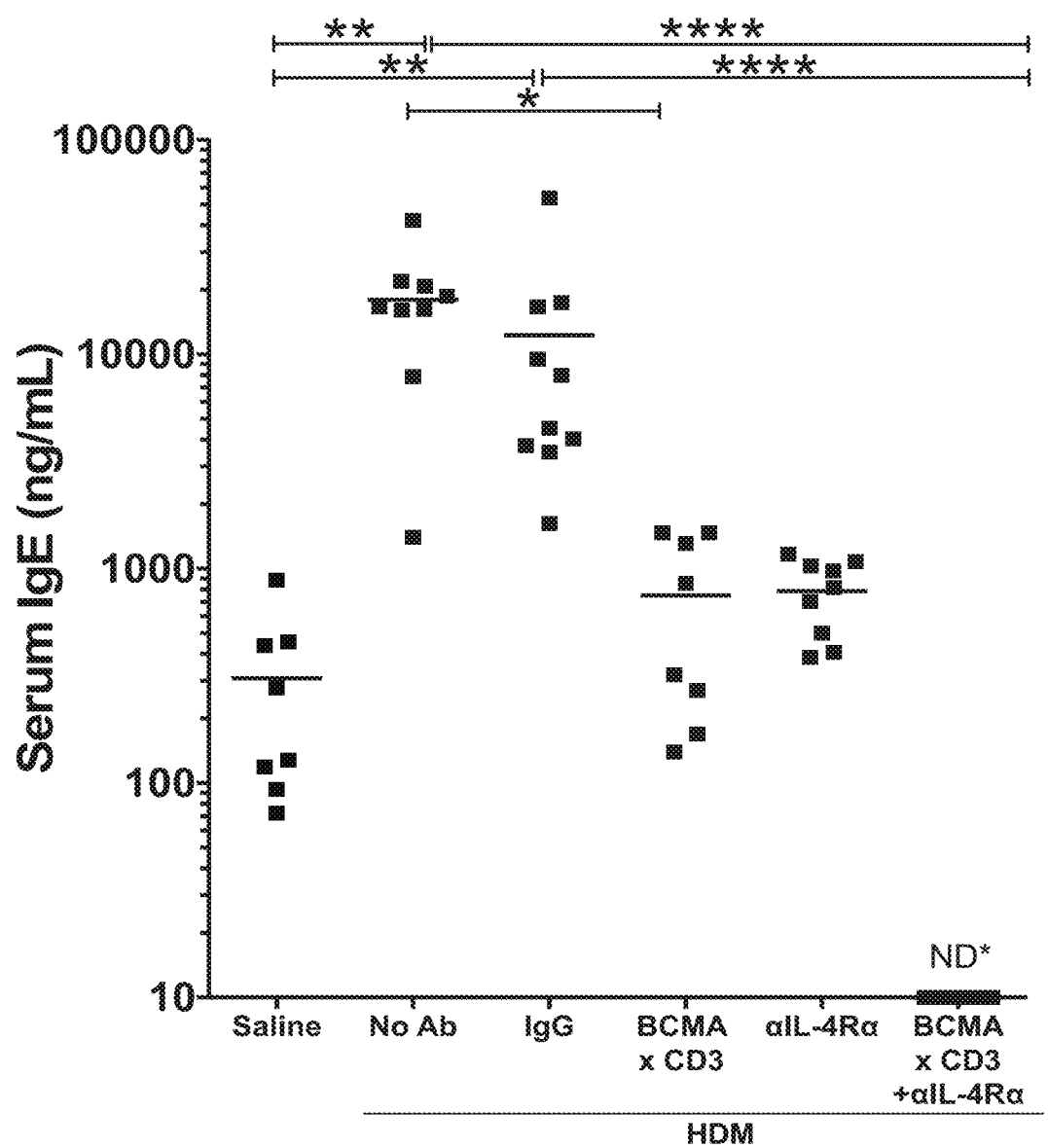
FIG. 2A shows serum IgE levels upon exposure to HDM for 11 weeks followed by 1-week rest in mice treated with either saline, no antibody, an isotype control antibody, REGN5459 (anti-BCMA×anti-CD3 bispecific antibody), REGN1103 (anti-IL-4R antibody), or a combination of REGN5459 and REGN1103 in accordance with the study described in Example 1. The asterisks (*) indicate degree of statistical significance relative to isotype controls (IgGs).
Figure 2B:
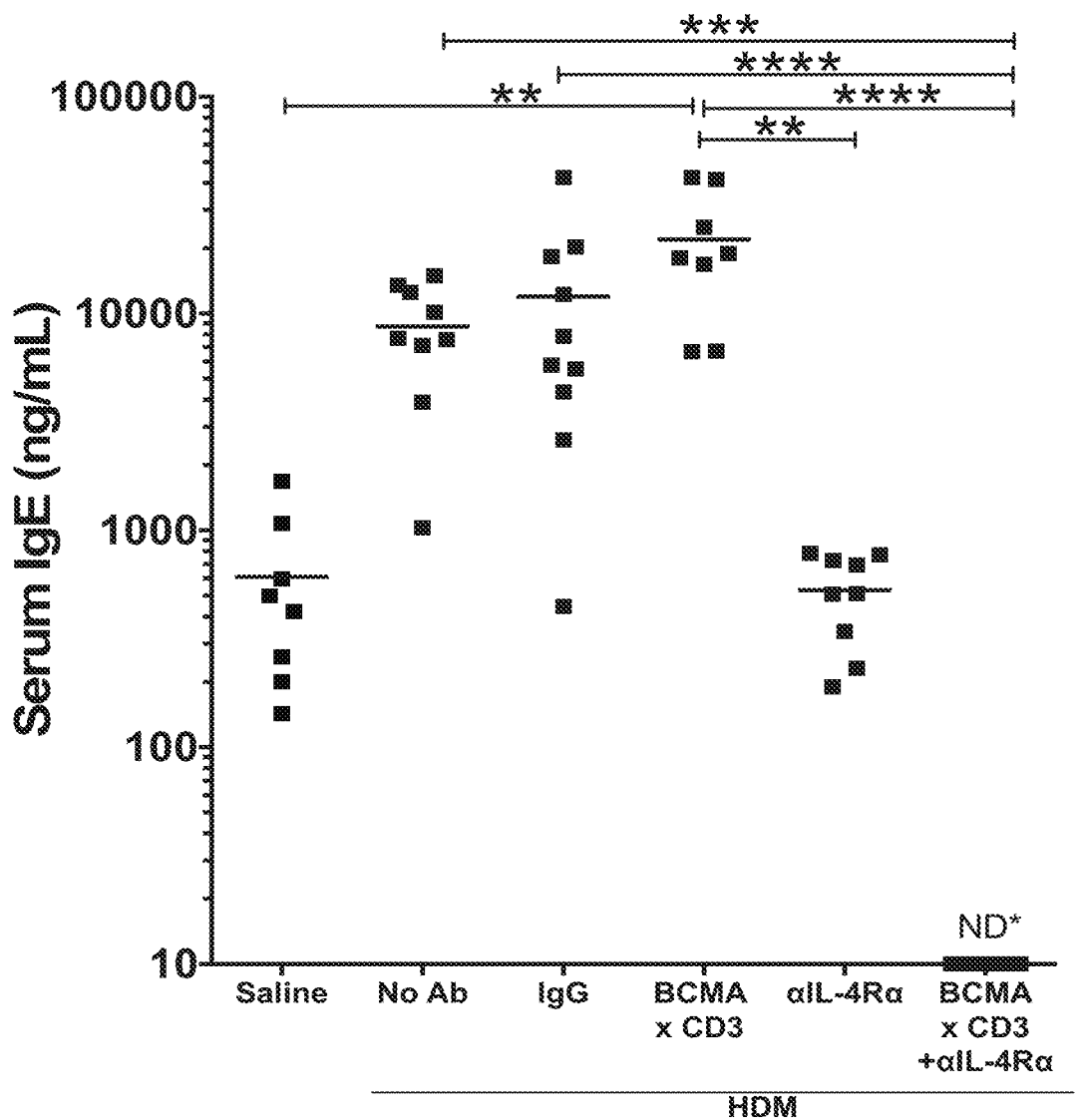
FIG. 2B shows serum IgE levels upon exposure to HDM for 11 weeks followed by 6 weeks rest in mice treated with either saline, no antibody, an isotype control antibody, REGN5459 (anti-BCMA×anti-CD3 bispecific antibody), REGN1103 (anti-IL-4R antibody), or a combination of REGN5459 and REGN1103 in accordance with the study described in Example 1. The asterisks (*) indicate degree of statistical significance relative to isotype controls (IgGs).

In a chronic HDM model, anti-IL4Rα treatment by itself reduced, but did not eliminate, circulating IgE (FIGS. 2A and 2B; Table 2).

efficacy of blocking IL-4Rα and depleting plasma cells with anti-BCMA×anti-CD3 as a successful strategy to block IgE production.

Example 2: Therapeutic Combination of a BCMA×CD3 Bispecific Antibody with an Anti-IL-4Rα Antibody Completely Blocks HDM-Specific IgE Production During Ongoing HDM Exposure This example demonstrates the efficacy of blocking IL-4R and depleting plasma cells in blocking allergen-specific IgE production even in the presence of continuous allergen exposure.

In this example, the IL-4/IL-13 pathway inhibitor that was used was the mouse anti-IL-4R antibody REGN1103, which is a mouse surrogate antibody of a human monoclonal antibody identified as REGN668 (also known as dupilumab) directed to human IL-4R. REGN1103 is described in Example 1 above. The plasma cell ablating agent that was used was the anti-BCMA×anti-CD3 bispecific antibody REGN5459, described in Example 1 above. A mouse IgG1 antibody (REGN1094) and a human IgG4×anti-CD3 antibody (REGN4460) were used as isotype controls.

Materials and Methods

To determine the effect of combining anti-IL-4Rα and anti-BCMA×anti-CD3 on IgE production in a relevant in vivo model, a chronic house dust mite (HDM) driven lung inflammation study was conducted in mice that were homozygous for human BCMA and human CD3 in place of mouse BCMA and CD3. Chronic lung inflammation and persistent IgE production was induced by exposing mice to 25 pg of HDM (Greer, Catalog #XPB70D3A25) diluted in 20 μL of saline (Sigma, Catalog #S8776) or 20 μL of saline (control group) intranasally (i.n.) three times a week for 19 weeks. This model induces class switching of B cells into

TABLE 2

Effect of anti-IL-4Rα and anti-BCMA × anti-CD3 antibody treatments on serum IgE in a chronic HDM model

| Group | Mean ± SD serum IgE (ng/mL) 1 wk rest | Mean rank difference compared to Isotype control 1 wk rest | Mean ± SD serum IgE in (ng/mL) 6 wks rest | Mean rank difference compared to Isotype control 6 wks rest |
|---|---|---|---|---|
| A (Saline) | 308.5 ± 277.4 (n = 8) | −25.58 (**) | 610.8 ± 524.9 (n = 8) | −18.85 |
| B (HDM) | 17981 ± 11162 (n = 9) | 3.578 | 8725 ± 4545 (n = 9) | 0.2333 |
| C (Isotype control) | 12279 ± 15582 (n = 10) | N/A | 11997 ± 12524 (n = 10) | N/A |
| D (anti-BCMA × anti-CD3) | 750.5 ± 596.1 (n = 8) | −18.45 | 21995 ± 13734 (n = 8) | 8.025 |
| E (anti-IL4Rα) | 786.1 ± 300.4 (n = 9) | −16.76 | 528.5 ± 231.6 (n = 9) | −17.99 |
| F (anti-BCMA × anti-CD3 + anti-IL-4Rα) | 0 ± 0 (n = 9) | −37.2 (**) | 0 ± 0 (n = 9) | −32.1 (**) |

Figure 3:
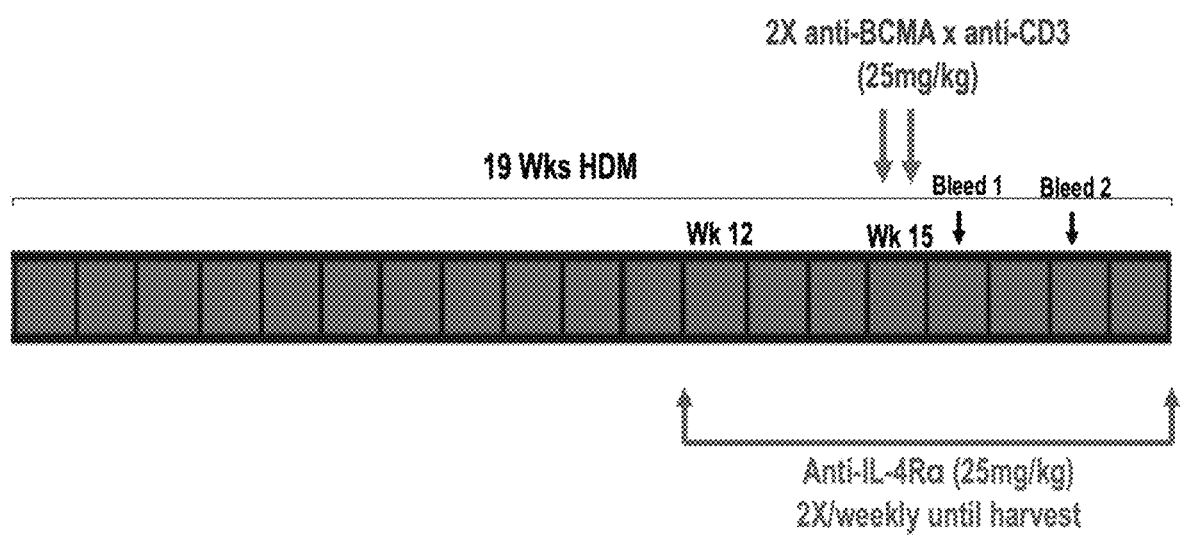
FIG. 3 is a diagrammatic representation of the HDM exposure and antibody treatment protocol in accordance with the study described in Example 2.

Anti-BCMA×anti-CD3 treatment alone transiently reduced IgE production, but serum IgE levels were restored after 6 weeks of rest (FIGS. 2A & 2B; Table 2). The combination of anti-IL-4Rα with anti-BCMA×anti-CD3 treatment eliminated serum IgE (undetectable by IgE ELISA) (FIGS. 2A & 2B; Table 2) demonstrating the IgE producing plasma cells in secondary lymphoid organs and drives accumulation of IgE plasma cells in the bone marrow. At week 12 after the first HDM administration, a subset of mice started receiving subcutaneous injections of 25 mg/kg REGN1103 (anti-IL-4Rα) or 25 mg/kg REGN1094 (isotype control) until the end of the experiment. At week 15, two doses of REGN5459 (anti-BCMA× anti-CD3) or two doses of REGN4460 (isotype control) were administered subcutaneously and mice were exposed to HDM for an additional 4 weeks. Details of HDM exposure and antibody treatment protocol are shown in Table 3 below and in FIG. 3.

TABLE 3

HDM exposure and antibody treatment protocol for mice in a chronic (19 weeks) HDM model

| Group | BCMA × CD3 humanized mice | Intranasal (i.n.) (11 weeks) | Antibody (2× weekly after week 8) | Antibody (2 doses at week 11) |
|---|---|---|---|---|
| A | 9 | Saline | None | None |
| B | 11 | HDM | None | None |
| C | 10 | HDM | REGN1094 (Isotype control) | REGN4460 (Isotype control) |
| D | 9 | HDM | REGN1094 (Isotype control) | REGN5459 (anti-BCMA × anti-CD3) |
| E | 11 | HDM | REGN1103 (anti-IL-4Rα) | REGN4460 (Isotype control) |
| F | 10 | HDM | REGN1103 (anti-IL-4Rα) | REGN5459 (anti-BCMA × anti-CD3) |

1 week, 3 weeks and 5 weeks after REGN5459 administration, ~100 µL of blood was collected from all groups of mice by retro-orbital bleeding and transferred into microtainer tubes (BD, Catalog #365967) for serum isolation. The HDM-specific IgE concentration in serum was determined using a Mouse Serum Anti-HDM IgE Antibody Assay kit (Chondrex catalog #3037) following manufacturer's instructions. Briefly, 100 µL of serum samples diluted at a concentration of 1:20 or 1:60, and HDM-IgE standard diluted at a starting concentration of 50 ng/mL with further 2-fold serial dilution was added to pre-coated plates provided with the kit and incubated at 4° C. overnight. Plates were then washed 3× in wash buffer and incubated in 100 µL of biotinylated HDM, provided with the kit. Plates were then washed 4× in wash buffer and incubated in 100 µL streptavidin peroxidase (provided with the kit) for 30 min at RT. Plates were washed 7× and 100 µL of TMB Substrate Solution (provided with the kit) was added to each sample and plates were incubated in the dark for 25 min followed by addition of 50 µL Stop Solution (2N Sulfuric Acid, provided with the kit). Absorbance was measured at 450 nm and HDM-IgE concentrations were calculated from a standard curve. Serum IgE values are shown as ng/mL. Lower Limit of Quantification (LLOQ) for HDM-Specific IgE ELISA was 15.62 ng/mL. Statistical significance was determined by Kruskal-Wallis test with Dunn's post-hoc multi-comparison test in Graph-Pad Prism.

Results

Figure 4A:
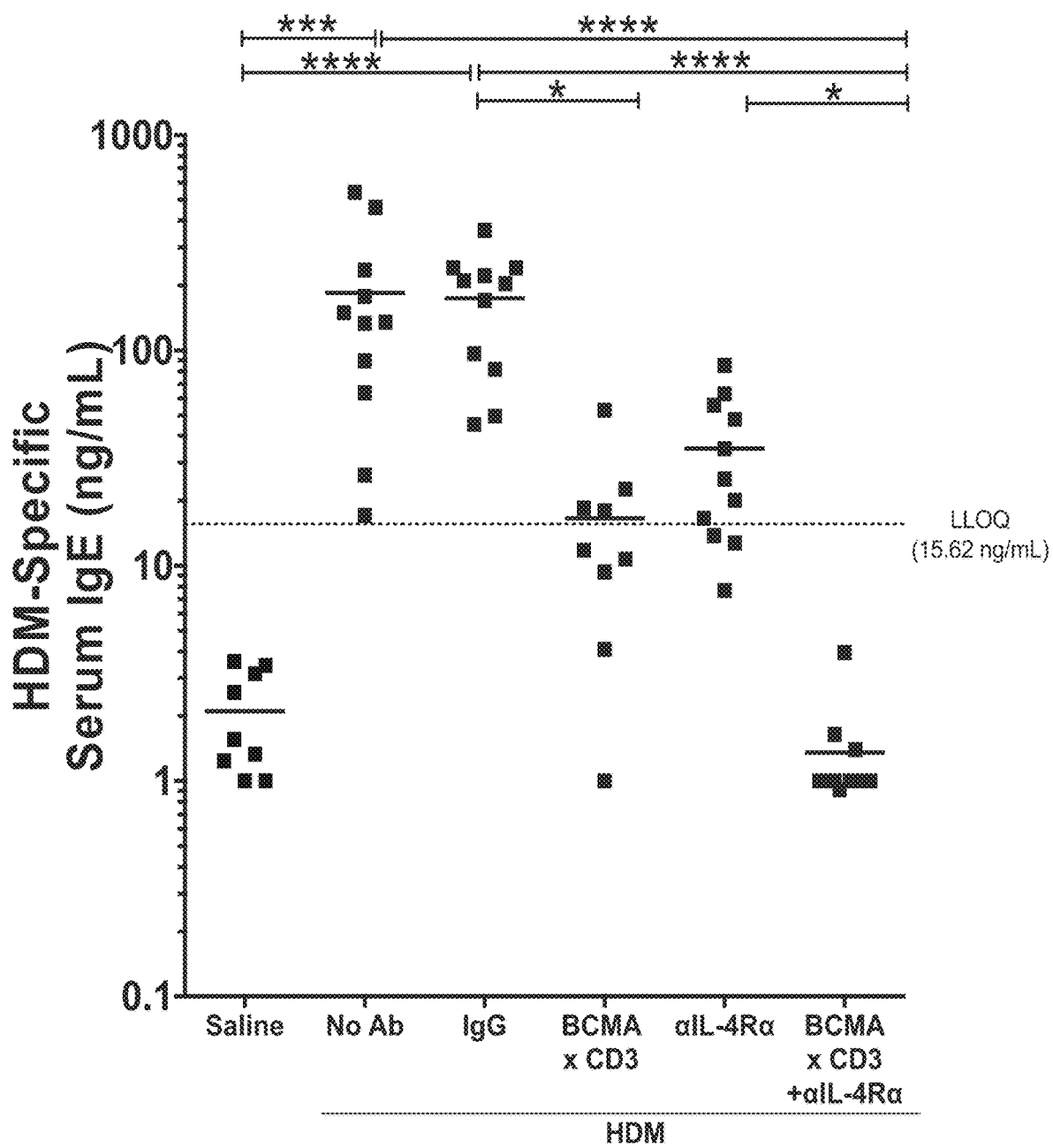
FIG. 4A shows HDM-specific serum IgE levels in mice subjected to ongoing exposure to HDM and 1 week post-treatment with an anti-BCMA×anti-CD3 bispecific antibody (REGN5459) or an isotype control (REGN4460), in accordance with the study described in Example 2. The asterisks (*) indicate degree of statistical significance relative to isotype controls (IgGs). LLOQ=lower limit of quantification.
Figure 4B:
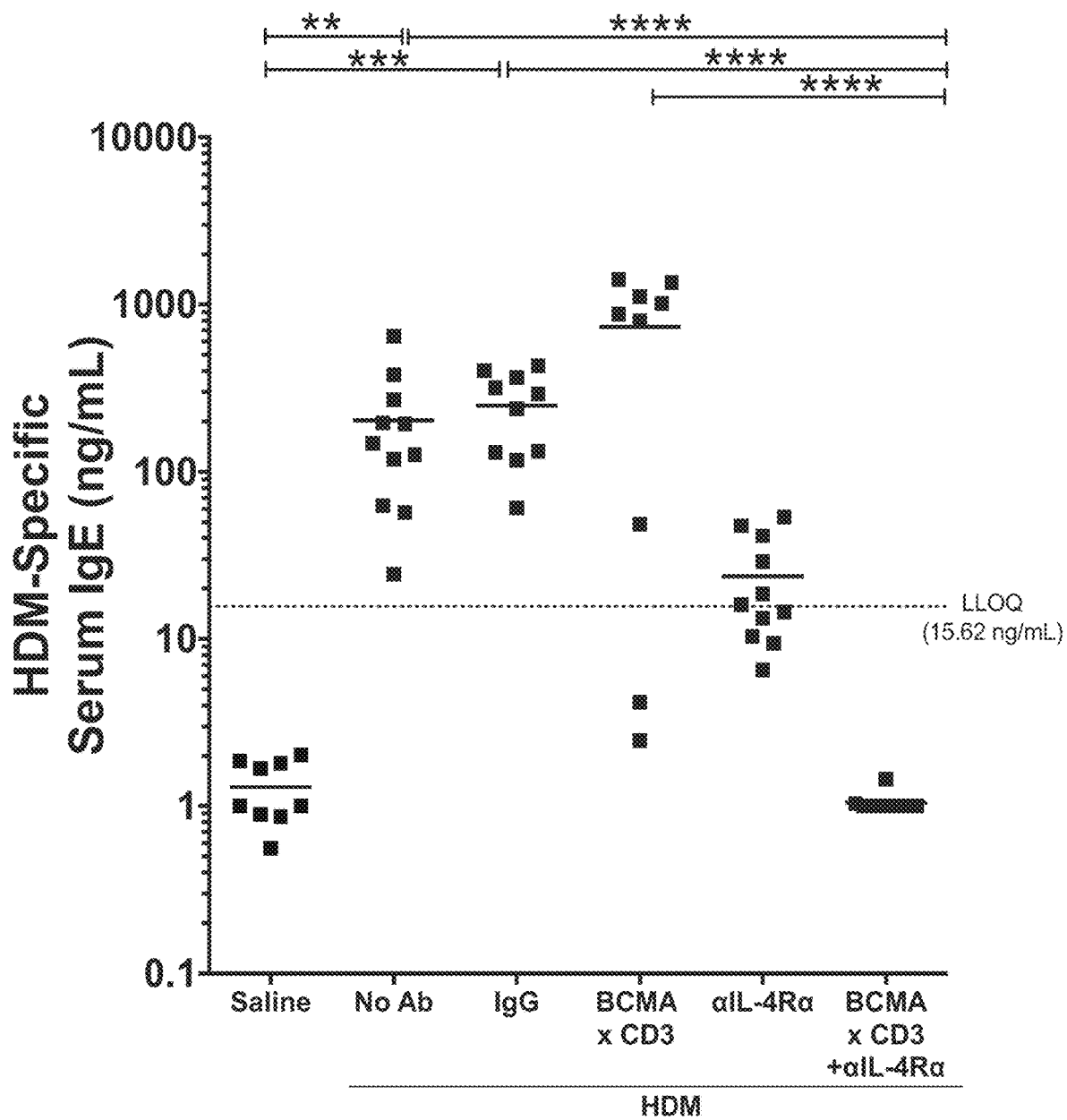
FIG. 4B shows HDM-specific serum IgE levels in mice subjected to ongoing exposure to HDM and 3 weeks post-treatment with an anti-BCMA×anti-CD3 bispecific antibody (REGN5459) or an isotype control (REGN4460), in accordance with the study described in Example 2. The asterisks (*) indicate degree of statistical significance relative to isotype controls (IgGs).
Figure 4C:
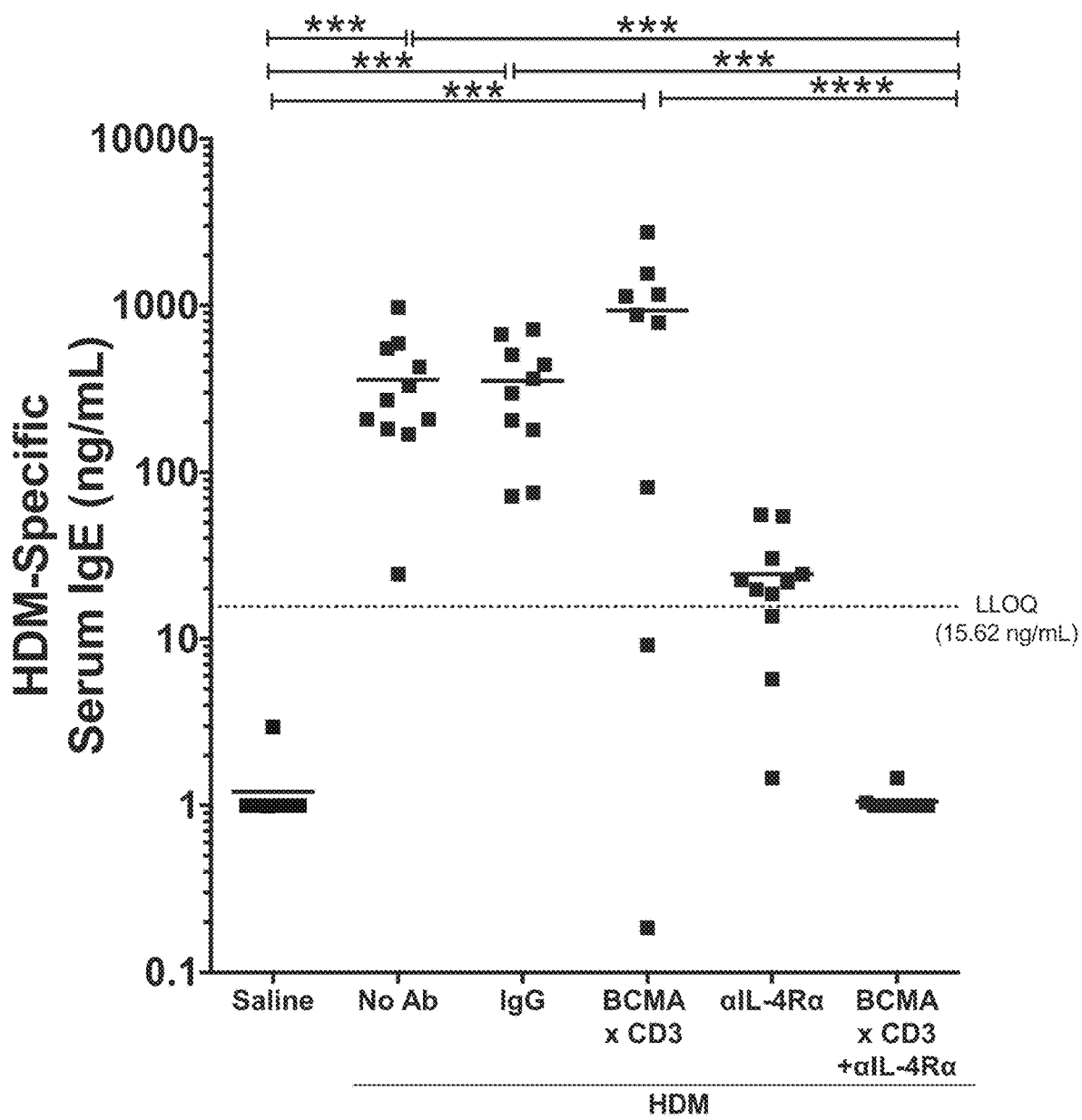
FIG. 4C shows HDM-specific serum IgE levels in mice subjected to ongoing exposure to HDM and 5 weeks post-treatment with an anti-BCMA×anti-CD3 bispecific antibody (REGN5459) or an isotype control (REGN4460), in accordance with the study described in Example 2. The asterisks (*) indicate degree of statistical significance relative to isotype controls (IgGs).

In a chronic HDM model, anti-IL4Rα treatment showed a trend towards reduced serum HDM-specific IgE levels that did not reach statistical significance, and this trend was maintained across the three time points examined (see, FIGS. 4A, 4B, and 4C and Table 4). Anti-BCMA×anti-CD3 treatment alone led to a significant reduction in circulating HDM-specific IgE relative to the isotype control group one week after REGN5459 administration (FIG. 4A), but this effect was short-lived and at 3 weeks or 5 weeks after bispecific administration the levels of HDM-specific IgE were not significantly different relative to the isotype control group (FIGS. 4B and 4C and Table 4). The combination of anti-IL-4Rα with anti-BCMA×anti-CD3 treatment eliminated serum HDM-specific IgE (undetectable by ELISA). This effect was maintained for the duration of the experiment (see, FIGS. 4A, 4B, and 4C and Table 4), demonstrating the efficacy of blocking IL-4Rα and depleting plasma cells with anti-BCMA×anti-CD3 as a successful strategy to block allergen-specific IgE production even in the presence of continuous allergen exposure.

TABLE 4

HDM-specific IgE at 1, 3, and 5 weeks post anti-BCMAxCD treatment

| Group | Mean ± SD serum IgE (ng/mL) 1 wk rest | Mean rank difference compared to Isotype control 1 wk post BCMA × CD3 | Mean ± SD serum IgE in (ng/mL) 3 wk post BCMA × CD3 | Mean rank difference compared to Isotype control 3 wk post BCMA × CD3 | Mean ± SD serum IgE in (ng/mL) 5 wk post BCMA × CD3 | Mean rank difference compared to Isotype control 5 wk post BCMA × CD3 |
|---|---|---|---|---|---|---|
| A (Saline) | Below LLOQ (n = 9) | −37.47 (**) | Below LLOQ (n = 9) | −32.61 (*) | Below LLOQ (n = 9) | −32.9 (***) |
| B (HDM) | 185.0 ± 170.7 (n = 11) | −2.273 | 202.3 ± 179.4 (n = 11) | −3.318 | 357.9 ± 264.9 (n = 11) | −0.2636 |
| C (Isotype control) | 175.0 ± 97.56 (n = 11) | N/A | 248.7 ± 131.8 (n = 10) | N/A | 352.4 ± 229.5 (n = 10) | N/A |
| D (anti-BCMA × anti-CD3) | 16.49 ± 15.50 (n = 9) | −24.64 (*) | 733.8 ± 571.3 (n = 9) | 1.056 | 930.3 ± 887.6 (n = 9) | 2.433 |
| E (anti-IL-4Rα) | 34.90 ± 25.12 (n = 11) | −16.64 | 23.67 ± 16.67 (n = 11) | −18.05 | 24.4 ± 17.23 (n = 11) | −16.85 |
| F (anti-BCMA × anti-CD3 + anti-IL-4Rα) | Below LLOQ (n = 11) | −42.23 (**) | Below LLOQ (n = 10) | −38.10 () | Below LLOQ (n = 10) | −34.15 (*) |

Example 3: Effect of Combination Treatment with a BCMA×CD3 Bispecific Antibody and an Anti-IL-4Rα Antibody on IgE Bone Marrow Plasma Cells The mice described in Example 2 were also analyzed for IgE bone marrow plasma cells. Following the HDM exposure and antibody treatment protocol as described in Table 3 and FIG. 3, the mice were sacrificed, and femurs were collected from the mice. Bone marrow was extracted from the femurs by cutting both ends of each bone, placing each bone in an individual well of a 96-well PCR plate with holes cut in the bottom of each well, then placing the PCR plate on top of a 96-well 2 mL deep well collection plate and centrifuging the plate for 4 minutes at 500 g. The bone marrow was resuspended in 0.5 mL of RBC lysis buffer and incubated for 3 minutes at room temperature, followed by addition of 1-2 mL of PBS to deactivate the lysis buffer. Cells were centrifuged at 400 g for 4 minutes, the supernatant decanted and the pellet resuspended in 1 ml DPBS and filtered through Millipore plate filter (100 µm) into a 2 mL deep well plate. The cells were then centrifuged and resuspended in 200 µL of PBS. The bone marrow cells were then plated in 96-well plates and stained with a live/dead cell marker, followed by antibody staining with the antibodies B220, CD138, IgM, IgG1, IgA, IgD, IgE (extracellular block), and "Dump" (including TCRβ, CD200R3, Ly6G, CD49b, and CD11b).

After staining, the cells were washed twice with MACS buffer, fixed with BD Cytofix (cat #554655) diluted 1:4 in PBS for 15 minutes, then resuspended in MACS buffer and stored at 4° C. On the day of acquisition, the cells were washed, incubated in BD Perm/wash buffer (cat #554723) for 10 minutes and stained with the intracellular antibodies Light Chain κ, IgG1, and Intra IgE. The cells were then acquired in an LSRFortessa instrument and analyzed using FlowJo software. Mature IgE bone marrow plasma cells were identified as Live, Dump-B220-Light Chain κ+ IgE+. Percent reduction of plasma cells in individual antibody-administered mice was calculated with the following formula: 100−(100×percent plasma cells/mean percent plasma cells in the isotype group), where percent plasma cells are calculated relative to total live cells.

Results

Figure 5:
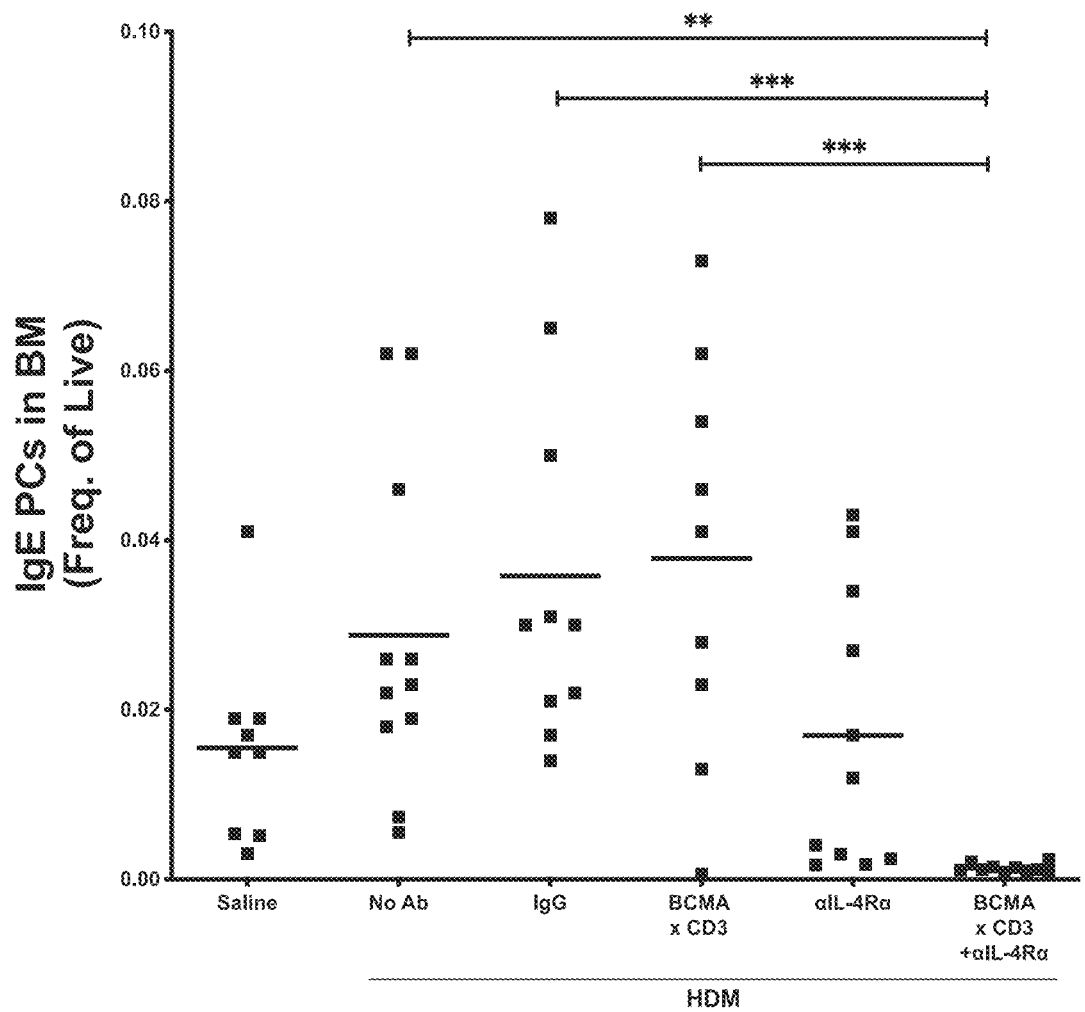
FIG. 5 shows the effect of anti-BCMA×anti-CD3 bispecific antibody and anti-IL-4Rα antibody, alone or in combination, on IgE bone marrow plasma cells 5 weeks after administration of anti-BCMA×anti-CD3 bispecific antibody. The asterisks (*) indicate degree of statistical significance relative to isotype controls (IgGs); *p≤0.05; p≤0.01; *p≤0.001; ****p≤1.0001.

In a chronic HDM model with continuous HDM exposure after antibody treatments, neither anti-IL4Rα or BCMA×CD3 administration alone had a significant impact on IgE bone marrow plasma cells at the time of harvest (5 weeks after BCMA×CD3 administration), although treatment with anti-Il-4Rα showed a trend towards reduced IgE bone marrow plasma cells (see FIG. 5 and Table 5). By contrast, the combination of continuous anti-IL-4Rα administration with transient anti-BCMA×anti-CD3 administration led to a significant reduction in IgE bone marrow plasma cells relative to both the untreated and the isotype control (see FIG. 5 and Table 5).

TABLE 5

IgE bone marrow plasma cells (BMPCs) following antibody treatment

| | Treatment | Plasma cells (percent of Live ± SD) | Mean Percent Decrease Relative to Average Plasma Cells in isotype control group |
|---|---|---|---|
| IgE BMPCs | Anti-BCMA × Anti CD3 | 0.0378 ± 0.023 | −5.72 (ns) |
| | Anti-IL4Rα | 0.017 ± 0.016 | 48.46 (ns) |
| | Anti-BCMA × Anti CD3 + Anti-IL4Rα | 0.0013 ± 0.0005 | 96.14 (***) |

Figure 6:
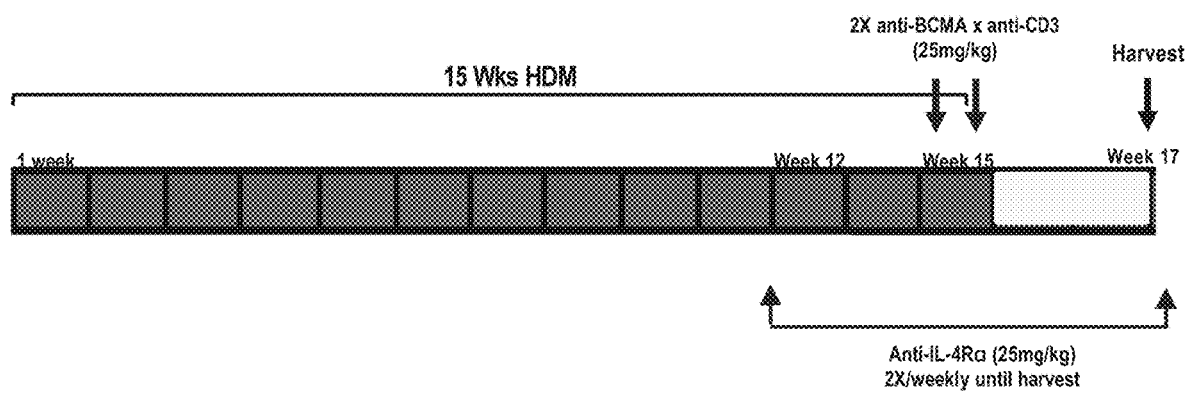
FIG. 6 is a diagrammatic representation of the HDM exposure and antibody treatment protocol in accordance with the study described in Example 4.

Example 4: Effect of Combination Treatment with a BCMA×CD3 Bispecific Antibody and an Anti-IL-4Rα Antibody on IgE Production and IgE-Producing Cells To determine the effect of combination treatment with anti-IL-4Rα and anti-BCMA×anti-CD3 on IgE production and IgE-producing cells in a relevant in vivo model, a HDM-driven lung inflammation study was conducted in mice that were homozygous for human BCMA and human CD3 in place of mouse BCMA and CD3 as described in Examples 1-2 above. Chronic lung inflammation and persistent IgE production was induced by exposing mice to 25 pg of HDM diluted in 20 µL of saline or to 20 µL of saline (control group) intranasally (i.n.) three times a week for 15 weeks. This model induces class switching of B cells into IgE producing plasma cells in secondary lymphoid organs and drives accumulation of IgE plasma cells in the bone marrow. At week 12 after the first HDM administration, a subset of mice started receiving subcutaneous injections of 25 mg/kg REGN1103 (anti-IL-4Rα) or 25 mg/kg REGN1094 (isotype control) until the end of the experiment. At week 15, two doses of REGN5459 (anti-BCMA×anti-CD3) or two doses of REGN4460 (isotype control) were administered subcutaneously and mice were rested for 2 weeks without further HDM administration. Details of HDM exposure and antibody treatment protocol are outlined in FIG. 6 and in Table 6 below.

TABLE 6

HDM exposure and antibody treatment protocol for mice to address the effect of anti-IL-4Rαand anti-BMCA × anti-CD3 antibody treatments on bone marrow plasma cell populations in a chronic (15 weeks) HDM model

| Group | BCMA × CD3 humanized mice (#) | Intranasal (i.n.) (15 weeks) | Antibody (2× weekly after week 12) | Antibody (2 doses at week 15) |
|---|---|---|---|---|
| A | 9 | Saline | None | None |
| B | 11 | HDM (12 weeks) | None | None |
| C | 13 | HDM | None | None |
| D | 10 | HDM | REGN1094 (Isotype control) | REGN4460 (Isotype control) |
| E | 9 | HDM | REGN1094 (Isotype control) | REGN5459 (anti-BCMA × anti-CD3) |
| F | 10 | HDM | REGN1103 (anti-IL-4Rα) | REGN4460 (Isotype control) |
| G | 10 | HDM | REGN1103 (anti-IL-4Rα) | REGN5459 (anti-BCMA × anti-CD3) |

Following the HDM exposure and antibody treatment protocol, the mice were sacrificed, and blood, spleen, and bones were taken. The blood was collected from all groups of mice by cardiac puncture and transferred into microtainer tubes (BD, Catalog #365967) for serum isolation. The HDM-specific IgE concentration in serum was determined using a Mouse Serum Anti-HDM IgE Antibody Assay kit (Chondrex catalog #3037) following manufacturer's instructions. Briefly, 100 µL of serum samples diluted at a concentration of 1:10 or 1:60, and HDM-IgE standard diluted at a starting concentration of 50 ng/mL with further 2-fold serial dilution was added to pre-coated plates provided with the kit and incubated at 4° C. overnight. Plates were then washed 3× in wash buffer and incubated in 100 µL of biotinylated HDM, provided with the kit. Plates were then washed 4× in wash buffer and incubated in 100 μL streptavidin peroxidase (provided with the kit) for 30 min at RT. Plates were washed 7× and 100 μL of TMB Substrate Solution (provided with the kit) was added to each sample and plates were incubated in the dark for 25 min followed by addition of 50 μL Stop Solution (2N Sulfuric Acid, provided with the kit). Absorbance was measured at 450 nm and HDM-IgE concentrations were calculated from a standard curve. Serum IgE values are shown as ng/mL. Statistical significance was determined by Kruskal-Wallis test with Dunn's post-hoc multi-comparison test in GraphPad Prism.

Spleens and femurs were also collected from the mice. Spleens were mashed on a 74-micron cell strainer in 2 ml RPMI media using the back end of a 3 mL syringe, and the single cell suspensions were transferred to a 96-well plate. Bone marrow was extracted from the femurs by cutting both ends of each bone, placing each bone in an individual well of a 96-well PCR plate with holes cut in the bottom of each well, then placing the PCR plate on top of a 96-well deep 2 mL deep well collection plate and centrifuging the plate for 4 minutes at 500 g. Spleen samples were resuspended in 1 mL and bone marrow in 0.5 mL of RBC lysis buffer and incubated for 3 minutes at room temperature, followed by addition of 1-2 mL of PBS to deactivate the lysis buffer. Cells were centrifuged at 400 g for 4 minutes, the supernatant decanted and the pellet resuspended in 1 mL DPBS and filtered through Millipore plate filter (100 μm) into a 2 mL deep well plate. The cells were then centrifuged and the splenic cells resuspended in 1 mL and the bone marrow in 200 μL of PBS. One tenth of the spleen cells and all of the bone marrow cells were then plated in 96-well plates and stained with a live/dead cell marker, followed by antibody staining with the antibodies B220, CD138, IgM, IgG1, IgA, IgD, IgE (extracellular block), and "Dump" (including TCRβ, CD200R3, Ly6G, CD49b, and CD11b). After staining, the cells were washed twice with MACS buffer, fixed with BD Cytofix (cat #554655) diluted 1:4 in PBS for 15 minutes, then resuspended in MACS buffer and stored at 4 degrees. On the day of acquisition, the cells were washed, incubated in BD Perm/wash buffer (cat #554723) for 10 minutes and stained with the intracellular antibodies Light Chain κ, IgG1, and Intra IgE. The cells were then acquired in an LSRFortessa instrument and analyzed using FlowJo software. Mature plasma cells were identified as Live, Dump-(dump includes TCRb, CD200R3, Ly6G, CD49b and CD11b) B220-Light Chain k+. Percent reduction of plasma cells in individual antibody-administered mice was calculated with the following formula: 100−(100×percent plasma cells/mean percent plasma cells in the isotype group), where percent plasma cells are calculated relative to total live cells. The results are shown in Table 7 below.

Results

Figure 7:
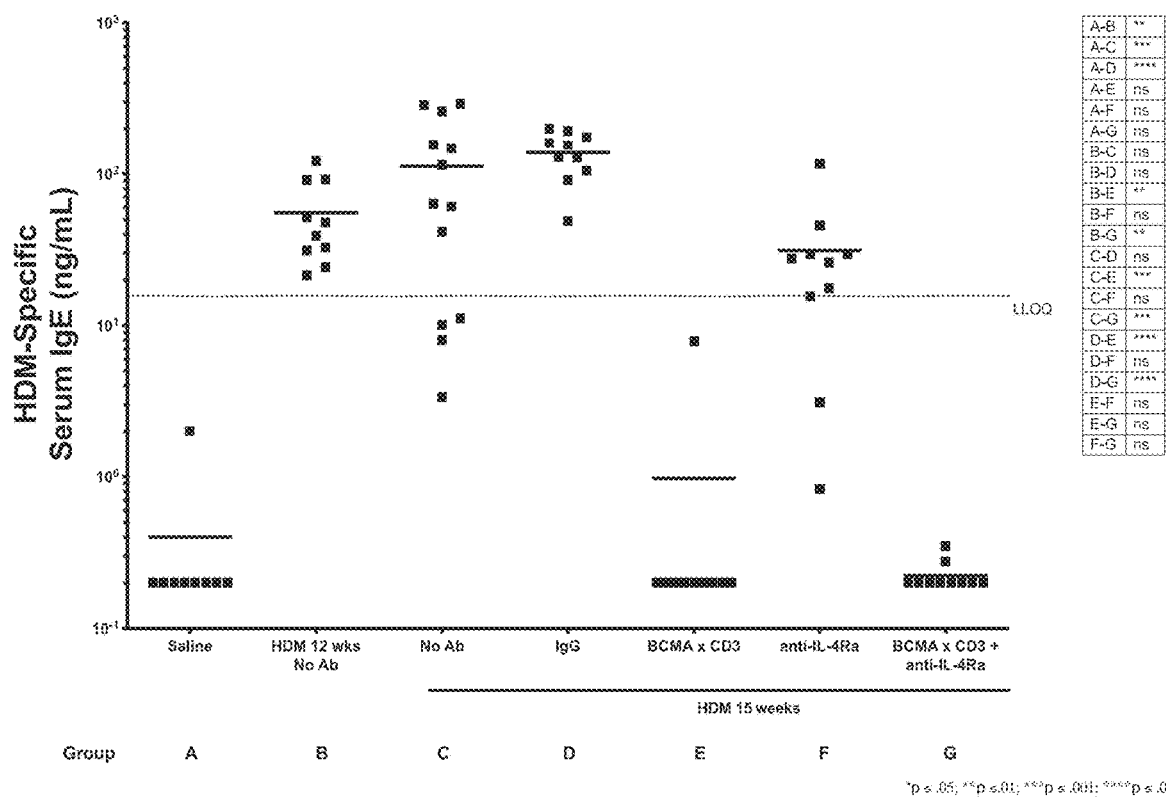
FIG. 7 shows the effect of anti-BCMA×anti-CD3 bispecific antibody and anti-IL-4Rα antibody, alone or in combination, on serum HDM-specific IgE levels. The treatment groups are described in Example 4 and Table 7 and are: Group A (saline), Group B (HDM for 12 weeks, no antibody), Group C (HDM for 15 weeks, no antibody), Group D (HDM for 15 weeks, isotype control antibodies), Group E (HDM for 15 weeks, anti-BCMA×anti-CD3 bispecific antibody), Group F (HDM for 15 weeks, anti-IL-4Rα antibody), and Group G (HDM for 15 weeks, anti-IL-4Rα antibody and anti-BCMA×anti-CD3 bispecific antibody). Statistical significance is compared between the treatment groups as shown in the inset. ns=not statistically significant; *p≤0.05; p≤0.01; *p≤0.001; ****p≤1.0001. LLOQ=lower limit of quantification.

In a chronic HDM model, anti-IL4Rα treatment (Group F) showed a trend towards reduced serum HDM-specific IgE levels with most samples having detectable levels of HDM-specific IgE (see, Table 7 and FIG. 7). Both the anti-BCMA×anti-CD3 treatment alone (Group E) and the combination of anti-IL-4Rα with anti-BCMA×anti-CD3 treatment (Group G) eliminated serum HDM-specific IgE, with all mice showing levels below the lower limit of quantification. These data demonstrate that anti-BCMA×anti-CD3 treatment is sufficient to significantly reduce serum HDM-specific IgE 2 weeks after administration.

Figure 8A:
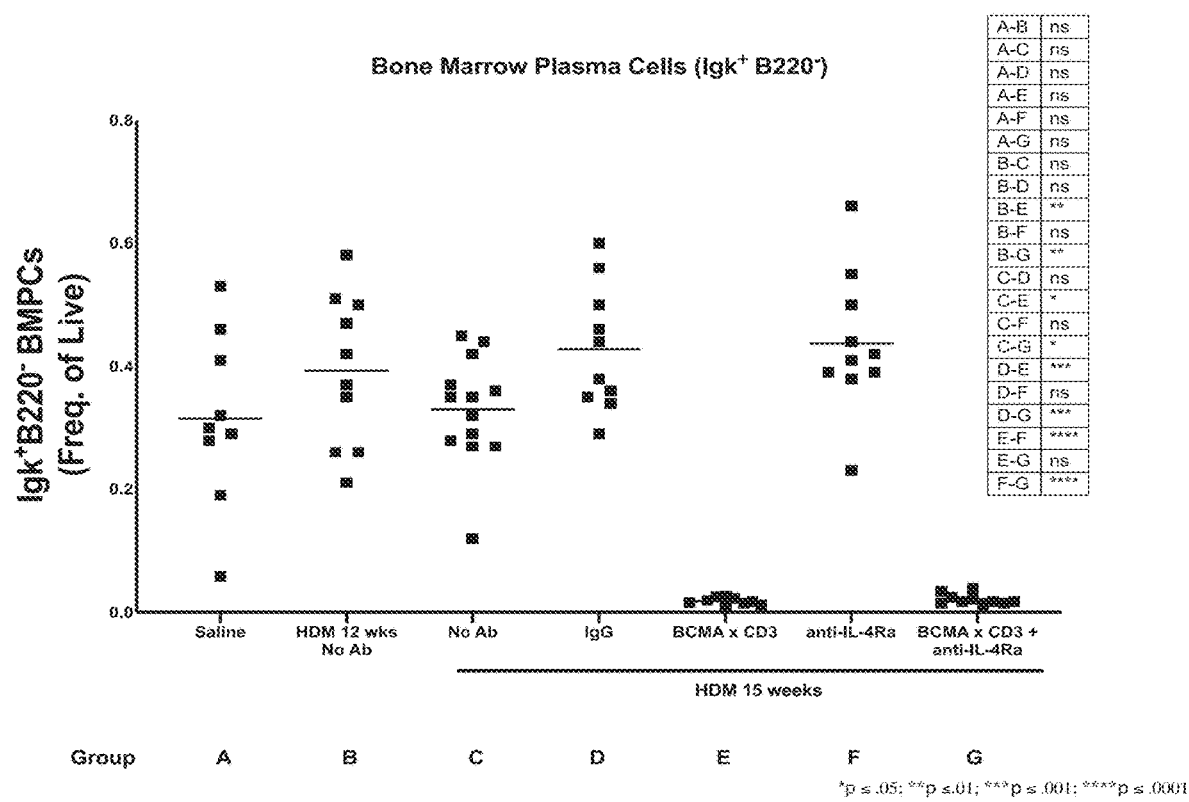
FIGS. 8A-8D show the effect of anti-BCMA×anti-CD3 bispecific antibody, alone or in combination with anti-IL-4Rα antibody, on total bone marrow plasma cells (FIG. 8A), IgE bone marrow plasma cells (FIG. 8B), total splenic plasma cells (FIG. 8C), and IgE splenic plasma cells (FIG. 8D). The treatment groups are described in Example 4 and Table 7 and are: Group A (saline), Group B (HDM for 12 weeks, no antibody), Group C (HDM for 15 weeks, no antibody), Group D (HDM for 15 weeks, isotype control antibodies), Group E (HDM for 15 weeks, anti-BCMA× anti-CD3 bispecific antibody), Group F (HDM for 15 weeks, anti-IL-4Rα antibody), and Group G (HDM for 15 weeks, anti-IL-4Rα antibody and anti-BCMA×anti-CD3 bispecific antibody). Statistical significance is compared between the treatment groups as shown in the inset. ns=not statistically significant; *p≤0.05; p≤0.01; *p≤0.001; ****p≤1.0001.
Figure 8B:
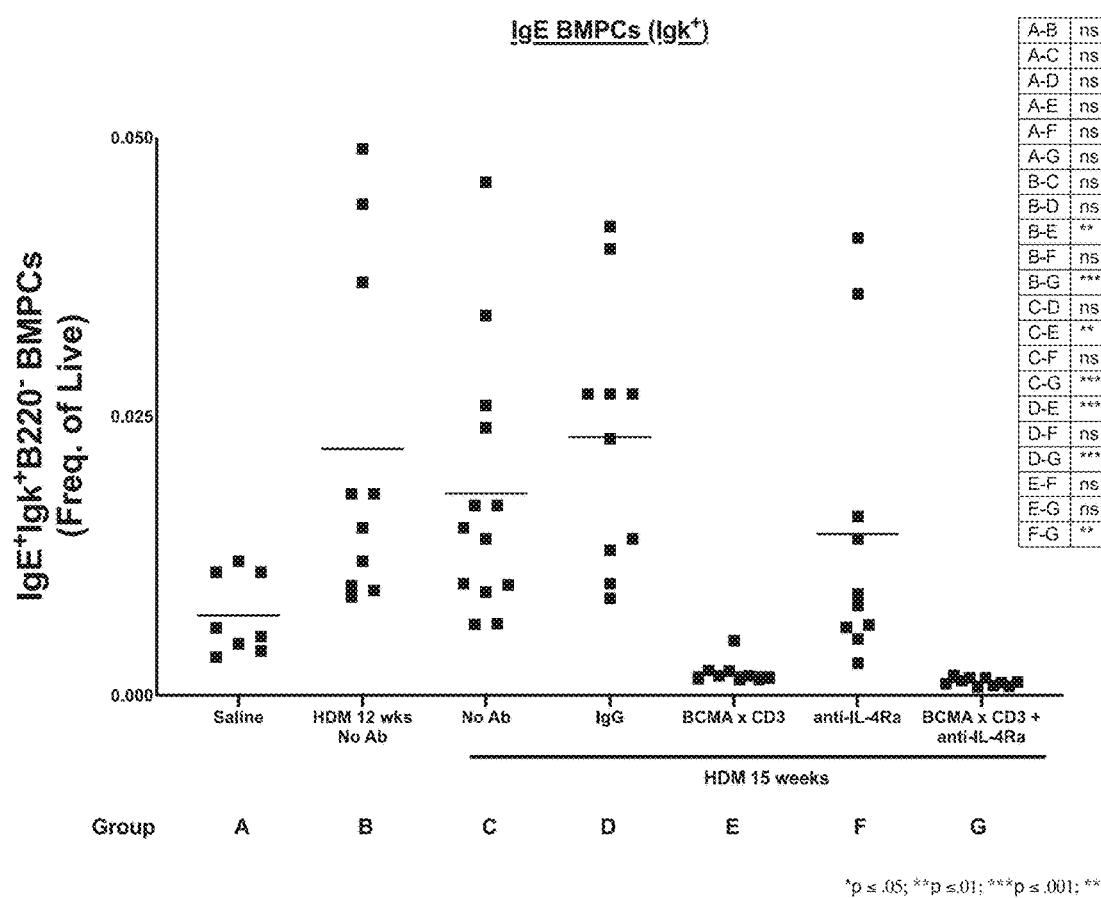
Figure 8C:
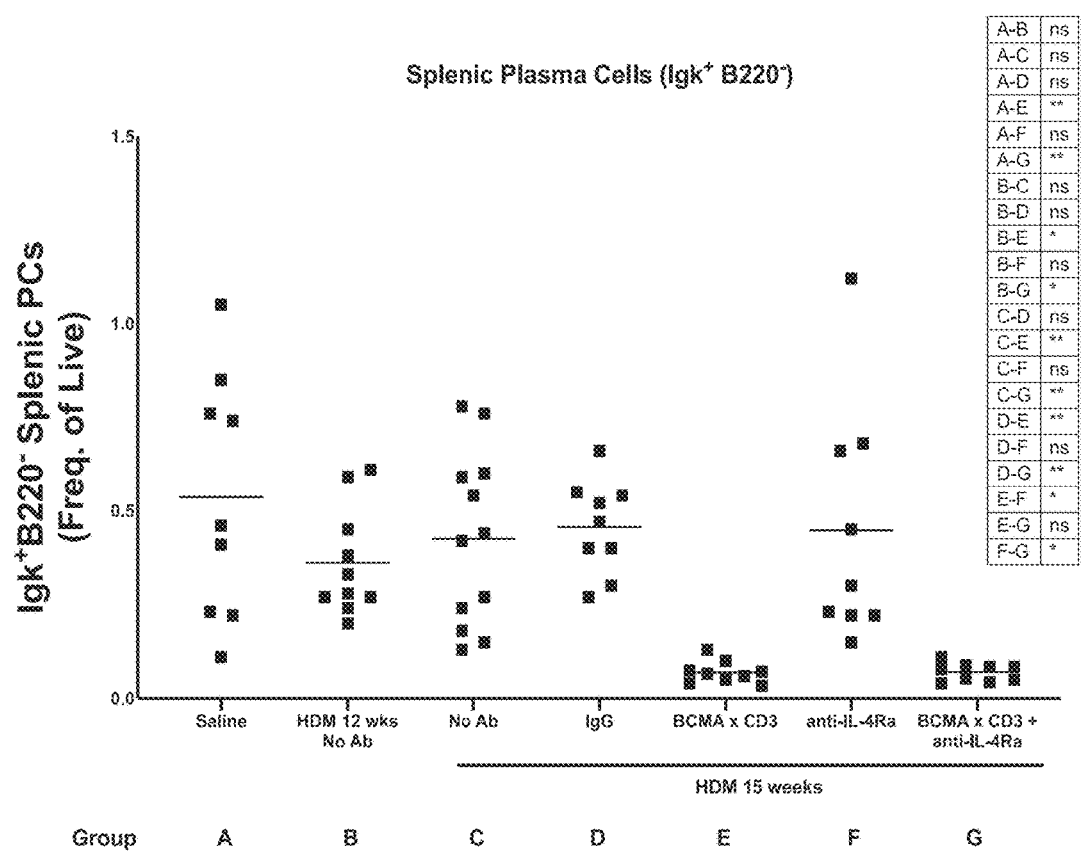
Figure 8D:
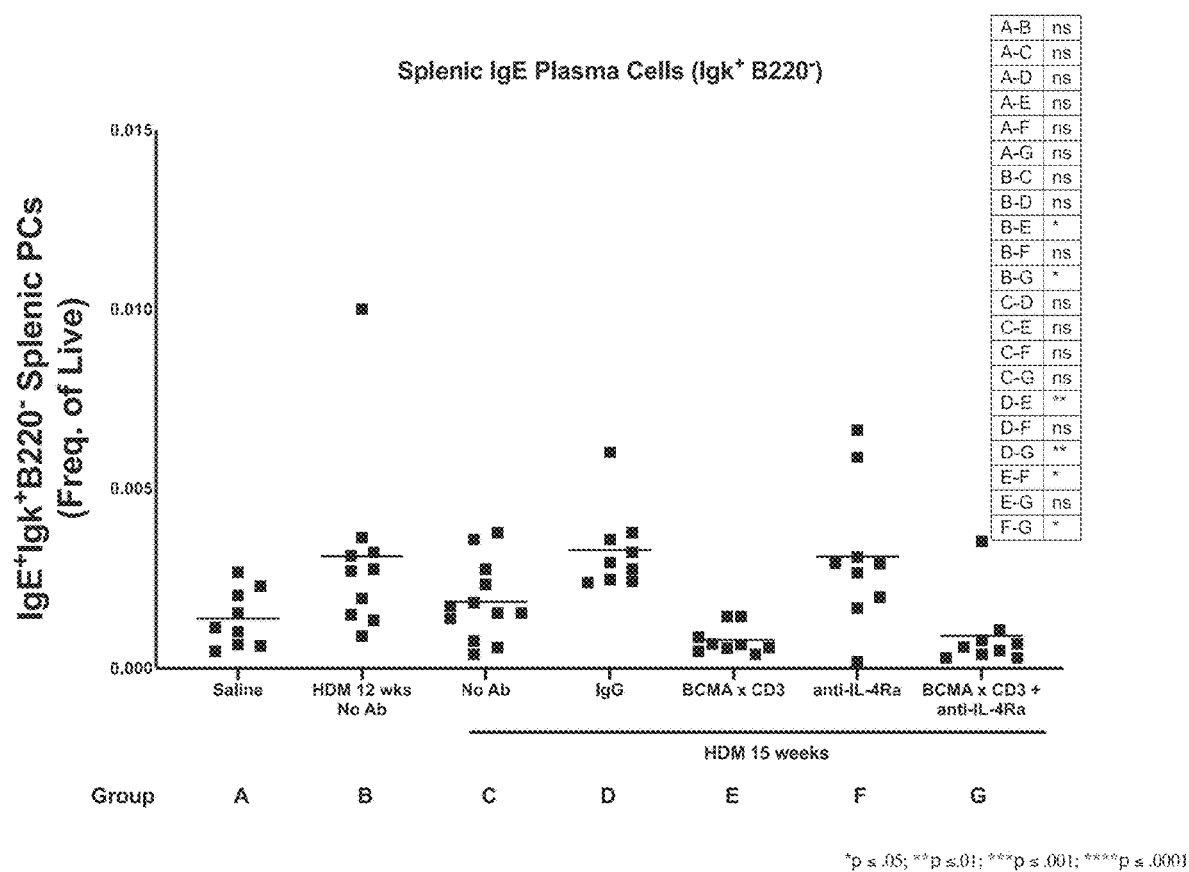

In the same experiment, anti-IL4Rα treatment did not impact total bone marrow plasma cells (FIG. 8A) and showed a trend towards reduced IgE bone marrow plasma cells (FIG. 8B). Anti-BCMA×anti-CD3 treatment alone led to a significant reduction in both total and IgE bone marrow plasma cells relative to both the untreated and the isotype control treated groups at the time of harvest (two weeks after REGN5459 administration) (FIG. 8A-8B). The combination of anti-IL-4Rα with anti-BCMA×anti-CD3 treatment also significantly reduced total and IgE-specific bone marrow plasma cells to a similar extent as the anti-BCMA×anti-CD3 alone, demonstrating that the latter treatment is sufficient to deplete bone marrow plasma cells. Similar results were also observed in the spleen; anti-IL4Rα treatment showed no impact on total or IgE splenic plasma cells (FIG. 8C-8D). Anti-BCMA×anti-CD3 treatment alone led to a significant reduction in total splenic plasma cells relative to both the untreated and the isotype control treated groups at the time of harvest (two weeks after REGN5459 administration) (FIG. 8C-8D). The combination of anti-IL-4Rα with anti-BCMA×anti-CD3 treatment also significantly reduced total splenic plasma cells to a similar extent as the anti-BCMA×anti-CD3 alone, demonstrating that the latter treatment is sufficient to deplete splenic plasma cells. IgE plasma cells were reduced both with anti-BCMA×anti-CD3 treatment alone as well as with the combination of anti-IL-4Rα and anti-BCMA×anti-CD3. However, the reduction in IgE splenic plasma cells only achieved statistical significance when compared to the group that received HDM for 12 weeks in the absence of antibody treatment or to the isotype control group, but not when compared to the group that received HDM for 15 weeks and no antibody treatment.

TABLE 7

Effect of anti-BCMA × anti-CD3 bispecific antibody, alone or in combination with anti-IL-4Rα antibody on serum HDM-specific IgE levels

| Group | A (Saline) | B (HDM 12 weeks) No Ab | C (No Ab) | D (IgG) | E (BCMA × CD3) | F (Anti-IL-4Rα) | G (BCMA × CD3 + anti-IL-4Rα) |
|---|---|---|---|---|---|---|---|
| Mean ± SD serum IgE (ng/mL) | 0.223 ± 0.669 | 55.37 ± 34.3 | 112.28 ± 108.88 | 139.13 ± 48.02 | 0.79 ± 2.51 | 31.25 ± 32.73 | 0.06 ± 0.13 |
| Mean rank difference compared to Isotype control | −47.02 (**) | −13.5 (ns) | −9.185 (ns) | N/A | −46.9 () | −21.4 (ns) | −46.1 (**) |

TABLE 8

Effect of anti-BMCA × anti-CD3 bispecific antibody, alone or in combination with anti-IL-4Rα antibody, on total and IgE bone marrow and splenic plasma cells

| | Treatment | Plasma cells (percent of Live ± SD) | Mean Percent Decrease Relative to Average Plasma Cells in isotype control group |
|---|---|---|---|
| Total BMPCs | Anti-BCMA × Anti CD3 | 0.018 ± 0.006 | 95.76 (***) |
| | Anti-IL4Ra | 0.437 ± 0.115 | −2.10 (ns) |
| | Anti-BCMA × Anti CD3 + Anti-IL4Ra | 0.021 ± 0.009 | 94.83 (***) |
| IgE BMPCs | Anti-BCMA × Anti CD3 | 0.002 ± 0.001 | 91.08 (***) |
| | Anti-IL4Ra | 0.014 ± 0.013 | 37.62 (ns) |
| | Anti-BCMA × Anti CD3 + Anti-IL4Ra | 0.001 ± 0.0003 | 94.65 (****) |
| Total Splenic PCs | Anti-BCMA × Anti CD3 | 0.07 ± 0.03 | 84.67 (**) |
| | Anti-IL4Ra | 0.448 ± 0.319 | 11.75 (ns) |
| | Anti-BCMA × Anti CD3 + Anti-IL4Ra | 0.07 ± 0.024 | 86.64 (**) |
| IgE Splenic PCs | Anti-BCMA × Anti CD3 | 0.00079 ± 0.0004 | 75.98 (**) |
| | Anti-IL4Ra | 0.0031 ± 0.002 | 14.97 (ns) |
| | Anti-BCMA × Anti CD3 + Anti-IL4Ra | 0.0009 ± 0.001 | 73.81 (**) |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of reducing or eliminating allergen-specific serum IgE in a subject, comprising: (a) selecting a subject with an allergic disease or disorder, a mast cell activation disorder or mastocytosis; and (b) administering to the subject in need thereof a therapeutically effective amount of an IL-4/IL-13 pathway inhibitor and a plasma cell ablating agent, wherein the plasma cell ablating agent is an anti-BCMA/anti-CD3 bispecific antibody or antigen-binding fragment thereof comprising (i) a first antigen-binding domain that specifically binds to BCMA; and (ii) a second antigen-binding domain that specifically binds CD3.

2. The method of claim 1, wherein the allergic disease or disorder is selected from the group consisting of allergic asthma, hay fever, chronic urticaria, food allergy, pollen allergy, and allergy due to an environmental (non-food) allergen.

3. The method of claim 1, wherein the subject is at a risk of anaphylaxis due to an allergen.

4. The method of claim 1, wherein the subject has a seasonal allergy.

5. The method of claim 1, wherein the subject has a severe allergy.

6. The method of claim 1, wherein the subject has an allergy due to one or more allergens selected from the group consisting of milk, a dairy product, egg, celery, sesame, wheat, meat, soy, fish, a fruit, shellfish, a sugar, peanut, a legume, a tree nut, dust, dust mite, pollen, insect venom, mold, animal fur, animal dander, wool, latex, a metal, a household cleaner, a detergent, medication, cosmetics, perfumes, a drug, therapeutic monoclonal antibodies, ragweed, grass and birch.

7. The method of claim 1, wherein the allergen is contained in or derived from a food item selected from the group consisting of milk, a dairy product, egg, celery, sesame, wheat, meat, fruit, soy, fish, shellfish, a sugar, peanut, a legume, and a tree nut.

8. The method of claim 1, wherein the allergen is a non-food allergen selected from the group consisting of dust, dust mite, pollen, insect venom, mold, animal fur, animal dander, wool, latex, a metal, a household cleaner, a detergent, medication, cosmetics, perfumes, a drug, therapeutic monoclonal antibodies, ragweed, grass and birch.

9. The method of claim 1, wherein the IL-4/IL-13 pathway inhibitor is selected from the group consisting of an anti-IL-4 antibody, an anti-IL-13 antibody, an anti-IL-4/IL-13 bispecific antibody, an IL-4 receptor (IL-4R) inhibitor, an IL-4 trap, an IL-13 trap, and an anti-IL-4R antibody.

10. The method of claim 1, wherein the IL-4/IL-13 pathway inhibitor is an anti-IL-4 antibody.

11. The method of claim 1, wherein the IL-4/IL-13 pathway inhibitor is an anti-IL-13 antibody.

12. The method of claim 1, wherein the IL-4/IL-13 pathway inhibitor is an anti-IL-4/IL-13 bispecific antibody.

13. The method of claim 1, wherein the IL-4/IL-13 pathway inhibitor is an IL-4R inhibitor.

14. The method of claim 1, wherein the IL-4/IL-13 pathway inhibitor is an anti-IL-4R antibody.

15. The method of claim 14, wherein the anti-IL-4R antibody comprises three heavy chain complementarity determining regions (CDRs) (HCDR1, HCDR2 and HCDR3) and three light chain CDRs (LCDR1, LCDR2 and LCDR3), wherein HCDR1 has the amino acid sequence of SEQ ID NO: 3, HCDR2 has the amino acid sequence of SEQ ID NO: 4, HCDR3 has the amino acid sequence of SEQ ID NO: 5, LCDR1 has the amino acid sequence of SEQ ID NO: 6, LCDR2 has the amino acid sequence of SEQ ID NO: 7, and LCDR3 has the amino acid sequence of SEQ ID NO: 8.

16. The method of claim 15, wherein the anti-IL-4R antibody comprises a heavy chain variable region (HCVR) comprising the amino acid sequence of SEQ ID NO: 1 and a light chain variable region (LCVR) comprising the amino acid sequence of SEQ ID NO: 2.

17. The method of claim 14, wherein the anti-IL-4R antibody comprises a heavy chain and a light chain, wherein the heavy chain has the amino acid sequence of SEQ ID NO: 9.

18. The method of claim 14, wherein the anti-IL-4R antibody comprises a heavy chain and a light chain, wherein the light chain has the amino acid sequence of SEQ ID NO: 10.

19. The method of claim 14, wherein the anti-IL-4R antibody comprises a heavy chain and a light chain, wherein the heavy chain has the amino acid sequence of SEQ ID NO: 9 and the light chain has the amino acid sequence of SEQ ID NO: 10.

20. The method of claim 1, wherein the IL-4/IL-13 pathway inhibitor is dupilumab or a bioequivalent thereof.

21. The method of claim 1, wherein the IL-4/IL-13 pathway inhibitor is selected from the group consisting of dupilumab, pascolizumab, AMG317, MEDI2045, MEDI9314, tralokinumab, lebrikzimab, anrukinzumab, dectrekumab, GSK679586, MEDI7836, romilkimab, an IL-4 trap, an IL-13 trap, AER-003, and pitrakinra.

22. The method of claim 1, wherein the first antigen-binding domain that specifically binds to BCMA comprises three heavy chain CDRs (HCDR1, HCDR2 and HCDR3) contained within a heavy chain variable region (HCVR) comprising the amino acid sequence of SEQ ID NO: 12, and three light chain CDRs (LCDR1, LCDR2 and LCDR3) contained within a light chain variable region (LCVR) comprising the amino acid sequence of SEQ ID NO: 20.

23. The method of claim 22, wherein HCDR1 has the amino acid sequence of SEQ ID NO: 14, HCDR2 has the amino acid sequence of SEQ ID NO: 16, HCDR3 has the amino acid sequence of SEQ ID NO: 18, LCDR1 has the amino acid sequence of SEQ ID NO: 22, LCDR2 has the amino acid sequence of SEQ ID NO: 24, and LCDR3 has the amino acid sequence of SEQ ID NO: 26.

24. The method of claim 1, wherein the second antigen-binding domain that specifically binds to CD3 comprises three heavy chain CDRs (HCDR1, HCDR2 and HCDR3) contained within a heavy chain variable region (HCVR) comprising the amino acid sequence selected from the group consisting of SEQ ID NOs: 28 and 36, and three light chain CDRs (LCDR1, LCDR2 and LCDR3) contained within a light chain variable region (LCVR) comprising the amino acid sequence of SEQ ID NO: 20.

25. The method of claim 24, wherein HCDR1 has the amino acid sequence of SEQ ID NO: 30 or 38, HCDR2 has the amino acid sequence of SEQ ID NO: 32 or 40, HCDR3 has the amino acid sequence of SEQ ID NO: 34 or 42, LCDR1 has the amino acid sequence of SEQ ID NO: 22, LCDR2 has the amino acid sequence of SEQ ID NO: 24, and LCDR3 has the amino acid sequence of SEQ ID NO: 26.

26. The method of claim 1, wherein the anti-BCMA/anti-CD3 bispecific antibody or antigen-binding fragment thereof comprises:
(a) a first antigen-binding domain that comprises HCDR1, HCDR2, and HCDR3 domains, respectively, comprising the amino acid sequences of SEQ ID NOs: 14, 16, and 18, and LCDR1, LCDR2, and LCDR3 domains, respectively, comprising the amino acid sequences of SEQ ID NOs: 22, 24, and 26; and
(b) a second antigen-binding domain that comprises HCDR1, HCDR2, and HCDR3 domains, respectively, comprising the amino acid sequences of SEQ ID NOs: 30, 32, and 34, and LCDR1, LCDR2, and LCDR3 domains, respectively, comprising the amino acid sequences of SEQ ID NOs: 22, 24, and 26.

27. The method of claim 1, wherein the anti-BCMA/anti-CD3 bispecific antibody or antigen-binding fragment thereof comprises:
(a) a first antigen-binding domain that comprises HCDR1, HCDR2, and HCDR3 domains, respectively, comprising the amino acid sequences of SEQ ID NOs: 14, 16, and 18, and LCDR1, LCDR2, and LCDR3 domains, respectively, comprising the amino acid sequences of SEQ ID NOs: 22, 24, and 26; and
(b) a second antigen-binding domain that comprises HCDR1, HCDR2, and HCDR3 domains, respectively, comprising the amino acid sequences of SEQ ID NOs: 38, 40, and 42, and LCDR1, LCDR2, and LCDR3 domains, respectively, comprising the amino acid sequences of SEQ ID NOs: 22, 24, and 26.

28. The method of claim 1, wherein the IL-4/IL-13 pathway inhibitor is administered prior to the plasma cell ablating agent.

29. The method of claim 1, wherein the IL-4/IL-13 pathway inhibitor is administered after the plasma cell ablating agent.

30. The method of claim 1, wherein the IL-4/IL-13 pathway inhibitor and the plasma cell ablating agent are administered concurrently.

31. The method of claim 1, further comprising administering at least one additional therapeutic agent or therapy.

32. The method of claim 31, wherein the additional therapeutic agent is selected from the group consisting of an IgE antagonist, an anti-histamine, an anti-inflammatory agent, a corticosteroid, a leukotriene antagonist, a mast cell inhibitor, a bronchial dilator, a decongestant, epinephrine, an IL-1 antagonist, an IL-5 antagonist, an IL-31 antagonist, an IL-33 antagonist, an IL-25 antagonist, interferon γ, a TNF antagonist, and a TSLP antagonist.

33. The method of claim 1, wherein:
the IL-4/IL-13 pathway inhibitor is an anti-IL-4R antibody, wherein the anti-IL-4R antibody comprises an HCVR comprising the amino acid sequence of SEQ ID NO:1 and an LCVR comprising the amino acid sequence of SEQ ID NO:2; and
the anti-BCMA/anti-CD3 bispecific antibody or antigen-binding fragment thereof comprises (a) a first antigen-binding domain that comprises an HCVR comprising the amino acid sequence of SEQ ID NO:12 and an LCVR comprising the amino acid sequence of SEQ ID NO:20; and a second antigen-binding domain that comprises an HCVR comprising the amino acid sequence of SEQ ID NO:36 and an LCVR comprising the amino acid sequence of SEQ ID NO:20.

34. A method of treating allergy or reducing the severity of an allergic reaction to an allergen, comprising: (a) selecting a subject with an allergic disease or disorder, a mast cell activation disorder, or mastocytosis; and (b) administering to the subject in need thereof a therapeutically effective amount of an IL-4/IL-13 pathway inhibitor and a plasma cell ablating agent, wherein the plasma cell ablating agent is an anti-BCMA/anti-CD3 bispecific antibody or antigen-binding fragment thereof comprising (i) a first antigen-binding domain that specifically binds to BCMA; and (ii) a second antigen-binding domain that specifically binds CD3.

35. The method of claim 34, wherein the allergic disease or disorder is selected from the group consisting of allergic asthma, hay fever, chronic urticaria, food allergy, pollen allergy, and allergy due to an environmental (non-food) allergen.

36. The method of claim 34, wherein the subject is at a risk of anaphylaxis due to an allergen.

37. The method of claim 34, wherein the subject has a seasonal allergy.

38. The method of claim 34, wherein the subject has a severe allergy.

39. The method of claim 34, wherein the subject has an allergy due to one or more allergens selected from the group consisting of milk, a dairy product, egg, celery, sesame, wheat, meat, soy, fish, a fruit, shellfish, a sugar, peanut, a legume, a tree nut, dust, dust mite, pollen, insect venom, mold, animal fur, animal dander, wool, latex, a metal, a household cleaner, a detergent, medication, cosmetics, perfumes, a drug, therapeutic monoclonal antibodies, ragweed, grass and birch.

40. The method of claim 34, wherein the allergen is contained in or derived from a food item selected from the group consisting of milk, a dairy product, egg, celery, sesame, wheat, meat, fruit, soy, fish, shellfish, a sugar, peanut, a legume, and a tree nut.

41. The method of claim 34, wherein the allergen is a non-food allergen selected from the group consisting of dust, dust mite, pollen, insect venom, mold, animal fur, animal dander, wool, latex, a metal, a household cleaner, a detergent, medication, cosmetics, perfumes, a drug, therapeutic monoclonal antibodies, ragweed, grass and birch.

42. The method of claim 34, wherein the IL-4/IL-13 pathway inhibitor is selected from the group consisting of an anti-IL-4 antibody, an anti-IL-13 antibody, an anti-IL-4/IL-13 bispecific antibody, an IL-4 receptor (IL-4R) inhibitor, an IL-4 trap, an IL-13 trap, and an anti-IL-4R antibody.

43. The method of claim 34, wherein the IL-4/IL-13 pathway inhibitor is an anti-IL-4 antibody.

44. The method of claim 34, wherein the IL-4/IL-13 pathway inhibitor is an anti-IL-13 antibody.

45. The method of claim 34, wherein the IL-4/IL-13 pathway inhibitor is an anti-IL-4/IL-13 bispecific antibody.

46. The method of claim 34, wherein the IL-4/IL-13 pathway inhibitor is an IL-4R inhibitor.

47. The method of claim 34, wherein the IL-4/IL-13 pathway inhibitor is an anti-IL-4R antibody.

48. The method of claim 47, wherein the anti-IL-4R antibody comprises three heavy chain complementarity determining regions (CDRs) (HCDR1, HCDR2 and HCDR3) and three light chain CDRs (LCDR1, LCDR2 and LCDR3), wherein HCDR1 has the amino acid sequence of SEQ ID NO: 3, HCDR2 has the amino acid sequence of SEQ ID NO: 4, HCDR3 has the amino acid sequence of SEQ ID NO: 5, LCDR1 has the amino acid sequence of SEQ ID NO: 6, LCDR2 has the amino acid sequence of SEQ ID NO: 7, and LCDR3 has the amino acid sequence of SEQ ID NO: 8.

49. The method of claim 48, wherein the anti-IL-4R antibody comprises a heavy chain variable region (HCVR) comprising the amino acid sequence of SEQ ID NO: 1 and a light chain variable region (LCVR) comprising the amino acid sequence of SEQ ID NO: 2.

50. The method of claim 47, wherein the anti-IL-4R antibody comprises a heavy chain and a light chain, wherein the heavy chain has the amino acid sequence of SEQ ID NO: 9.

51. The method of claim 47, wherein the anti-IL-4R antibody comprises a heavy chain and a light chain, wherein the light chain has the amino acid sequence of SEQ ID NO: 10.

52. The method of claim 47, wherein the anti-IL-4R antibody comprises a heavy chain and a light chain, wherein the heavy chain has the amino acid sequence of SEQ ID NO: 9 and the light chain has the amino acid sequence of SEQ ID NO: 10.

53. The method of claim 34, wherein the IL-4/IL-13 pathway inhibitor is dupilumab or a bioequivalent thereof.

54. The method of claim 34, wherein the IL-4/IL-13 pathway inhibitor is selected from the group consisting of dupilumab, pascolizumab, AMG317, MEDI2045, MEDI9314, tralokinumab, lebrikzimab, anrukinzumab, dectrekumab, GSK679586, MEDI7836, romilkimab, an IL-4 trap, an IL-13 trap, AER-003, and pitrakinra.

55. The method of claim 34, wherein the first antigen-binding domain that specifically binds to BCMA comprises three heavy chain CDRs (HCDR1, HCDR2 and HCDR3) contained within a heavy chain variable region (HCVR) comprising the amino acid sequence of SEQ ID NO: 12, and three light chain CDRs (LCDR1, LCDR2 and LCDR3) contained within a light chain variable region (LCVR) comprising the amino acid sequence of SEQ ID NO: 20.

56. The method of claim 55, wherein HCDR1 has the amino acid sequence of SEQ ID NO: 14, HCDR2 has the amino acid sequence of SEQ ID NO: 16, HCDR3 has the amino acid sequence of SEQ ID NO: 18, LCDR1 has the amino acid sequence of SEQ ID NO: 22, LCDR2 has the amino acid sequence of SEQ ID NO: 24, and LCDR3 has the amino acid sequence of SEQ ID NO: 26.

57. The method of claim 34, wherein the second antigen-binding domain that specifically binds to CD3 comprises three heavy chain CDRs (HCDR1, HCDR2 and HCDR3)

contained within a heavy chain variable region (HCVR) comprising the amino acid sequence selected from the group consisting of SEQ ID NOs: 28 and 36, and three light chain CDRs (LCDR1, LCDR2 and LCDR3) contained within a light chain variable region (LCVR) comprising the amino acid sequence of SEQ ID NO: 20.

58. The method of claim 57, wherein HCDR1 has the amino acid sequence of SEQ ID NO: 30 or 38, HCDR2 has the amino acid sequence of SEQ ID NO: 32 or 40, HCDR3 has the amino acid sequence of SEQ ID NO: 34 or 42, LCDR1 has the amino acid sequence of SEQ ID NO: 22, LCDR2 has the amino acid sequence of SEQ ID NO: 24, and LCDR3 has the amino acid sequence of SEQ ID NO: 26.

59. The method of claim 34, wherein the anti-BCMA/anti-CD3 bispecific antibody or antigen-binding fragment thereof comprises:
    (a) a first antigen-binding domain that comprises HCDR1, HCDR2, and HCDR3 domains, respectively, comprising the amino acid sequences of SEQ ID NOs: 14, 16, and 18, and LCDR1, LCDR2, and LCDR3 domains, respectively, comprising the amino acid sequences of SEQ ID NOs: 22, 24, and 26; and
    (b) a second antigen-binding domain that comprises HCDR1, HCDR2, and HCDR3 domains, respectively, comprising the amino acid sequences of SEQ ID NOs: 30, 32, and 34, and LCDR1, LCDR2, and LCDR3 domains, respectively, comprising the amino acid sequences of SEQ ID NOs: 22, 24, and 26.

60. The method of claim 34, wherein the anti-BCMA/anti-CD3 bispecific antibody or antigen-binding fragment thereof comprises:
    (a) a first antigen-binding domain that comprises HCDR1, HCDR2, and HCDR3 domains, respectively, comprising the amino acid sequences of SEQ ID NOs: 14, 16, and 18, and LCDR1, LCDR2, and LCDR3 domains, respectively, comprising the amino acid sequences of SEQ ID NOs: 22, 24, and 26; and
    (b) a second antigen-binding domain that comprises HCDR1, HCDR2, and HCDR3 domains, respectively, comprising the amino acid sequences of SEQ ID NOs: 38, 40, and 42, and LCDR1, LCDR2, and LCDR3 domains, respectively, comprising the amino acid sequences of SEQ ID NOs: 22, 24, and 26.

61. The method of claim 34, wherein the IL-4/IL-13 pathway inhibitor is administered prior to the plasma cell ablating agent.

62. The method of claim 34, wherein the IL-4/IL-13 pathway inhibitor is administered after the plasma cell ablating agent.

63. The method of claim 34, wherein the IL-4/IL-13 pathway inhibitor and the plasma cell ablating agent are administered concurrently.

64. The method of claim 34, further comprising administering at least one additional therapeutic agent or therapy.

65. The method of claim 64, wherein the additional therapeutic agent is selected from the group consisting of an IgE antagonist, an anti-histamine, an anti-inflammatory agent, a corticosteroid, a leukotriene antagonist, a mast cell inhibitor, a bronchial dilator, a decongestant, epinephrine, an IL-1 antagonist, an IL-5 antagonist, an IL-31 antagonist, an IL-33 antagonist, an IL-25 antagonist, interferon γ, a TNF antagonist, and a TSLP antagonist.

66. The method of claim 34, wherein:
    the IL-4/IL-13 pathway inhibitor is an anti-IL-4R antibody, wherein the anti-IL-4R antibody comprises an HCVR comprising the amino acid sequence of SEQ ID NO:1 and an LCVR comprising the amino acid sequence of SEQ ID NO:2; and
    the anti-BCMA/anti-CD3 bispecific antibody or antigen-binding fragment thereof comprises (a) a first antigen-binding domain that comprises an HCVR comprising the amino acid sequence of SEQ ID NO:12 and an LCVR comprising the amino acid sequence of SEQ ID NO:20; and a second antigen-binding domain that comprises an HCVR comprising the amino acid sequence of SEQ ID NO:36 and an LCVR comprising the amino acid sequence of SEQ ID NO:20.

67. A method for treating allergy or reducing the severity of an allergic reaction to an allergen, comprising: (a) selecting a subject with an allergic disease or disorder, a mast cell activation disorder, or mastocytosis, wherein the subject is on a background therapy regimen comprising one or more doses of an IL-4/IL-13 pathway inhibitor; and (b) administering to the subject at least one dose of a plasma cell ablating agent, wherein the plasma cell ablating agent is an anti-BCMA/anti-CD3 bispecific antibody or antigen-binding fragment thereof comprising (i) a first antigen-binding domain that specifically binds to BCMA; and (ii) a second antigen-binding domain that specifically binds CD3.

68. The method of claim 67, wherein the allergic disease or disorder is selected from the group consisting of allergic asthma, hay fever, chronic urticaria, food allergy, pollen allergy, and allergy due to an environmental (non-food) allergen.

69. The method of claim 67, wherein the subject is at a risk of anaphylaxis due to an allergen.

70. The method of claim 67, wherein the subject has a seasonal allergy.

71. The method of claim 67, wherein the subject has a severe allergy.

72. The method of claim 67, wherein the subject has an allergy due to one or more allergens selected from the group consisting of milk, a dairy product, egg, celery, sesame, wheat, meat, soy, fish, a fruit, shellfish, a sugar, peanut, a legume, a tree nut, dust, dust mite, pollen, insect venom, mold, animal fur, animal dander, wool, latex, a metal, a household cleaner, a detergent, medication, cosmetics, perfumes, a drug, therapeutic monoclonal antibodies, ragweed, grass and birch.

73. The method of claim 67, wherein the allergen is contained in or derived from a food item selected from the group consisting of milk, a dairy product, egg, celery, sesame, wheat, meat, fruit, soy, fish, shellfish, a sugar, peanut, a legume, and a tree nut.

74. The method of claim 67, wherein the allergen is a non-food allergen selected from the group consisting of dust, dust mite, pollen, insect venom, mold, animal fur, animal dander, wool, latex, a metal, a household cleaner, a detergent, medication, cosmetics, perfumes, a drug, therapeutic monoclonal antibodies, ragweed, grass and birch.

75. The method of claim 67, wherein the IL-4/IL-13 pathway inhibitor is selected from the group consisting of an anti-IL-4 antibody, an anti-IL-13 antibody, an anti-IL-4/IL-13 bispecific antibody, an IL-4 receptor (IL-4R) inhibitor, an IL-4 trap, an IL-13 trap, and an anti-IL-4R antibody.

76. The method of claim 67, wherein the IL-4/IL-13 pathway inhibitor is an anti-IL-4 antibody.

77. The method of claim 67, wherein the IL-4/IL-13 pathway inhibitor is an anti-IL-13 antibody.

78. The method of claim 67, wherein the IL-4/IL-13 pathway inhibitor is an anti-IL-4/IL-13 bispecific antibody.

79. The method of claim 67, wherein the IL-4/IL-13 pathway inhibitor is an IL-4R inhibitor.

80. The method of claim 67, wherein the IL-4/IL-13 pathway inhibitor is an anti-IL-4R antibody.

81. The method of claim 80, wherein the anti-IL-4R antibody comprises three heavy chain complementarity determining regions (CDRs) (HCDR1, HCDR2 and HCDR3) and three light chain CDRs (LCDR1, LCDR2 and LCDR3), wherein HCDR1 has the amino acid sequence of SEQ ID NO: 3, HCDR2 has the amino acid sequence of SEQ ID NO: 4, HCDR3 has the amino acid sequence of SEQ ID NO: 5, LCDR1 has the amino acid sequence of SEQ ID NO: 6, LCDR2 has the amino acid sequence of SEQ ID NO: 7, and LCDR3 has the amino acid sequence of SEQ ID NO: 8.

82. The method of claim 81, wherein the anti-IL-4R antibody comprises a heavy chain variable region (HCVR) comprising the amino acid sequence of SEQ ID NO: 1 and a light chain variable region (LCVR) comprising the amino acid sequence of SEQ ID NO: 2.

83. The method of claim 80, wherein the anti-IL-4R antibody comprises a heavy chain and a light chain, wherein the heavy chain has the amino acid sequence of SEQ ID NO: 9.

84. The method of claim 80, wherein the anti-IL-4R antibody comprises a heavy chain and a light chain, wherein the light chain has the amino acid sequence of SEQ ID NO: 10.

85. The method of claim 80, wherein the anti-IL-4R antibody comprises a heavy chain and a light chain, wherein the heavy chain has the amino acid sequence of SEQ ID NO: 9 and the light chain has the amino acid sequence of SEQ ID NO: 10.

86. The method of claim 67, wherein the IL-4/IL-13 pathway inhibitor is dupilumab or a bioequivalent thereof.

87. The method of claim 67, wherein the IL-4/IL-13 pathway inhibitor is selected from the group consisting of dupilumab, pascolizumab, AMG317, MEDI2045, MEDI9314, tralokinumab, lebrikzimab, anrukinzumab, dectrekumab, GSK679586, MEDI7836, romilkimab, an IL-4 trap, an IL-13 trap, AER-003, and pitrakinra.

88. The method of claim 67, wherein the first antigen-binding domain that specifically binds to BCMA comprises three heavy chain CDRs (HCDR1, HCDR2 and HCDR3) contained within a heavy chain variable region (HCVR) comprising the amino acid sequence of SEQ ID NO: 12, and three light chain CDRs (LCDR1, LCDR2 and LCDR3) contained within a light chain variable region (LCVR) comprising the amino acid sequence of SEQ ID NO: 20.

89. The method of claim 88, wherein HCDR1 has the amino acid sequence of SEQ ID NO: 14, HCDR2 has the amino acid sequence of SEQ ID NO: 16, HCDR3 has the amino acid sequence of SEQ ID NO: 18, LCDR1 has the amino acid sequence of SEQ ID NO: 22, LCDR2 has the amino acid sequence of SEQ ID NO: 24, and LCDR3 has the amino acid sequence of SEQ ID NO: 26.

90. The method of claim 67, wherein the second antigen-binding domain that specifically binds to CD3 comprises three heavy chain CDRs (HCDR1, HCDR2 and HCDR3) contained within a heavy chain variable region (HCVR) comprising the amino acid sequence selected from the group consisting of SEQ ID NOs: 28 and 36, and three light chain CDRs (LCDR1, LCDR2 and LCDR3) contained within a light chain variable region (LCVR) comprising the amino acid sequence of SEQ ID NO: 20.

91. The method of claim 90, wherein HCDR1 has the amino acid sequence of SEQ ID NO: 30 or 38, HCDR2 has the amino acid sequence of SEQ ID NO: 32 or 40, HCDR3 has the amino acid sequence of SEQ ID NO: 34 or 42, LCDR1 has the amino acid sequence of SEQ ID NO: 22, LCDR2 has the amino acid sequence of SEQ ID NO: 24, and LCDR3 has the amino acid sequence of SEQ ID NO: 26.

92. The method of claim 67, wherein the anti-BCMA/anti-CD3 bispecific antibody or antigen-binding fragment thereof comprises:
(a) a first antigen-binding domain that comprises HCDR1, HCDR2, and HCDR3 domains, respectively, comprising the amino acid sequences of SEQ ID NOs: 14, 16, and 18, and LCDR1, LCDR2, and LCDR3 domains, respectively, comprising the amino acid sequences of SEQ ID NOs: 22, 24, and 26; and
(b) a second antigen-binding domain that comprises HCDR1, HCDR2, and HCDR3 domains, respectively, comprising the amino acid sequences of SEQ ID NOs: 30, 32, and 34, and LCDR1, LCDR2, and LCDR3 domains, respectively, comprising the amino acid sequences of SEQ ID NOs: 22, 24, and 26.

93. The method of claim 67, wherein the anti-BCMA/anti-CD3 bispecific antibody or antigen-binding fragment thereof comprises:
(a) a first antigen-binding domain that comprises HCDR1, HCDR2, and HCDR3 domains, respectively, comprising the amino acid sequences of SEQ ID NOs: 14, 16, and 18, and LCDR1, LCDR2, and LCDR3 domains, respectively, comprising the amino acid sequences of SEQ ID NOs: 22, 24, and 26; and
(b) a second antigen-binding domain that comprises HCDR1, HCDR2, and HCDR3 domains, respectively, comprising the amino acid sequences of SEQ ID NOs: 38, 40, and 42, and LCDR1, LCDR2, and LCDR3 domains, respectively, comprising the amino acid sequences of SEQ ID NOs: 22, 24, and 26.

94. The method of claim 67, wherein the IL-4/IL-13 pathway inhibitor is administered prior to the plasma cell ablating agent.

95. The method of claim 67, wherein the IL-4/IL-13 pathway inhibitor is administered after the plasma cell ablating agent.

96. The method of claim 67, wherein the IL-4/IL-13 pathway inhibitor and the plasma cell ablating agent are administered concurrently.

97. The method of claim 67, further comprising administering at least one additional therapeutic agent or therapy.

98. The method of claim 97, wherein the additional therapeutic agent is selected from the group consisting of an IgE antagonist, an anti-histamine, an anti-inflammatory agent, a corticosteroid, a leukotriene antagonist, a mast cell inhibitor, a bronchial dilator, a decongestant, epinephrine, an IL-1 antagonist, an IL-5 antagonist, an IL-31 antagonist, an IL-33 antagonist, an IL-25 antagonist, interferon γ, a TNF antagonist, and a TSLP antagonist.

99. The method of claim 67, wherein:
the IL-4/IL-13 pathway inhibitor is an anti-IL-4R antibody, wherein the anti-IL-4R antibody comprises an HCVR comprising the amino acid sequence of SEQ ID NO:1 and an LCVR comprising the amino acid sequence of SEQ ID NO:2; and
the anti-BCMA/anti-CD3 bispecific antibody or antigen-binding fragment thereof comprises (a) a first antigen-binding domain that comprises an HCVR comprising the amino acid sequence of SEQ ID NO:12 and an LCVR comprising the amino acid sequence of SEQ ID NO:20; and a second antigen-binding domain that comprises an HCVR comprising the amino acid sequence of SEQ ID NO:36 and an LCVR comprising the amino acid sequence of SEQ ID NO:20.

\* \* \* \* \*

UNITED STATES PATENT AND TRADEMARK OFFICE
CERTIFICATE OF CORRECTION

| | |
|---|---|
| PATENT NO. | : 11,964,016 B2 |
| APPLICATION NO. | : 16/825955 |
| DATED | : April 23, 2024 |
| INVENTOR(S) | : Asrat et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 760 days.

Signed and Sealed this
Twelfth Day of August, 2025

Coke Morgan Stewart
*Acting Director of the United States Patent and Trademark Office*